(12) United States Patent
Seidel et al.

(10) Patent No.: US 7,094,527 B2
(45) Date of Patent: Aug. 22, 2006

(54) SYSTEM FOR IN-VITRO FERTILIZATION WITH SPERMATOZOA SEPARATED INTO X-CHROMOSOME AND Y-CHROMOSOME BEARING POPULATIONS

(75) Inventors: George E. Seidel, LaPorte, CO (US); Tae Kwang Suh, Fort Collins, CO (US); Kehuan Lu, Cambridge (GB)

(73) Assignees: XY, Inc., Fort Collins, CO (US); Colorado State University Through Its Agent Colorado State University Reseach Foundation, Fort Collins, CO (US)

( * ) Notice: Subject to any disclaimer, the term of this patent is extended or adjusted under 35 U.S.C. 154(b) by 276 days.

(21) Appl. No.: 10/433,191

(22) PCT Filed: Nov. 29, 2001

(86) PCT No.: PCT/US01/45237

§ 371 (c)(1), (2), (4) Date: May 29, 2003

(87) PCT Pub. No.: WO02/43486

PCT Pub. Date: Jun. 6, 2002

(65) Prior Publication Data

US 2004/0132001 A1   Jul. 8, 2004

Related U.S. Application Data

(60) Provisional application No. 60/253,785, filed on Nov. 29, 2000, provisional application No. 60/253,787, filed on Nov. 29, 2000.

(51) Int. Cl.
*A01N 1/02* (2006.01)

(52) U.S. Cl. ............................. 435/2; 119/300

(58) Field of Classification Search ............ 435/2; 600/33, 34, 35
See application file for complete search history.

(56) References Cited

U.S. PATENT DOCUMENTS

| | | | |
|---|---|---|---|
| 3,299,354 A | 1/1967 | Hogg | |
| 3,499,435 A | 3/1970 | Rockwell et al. | |
| 3,547,526 A | 12/1970 | Devereux | |
| 3,644,128 A | 2/1972 | Lipner | |
| 3,661,460 A | 5/1972 | Elking et al. | |
| 3,710,933 A | 1/1973 | Fulwyler et al. | |
| 3,761,941 A | 9/1973 | Robertson | |
| 3,810,010 A | 5/1974 | Thom | |
| 3,826,364 A | 7/1974 | Bonner et al. | |
| 3,829,216 A | 8/1974 | Persidsky ................ 356/36 |

(Continued)

FOREIGN PATENT DOCUMENTS

BR  9704313  6/1999

(Continued)

OTHER PUBLICATIONS

Dhali et al. Theriogenology. /2000. vol. 53, No. 6, pp. 1295-1303.*

(Continued)

*Primary Examiner*—Christopher R. Tate
(74) *Attorney, Agent, or Firm*—Santangelo Law Offices, P.C.

(57) ABSTRACT

An IVF system for successfully utilizing spermatozoa separated into X-chromosome bearing and into Y-chromosome bearing population for insemination. The IVF system includes fertilization medium that can shorten the time from insemination to cleavage and a portable incubator for the transportation of maturing oocytes and inseminated oocytes comrprising a straw (19) and an incubation element (20) that can be sealed with a cap (22).

19 Claims, 4 Drawing Sheets

U.S. PATENT DOCUMENTS

| | | | |
|---|---|---|---|
| 3,833,796 A | 9/1974 | Fetner et al. | |
| 3,877,430 A | 4/1975 | Wieder | |
| 3,893,766 A | 7/1975 | Hogg | |
| 3,894,529 A | 7/1975 | Shrimpton | 128/1 R |
| 3,909,744 A | 9/1975 | Wisner et al. | |
| 3,947,093 A | 3/1976 | Goshima et al. | |
| 3,960,449 A | 6/1976 | Carleton et al. | |
| 3,963,606 A | 6/1976 | Hogg | |
| 3,973,003 A | 8/1976 | Colas | |
| 3,973,196 A | 8/1976 | Hogg | |
| 4,009,260 A | 2/1977 | Ericsson | 424/105 |
| 4,014,611 A | 3/1977 | Simpson et al. | |
| 4,067,965 A | 1/1978 | Bhattacharya | 424/105 |
| 4,070,617 A | 1/1978 | Kachel et al. | |
| 4,083,957 A | 4/1978 | Lang | 424/78 |
| 4,085,205 A | 4/1978 | Hancock | 424/105 |
| 4,092,229 A | 5/1978 | Bhattacharya | 204/180 R |
| 4,155,831 A | 5/1979 | Bhattacharya | 207/299 R |
| 4,162,282 A | 7/1979 | Fulwyler et al. | |
| 4,178,936 A | 12/1979 | Newcomb | |
| 4,179,218 A | 12/1979 | Erdmann et al. | |
| 4,191,749 A | 3/1980 | Bryant | 424/105 |
| 4,200,802 A | 4/1980 | Salzman et al. | |
| 4,225,405 A | 9/1980 | Lawson | 204/180 R |
| 4,230,558 A | 10/1980 | Fulwyler | |
| 4,255,021 A | 3/1981 | Brunsden | |
| 4,267,268 A | 5/1981 | Nelson, Jr. | |
| 4,274,408 A | 6/1981 | Nimrod | |
| 4,274,740 A | 6/1981 | Eidenschink et al. | |
| 4,276,139 A | 6/1981 | Lawson | 204/180 R |
| 4,302,166 A | 11/1981 | Fulwyler et al. | |
| 4,317,520 A | 3/1982 | Lombardo et al. | |
| 4,318,480 A | 3/1982 | Lombardo et al. | |
| 4,318,481 A | 3/1982 | Lombardo et al. | |
| 4,318,482 A | 3/1982 | Barry et al. | |
| 4,327,177 A | 4/1982 | Shrimpton | 435/2 |
| 4,339,434 A | 7/1982 | Ericsson | 424/105 |
| 4,341,471 A | 7/1982 | Hogg et al. | |
| 4,350,410 A | 9/1982 | Minott | |
| 4,352,558 A | 10/1982 | Eisert | |
| 4,361,400 A | 11/1982 | Gray et al. | |
| 4,362,246 A | 12/1982 | Adair | 209/3.3 |
| 4,395,397 A | 7/1983 | Shapiro | |
| 4,395,676 A | 7/1983 | Hollinger et al. | |
| 4,400,764 A | 8/1983 | Kenyon | |
| 4,422,761 A | 12/1983 | Frommer | |
| 4,448,767 A | 5/1984 | Bryant | 424/85 |
| 4,474,875 A | 10/1984 | Shrimpton | 435/2 |
| 4,487,320 A | 12/1984 | Auer | |
| 4,515,274 A | 5/1985 | Hollinger et al. | |
| 4,523,809 A | 6/1985 | Taboada et al. | |
| 4,538,733 A | 9/1985 | Hoffman | |
| 4,598,408 A | 7/1986 | O'Keefe | |
| 4,600,302 A | 7/1986 | Sage, Jr. | |
| 4,605,558 A | 8/1986 | Shrimpton | 424/561 |
| 4,631,483 A | 12/1986 | Proni et al. | |
| 4,637,691 A | 1/1987 | Uehara et al. | |
| 4,654,025 A | 3/1987 | Cassou et al. | |
| 4,660,971 A | 4/1987 | Sage et al. | |
| 4,673,288 A | 6/1987 | Thomas et al. | |
| 4,680,258 A | 7/1987 | Hammerling et al. | |
| 4,683,195 A | 7/1987 | Mullis et al. | |
| 4,683,202 A | 7/1987 | Mullis | |
| 4,691,829 A | 9/1987 | Auer | |
| 4,698,142 A | 10/1987 | Muroi et al. | |
| 4,702,598 A | 10/1987 | Böhmer | |
| 4,714,680 A | 12/1987 | Civin | |
| 4,744,090 A | 5/1988 | Freiberg | |
| 4,749,458 A | 6/1988 | Muroi et al. | |
| 4,756,427 A | 7/1988 | Gohde et al. | |
| 4,758,729 A | 7/1988 | Monnin | |
| 4,764,013 A | 8/1988 | Johnston | |
| 4,780,451 A | 10/1988 | Donaldson | |
| 4,790,653 A | 12/1988 | North, Jr. | |
| 4,794,086 A | 12/1988 | Kasper et al. | |
| 4,818,103 A | 4/1989 | Thomas et al. | |
| 4,831,385 A | 5/1989 | Archer et al. | |
| 4,836,038 A | 6/1989 | Baldwyn | |
| 4,845,025 A | 7/1989 | Lary et al. | |
| 4,846,785 A | 7/1989 | Cassou et al. | |
| 4,877,965 A | 10/1989 | Dandliker et al. | |
| 4,942,305 A | 7/1990 | Sommer | |
| 4,959,354 A | 9/1990 | Barbetti | |
| 4,965,204 A | 10/1990 | Civin | |
| 4,979,093 A | 12/1990 | Laine et al. | |
| 4,980,277 A | 12/1990 | Junilla | |
| 4,981,580 A | 1/1991 | Auer | |
| 4,983,038 A | 1/1991 | Ohki et al. | |
| 4,987,539 A | 1/1991 | Moore et al. | |
| 4,988,619 A | 1/1991 | Pinkel | |
| 4,999,283 A | 3/1991 | Zavos et al. | 435/2 |
| 5,005,981 A | 4/1991 | Schulte et al. | |
| 5,007,732 A | 4/1991 | Ohki et al. | |
| 5,021,244 A | 6/1991 | Spaulding | 424/561 |
| 5,030,002 A | 7/1991 | North, Jr. | |
| 5,034,613 A | 7/1991 | Denk et al. | |
| 5,055,393 A | 10/1991 | Kwoh et al. | |
| 5,079,959 A | 1/1992 | Miyake et al. | |
| 5,084,004 A * | 1/1992 | Ranoux | 600/34 |
| 5,088,816 A | 2/1992 | Tomioka et al. | |
| 5,098,657 A | 3/1992 | Blackford et al. | |
| 5,101,978 A | 4/1992 | Marcus | |
| 5,127,729 A | 7/1992 | Oetliker et al. | |
| 5,132,548 A | 7/1992 | Borden et al. | |
| 5,135,759 A | 8/1992 | Johnson | 424/561 |
| 5,144,224 A | 9/1992 | Larsen | |
| 5,150,313 A | 9/1992 | van den Engh et al. | |
| 5,159,397 A | 10/1992 | Kosaka et al. | |
| 5,159,403 A | 10/1992 | Kosaka | |
| 5,162,306 A | 11/1992 | Donaldson | |
| 5,167,926 A | 12/1992 | Kimura et al. | |
| 5,180,065 A | 1/1993 | Touge et al. | |
| 5,182,617 A | 1/1993 | Yoneyama et al. | |
| 5,195,979 A | 3/1993 | Schinkel et al. | |
| 5,199,576 A | 4/1993 | Corio et al. | |
| 5,215,376 A | 6/1993 | Schulte et al. | |
| 5,219,729 A * | 6/1993 | Hodgen | 435/7.21 |
| 5,247,339 A | 9/1993 | Ogino | |
| 5,259,593 A | 11/1993 | Orme et al. | |
| 5,260,764 A | 11/1993 | Fukuda et al. | |
| 5,298,967 A | 3/1994 | Wells | |
| 5,315,122 A | 5/1994 | Pinsky et al. | |
| 5,346,990 A | 9/1994 | Spaulding | 530/350 |
| 5,359,907 A | 11/1994 | Baker et al. | |
| 5,366,888 A | 11/1994 | Fry et al. | |
| 5,367,474 A | 11/1994 | Auer et al. | |
| 5,370,842 A | 12/1994 | Miyazaki et al. | |
| 5,412,466 A | 5/1995 | Ogino | |
| 5,437,987 A | 8/1995 | Teng et al. | |
| 5,439,362 A | 8/1995 | Spaulding | 424/185.1 |
| 5,447,842 A | 9/1995 | Simons | |
| 5,452,054 A | 9/1995 | Dewa et al. | |
| 5,461,145 A | 10/1995 | Kudo et al. | |
| 5,466,572 A | 11/1995 | Sasaki et al. | |
| 5,467,189 A | 11/1995 | Kreikebaum et al. | |
| 5,471,294 A | 11/1995 | Ogino | |
| 5,471,299 A | 11/1995 | Kaye et al. | |
| 5,480,774 A | 1/1996 | Hew et al. | |
| 5,483,469 A | 1/1996 | Van den Engh et al. | |
| 5,494,795 A | 2/1996 | Guerry et al. | |
| 5,496,272 A | 3/1996 | Chung et al. | |
| 5,503,994 A | 4/1996 | Shear et al. | |
| 5,514,537 A | 5/1996 | Chandler | 435/2 |
| 5,523,573 A | 6/1996 | Hanninen et al. | |

| | | | | | | | |
|---|---|---|---|---|---|---|---|
| 5,532,155 | A | * | 7/1996 | Ranoux ........................ 435/325 | 6,528,802 B1 | 3/2003 | Karsten et al. |
| 5,558,998 | A | | 9/1996 | Hammond et al. | 6,534,308 B1 | 3/2003 | Palsson et al. |
| 5,578,449 | A | | 11/1996 | Fr asch et al. | 6,537,829 B1 | 3/2003 | Zarling et al. |
| 5,589,457 | A | | 12/1996 | Wiltbank | 6,577,387 B1 | 6/2003 | Ross, III et al. |
| 5,596,401 | A | | 1/1997 | Kusuzawa | 6,590,911 B1 | 7/2003 | Spinelli et al. |
| 5,601,235 | A | | 2/1997 | Booker et al. | 6,604,435 B1 | 8/2003 | Buchanan et al. |
| 5,601,533 | A | | 2/1997 | Hancke et al. | 6,617,107 B1 | 9/2003 | Dean |
| 5,622,820 | A | | 4/1997 | Rossi | 6,618,679 B1 | 9/2003 | Loehrlein et al. |
| 5,641,457 | A | | 6/1997 | Vardanega | 6,642,018 B1 | 11/2003 | Koller et al. |
| 5,643,796 | A | | 7/1997 | Van den Engh et al. | 6,667,830 B1 | 12/2003 | Iketaki et al. |
| 5,650,847 | A | | 7/1997 | Maltsev et al. | 6,671,044 B1 | 12/2003 | Ortyn et al. |
| 5,660,997 | A | | 8/1997 | Spaulding .................. 435/7.21 | 6,673,095 B1 | 1/2004 | Nordquist |
| 5,663,048 | A | | 9/1997 | Winkfein et al. | 6,704,313 B1 | 3/2004 | De Resende et al. |
| 5,672,880 | A | | 9/1997 | Kain | 6,782,768 B1 | 8/2004 | Buchanan et al. |
| 5,675,401 | A | | 10/1997 | Wangler et al. | 6,819,411 B1 | 11/2004 | Sharpe et al. |
| 5,684,575 | A | | 11/1997 | Steen | 2002/0096123 A1 | 7/2002 | Whittier et al. |
| 5,687,727 | A | | 11/1997 | Kraus et al. | 2002/0113965 A1 | 8/2002 | Roche et al. |
| 5,690,895 | A | | 11/1997 | Matsumoto et al. | 2002/0119558 A1 | 8/2002 | Seidel et al. |
| 5,691,133 | A | | 11/1997 | Critser et al. | 2002/0141902 A1 | 10/2002 | Asbury et al. |
| 5,693,534 | A | * | 12/1997 | Alak et al. .................. 435/366 | 2002/0186375 A1 | 12/2002 | Asbury et al. |
| 5,700,692 | A | | 12/1997 | Sweet | 2003/0098421 A1 | 5/2003 | Ho |
| 5,707,808 | A | | 1/1998 | Roslaniec et al. | 2003/0129091 A1 | 7/2003 | Seidel et al. |
| 5,708,868 | A | | 1/1998 | Ishikawa | 2003/0157475 A1 | 8/2003 | Schenk |
| 5,726,364 | A | | 3/1998 | Van den Engh | 2003/0207461 A1 | 11/2003 | Bell et al. |
| 5,759,767 | A | | 6/1998 | Lakowicz et al. | 2003/0209059 A1 | 11/2003 | Kawano |
| 5,777,732 | A | | 7/1998 | Hanninen et al. | 2004/0005582 A1 | 1/2004 | Shipwast |
| 5,780,230 | A | | 7/1998 | Li et al. | 2004/0031071 A1 | 2/2004 | Morris et al. |
| 5,786,560 | A | | 7/1998 | Tatah et al. | 2004/0049801 A1 | 3/2004 | Seidel |
| 5,793,485 | A | | 8/1998 | Gourley | 2004/0053243 A1 | 3/2004 | Evans |
| 5,796,112 | A | | 8/1998 | Ichie | 2004/0055030 A1 | 3/2004 | Maxwell et al. |
| 5,804,436 | A | | 9/1998 | Okun et al. | 2004/0062685 A1 | 4/2004 | Norton et al. |
| 5,815,262 | A | | 9/1998 | Schrof et al. | 2004/0132001 A1 | 7/2004 | Seidel et al. |
| 5,819,948 | A | | 10/1998 | Van den Engh | 2005/0003472 A1 | 1/2005 | Muhammad |
| 5,824,269 | A | | 10/1998 | Kosaka et al. | 2005/0112541 A1 | 5/2005 | Durack |
| 5,835,262 | A | | 11/1998 | Iketaki et al. | 2005/0214733 A1 | 9/2005 | Graham |
| 5,868,767 | A | | 2/1999 | Farley et al. | | | |
| 5,873,254 | A | * | 2/1999 | Arav ............................ 62/63 | FOREIGN PATENT DOCUMENTS | | |
| 5,876,942 | A | | 3/1999 | Cheng et al. | | | |
| 5,880,457 | A | | 3/1999 | Tomiyama et al. | DE | 69028526 | 2/1997 |
| 5,888,730 | A | | 3/1999 | Gray et al. | DE | 195 49 015 C1 | 4/1997 |
| 5,895,764 | A | | 4/1999 | Sklar et al. | DE | 198 82 943.3 | 2/2001 |
| 5,895,922 | A | | 4/1999 | Ho | EP | 0025296 A2 | 3/1981 |
| 5,899,848 | A | | 5/1999 | Haubrich | EP | 0071538 A1 | 2/1983 |
| 5,912,257 | A | | 6/1999 | Prasad et al. | EP | 0160201 A2 | 11/1985 |
| 5,916,144 | A | | 6/1999 | Prather et al. | EP | 0189702 A1 | 8/1986 |
| 5,916,449 | A | | 6/1999 | Ellwart et al. | EP | 0288029 B1 | 4/1988 |
| 5,919,621 | A | | 7/1999 | Brown | EP | 0276166 A2 | 7/1988 |
| 5,985,216 | A | | 11/1999 | Rens et al. .................... 422/73 | EP | A-0 366794 | 5/1990 |
| 5,985,538 | A | * | 11/1999 | Stachecki .................... 435/1.1 | EP | 0461618 | 12/1991 |
| 6,002,471 | A | | 12/1999 | Quake | EP | 0468100 A1 | 1/1992 |
| 6,050,935 | A | * | 4/2000 | Ranoux et al. ................ 600/33 | EP | 0570102 A1 | 3/1993 |
| 6,071,689 | A | * | 6/2000 | Seidel et al. .................... 435/2 | EP | 0538786 A | 4/1993 |
| 6,087,352 | A | | 7/2000 | Trout | EP | 0606847 | * 7/1994 |
| 6,117,068 | A | | 9/2000 | Gourley et al. | EP | 606847 A2 | 7/1994 |
| 6,119,465 | A | * | 9/2000 | Mullens et al. ................ 62/60 | EP | A-0 478155 | 1/1998 |
| 6,133,044 | A | | 10/2000 | Van den Engh | EP | 0781985 A3 | 7/1998 |
| 6,140,121 | A | * | 10/2000 | Ellington et al. ........... 435/374 | EP | 1250897 A1 | 10/2002 |
| 6,149,867 | A | | 11/2000 | Seidel et al. .................. 422/73 | EP | 1403633 A3 | 4/2004 |
| 6,153,373 | A | | 11/2000 | Benjamin et al. | FR | 2574656 A1 | 6/1986 |
| 6,154,276 | A | | 11/2000 | Mariella, Jr. | FR | A-2 635453 | 2/1990 |
| 6,175,409 | B1 | | 1/2001 | Nielsen et al. | FR | 2 647 668 A | 12/1990 |
| 6,177,277 | B1 | | 1/2001 | Soini | FR | 2 699 678 A1 | 12/1992 |
| 6,238,920 | B1 | | 5/2001 | Nagai et al. | JP | 61139747 (A) | 6/1986 |
| 6,248,590 | B1 | | 6/2001 | Malachowski | JP | 61159135 (A) | 7/1986 |
| 6,263,745 | B1 | | 7/2001 | Buchanan et al. .......... 73/865.5 | JP | 2024535 | 1/1990 |
| 6,283,920 | B1 | * | 9/2001 | Eberle et al. ................ 600/459 | JP | 4126064 (A) | 4/1992 |
| 6,357,307 | B1 | | 3/2002 | Buchanan et al. .......... 73/865.5 | JP | 4126065 (A) | 4/1992 |
| 6,372,422 | B1 | | 4/2002 | Seidel et al. .................... 435/2 | JP | 4126066 (A) | 4/1992 |
| 6,395,305 | B1 | | 5/2002 | Buhr et al. | JP | 4126079 (A) | 4/1992 |
| 6,411,835 | B1 | | 6/2002 | Modell et al. | JP | 4126080 (A) | 4/1992 |
| 6,463,314 | B1 | | 10/2002 | Haruna | JP | 4126081 (A) | 4/1992 |
| 6,489,092 | B1 | | 12/2002 | Benjamin et al. | SU | 1056008 | 11/1983 |
| 6,524,860 | B1 | | 2/2003 | Seidel et al. | SU | 1260778 A1 | 9/1986 |

| | | |
|---|---|---|
| WO | WO 88/07198 | 9/1988 |
| WO | WO 90/13315 | 11/1990 |
| WO | WO 96/12171 | 4/1996 |
| WO | WO 96/31764 | 10/1996 |
| WO | WO 98/34094 A1 | 8/1998 |
| WO | WO 98/48259 | 10/1998 |
| WO | WO 99/05504 | 2/1999 |
| WO | WO 99/33956 | 7/1999 |
| WO | WO 99/38883 A1 | 8/1999 |
| WO | WO 99/44037 A1 | 9/1999 |
| WO | WO 00/06193 | 2/2000 |
| WO | WO 01/37655 A1 | 5/2001 |
| WO | WO 01/40765 A2 | 6/2001 |
| WO | WO 01/40765 A3 | 6/2001 |
| WO | WO 01/51612 A1 | 7/2001 |
| WO | WO 01/85913 A2 | 11/2001 |
| WO | WO 01/85913 A3 | 11/2001 |
| WO | WO 01/90295 A1 | 11/2001 |
| WO | WO 01/95815 A1 | 12/2001 |
| WO | WO 02/19943 A1 | 3/2002 |
| WO | WO 02/28311 A2 | 4/2002 |
| WO | WO 02/41906 A2 | 5/2002 |
| WO | WO 02/43486 A1 | 6/2002 |
| WO | WO 02/43574 A2 | 6/2002 |
| WO | WO 04/009237 A1 | 1/2004 |
| WO | WO 04/012837 A1 | 2/2004 |
| WO | WO 04/012837 A3 | 2/2004 |
| WO | WO 04/017041 A2 | 2/2004 |
| WO | WO 04/017041 A3 | 2/2004 |
| WO | WO 04/024227 A2 | 3/2004 |
| WO | WO 2004/059282 A2 | 7/2004 |
| WO | WO 2004/003697 A2 | 10/2004 |
| WO | WO 2004/087177 A1 | 10/2004 |
| WO | WO 2004/088283 A2 | 10/2004 |
| WO | WO 04/104178 A2 | 12/2004 |
| WO | WO 2005/094852 A2 | 10/2005 |
| WO | WO 2005/095590 A2 | 10/2005 |
| WO | WO 2005/095960 A1 | 10/2005 |

OTHER PUBLICATIONS

Boringi et al. Fertil. Steril. 1997. vol. 68, Suppl. p. S196, P-218.*
Catt, et al., "Assessment of Ram and Boar Spermatozoa During Cell-Sorting by Flow Cytometry", Reproduction Dom Animal, vol. 32, 1997, pp. 251-258.
Catt, S.L., et al., "Birth of a Male Lamb Derived from an In Vitro Matured Oocyte Fertilized by Intracytoplasmic Injection of a Single Presumptive Male Sperm", Veterinary Record 139, 1996, pp. 494-495.
Day, B.N. et al., 1998. Birth of piglets preselected for gender following in vitro fertilization of in vitro matured pig oocytes by X and Y bearing spermatozoa sorted by high speed flow cytometry. Theriogenology. 49(1):360. abstr.
Dinnyes, A., et al., "Timing of the First Cleavage Post- Insemination Affects Cryosurvival of In Vitro-produced Bovine Blastocysts", Molec. Reprod. Develop. 53, p. 318-324. 1999.
Grondahl, C., et al, "In Vitro Production of Equine Embryos", Biology of Reproduction, Monograph Series I, pp. 299-307 (1995).
Hamano, K., et al., "Gender Preselection in Cattle with Intracytoplasmically Injected, Flow Cytometrically Sorted Sperm Heads", biology of Reproduction 60, 1999, pp. 1194-1197.
Jafar, et al., "Sex Selection in Mammals: A Review", Theriogenology, vol. 46, 1996, pp. 191-200.
Lonergan, P., et al., "Effect of Time Interval from Insemination to First Cleavage on the Development of Bovine Embryos In Vitro and In Vivo", Theriogenology, 1999, p. 326.
Long, C.R., Rath, D., Welch, G.R., Schreier, L.L., Dobrinsky, J.R. and Johnson, L.A. *1998.* Aln vitro production of porcine embryos from semen sorted for sex with a high speed cell sorter: comparison of two fertilization media.@, Theriogenology. 49(1):363. abstr.
Lu, K. H. et al., "In Vitro Fertilization of Bovine Oocytes with Flow-Cytometrically Sorted and Unsorted Sperm from Different Bulls" Therio. abstr.
Lu, K.H., et al., "In Vitro Fertilization with Flow-Cytometrically-Sorted Bovine Sperm", Theriogenology 52, 1999, pp. 1393-1405.
McNutt, T. L. et al., "Flow Cytometric Sorting of Sperm: Influence on Fertilization and Embryo/Fetal Development in the Rabbit", Molecular Reproduction and Development, vol. 43, p. 261-267 (1996).
Melamed et al, "An Historical Review of the Development of Flow Cytometers and Sorters", 1979, pp. 3-9.
Rieger, D., et al, "The Relationship Between the Time of First Cleavage of Fertilized Cattle Oocytes and Their Development to the Blastocyst Stage", Theriogenology, 1999, pp. 190.
Seidel, G., "Use of Sexed Bovine Sperm for In Vitro Fertilization and Superovulation", Animal Reproduction and Biotech Lab, CSU, Proceedings of the 2000 CETA/ACTE Convention, Charlottetown, Prince Edward Island, Aug. 2000, pp. 22-24.
Abdel-Ghaffar, A. E., et al., "Rabbit Semen Metabolism" in Rabbit Production in Hot Climates Baselga and Marai (eds); International Conference of Rabbit Production in Hot Climates 1994, p. 305-312.
Akhtar, S., et al., "Prevalence of Five Stereotypes of Bluetongue Virus in a Rambouillet Sheep Flock in Pakistan", Veterinary Record 136, p. 495. (1995).
Aldrich, S. L., et al., "Parturition and Periparturient Reproductive and Metabolic Hormone Concentration in Prenatally Androgenized Beef Heifers", J. Anim. Sci. 73:3712. (1995).
Amann, R. P. et al., "Issues Affecting Commercialization of Sexed Sperm" Therio. 52:1441. (1999).
Amann, R. P., et al. "Prospects For Sexing Mammalian Sperm," Animal Reproduction Laboratory College of Veterinary Medicine and Biomedical Sciences, Colorado State University. (1982).
Amann, R.P. "Fertilizing Potential Vitro of Semen from Young Beef Bulls Containing a High or Low Percentage of Sperm with a Proximal Droplet" Theriogenology 54: 1499-1515, 2000.
Amann, Rupert P. "Cryopreservation of Sperm" 1999, Encyclopedia of Reproduction 1:733-783.
American Meat and Science Association in Cooperation with National Livestock and Meat Board, "Research Guidelines for Cookery and Sensory Evaluation and Instrumental Tenderness Measurements for Fresh Meat". (1995).
Amoah, E. A. and Gelaye, S., "Biotechnological Advances in Goat Reproduction", J. Anim. Sci. 75(2): 578-585. (1996).
Anderson, V. K., et al., Intrauterine und tiefzervikale Insemination mit Gefriersperma bein Schat (Intrauterine and Deep Cervical Insemination With Frozen Semen in Sheep). Zuchthygiene 8:113-118. (1973).
Arriola, J. and Foote, R.H.: "Glycerolation and Thawing Effects on Bull Spermatozoa frozen in Detergent-Treated Egg Yok and Whole Egg Extenders," J Dairy Sci, 70:1664-1670 (1987).
Asbury, Charles A. "Fluorescence Spectra of DNA Dyes Measured in a Flow Cytometer," University of Washington Feb. 19, 1996.
Bagley, C. P. "Nutritional Management of Replacement Beef Heifers: a Review" J. Anim. Science 71:3155-3163. (1993).
Bailey, C. M. et al., "Nulliparous Versus Primiparous Crossbred Females for Beef", J. Anim. Sci. 69:1403. (1991).
Baker, R.D., et al., "Effect of Volume of Semen, Number of Sperm and Drugs on Transport of Sperm in Artificially Inseminated Gilts", J. Anim. Sci. 27:88-93. (1968).
Bakker Schut, Tom C. "A New Principle of Cell Sorting by Using Selective Electroportation in a Modified Flow Cytometry," University of Twente, Mar. 10, 1990.
Barnes, F. L. and Eyestone, W. H., "Early Cleavage and the Maternal Zygotic Transition in Bovine Embryos", Therio. vol. 33, No. 1, pp. 141-149. (1990).
Batellier, F. et al., "Advances in Cooled Semen Technology" Animal Reproduction Science 68 p. 181-190 (2001).
Becker, S.E. and Johnson, A. L. "Effects of Gonadotropin-Releasing Hormone Infused in a Pulsatile or Continuous Fashion on Serum Gonadotropin Concentrations and Ovulation in the Mare", J. Anim. Sci. 70:1208-1215. (1992).
Bedford, S .J. and Hinrichs, K., "The Effect of Insemination Volume on Pregnancy Rates of Pony Mares", Therio. 42:571-578. (1994).
Behrman, S. J., et al., "Freeze Preservation of Human Sperm" American Journal of Obstetrics and Gynecology vol. 103 (5) p. 654-664 Mar. 1, 1969.

Bellows, R. A., et al., "Cause and Effect Relationships Associated With Calving Difficulty and Calf Birth Weight", J. Anim. Sci. 33:407. (1971).

Berardinelli, J. G., et al., "Source of Progesterolle Prior to Puberty In Beef Heifers". J. Anim. Sci. 49:1276. (1979).

Berger, G. S. "Intratubal Insemination", Fertil. Steril. 48:328-330, (1987).

Bergfeld, E. G., et al., "Ovarian Follicular Development in Prepubertal Heifers is Influenced by Level of Dietary Energy Intake", Bio. of Repro. 51:1051. (1994).

Berry, B. W., et al., "Beef Carcass Maturity Indicators and Palatability Attributes", J. Anim. Sci. 38:507 (1974).

Beyhan, Z., et al., "Sexual Dimorphism in IVF Bovine Embryos Produced by Sperm Sorted by High Speed Flow Cytometry", abstr. Therio. 49(1): 359 (1998).

Beyhan, Z., Et Al., 1999 Sexual Dimorphism In IVM-IVF Bovine Embryos Produced from X and Y Chromosome-Bearing Spermatozoa Sorted By High Speed Flow Cytometry. Theriogenology. 52: 35-48.

BigosBigos, Martin "Nine Color Eleven Parameter Immunophenotyping Using Three Laser Flow Cytometry," Stanford University Dec. 22, 1998.

Bioxcell, Bovine Sperm Preservation, Advertisement Jun. 28, 2005.

Bond, J., et al., "Growth and Carcass Traits of Open Beef Heifers Versus Beef Heifers That Have Calved", Nutrition Reports International 34:621. 1986.

Boucque, C. V., et al., "Beef-Production With Maiden and Once-Calved Heifers", Livestock Prod. Sci. 7:121. 1980.

Bourdon, R. M. and J. S. Brinks. "Simulated Efficiency of Range Beef -Production III. Culling Strategies and Nontraditional Management-Systems", J. Anim. Sci. 65:963. 1987.

Bracher, V. and Allen, W.R., "Videoendoscopic Examination of the Mare's Uterus: I. Findings in Normal Fertile Mares", Equine Veterinary Journal, vol. 24, p. 274-278. 1992.

Braselton, W. E. and McShan, W. H., "Purification and Properties of Follicle Stimulating and Luteinizing Hormones From Horse Pituitary Glands" Arch. Biochem. Biophys. 139:45-48. 1970.

Braun, J. et al, "Effect of Different Protein Supplements on Motility and Plasma Membrane Integrity of Frozen- Thawed Stallion Spermatozoa", Cryobiology (1995) 32:487-492.

Brethour, J. R. and Jaeger, J. R., "The Single Calf Heifer System", Kansas Agric. Sta. Rep of Progress 570. 1989.

Brinsko, S.P. et al., "Artificial Insemination and Preservation of Semen." Veterinary Clinics of North America:Equine Practice vol. 8 NUM.1 Apr. 1992. pp. 205-218.

Bristol, F. "Breeding Behavior of a Stallion at Pasture With 20 Mares in Synchronized Oestrus" J. Reprod. Fertil. Suppl. 32:71. 1982.

Brookes, A. J. and O'Byrne, M., "Use of Cow-Heifers in Beef Production" J. of the Royal Agricultural Society of England 126:30. 1965.

Buchanan, B. R., et al, "Insemination of Mares with Low Numbers of Either Unsexed or Sexed Spermatozoa", Therio. vol. 53, p. 1333-1344. 2000.

Buchanan, B.R. "Pregnancy Rates in Mares Following a Single Insemination with a Low Number of Spermatozoa into the Tip of the Uterine Horn" Theriologenology p. 395.

Burns, P. D. and Spitzer, J.C., "Influence of Biostimulation on Reproduction in Postpartum Beef-Cows", J. Anim. Sci. 70:358. 1992.

Burwash, L. D., et al., "Relationship of Duration of Estrus to Pregnancy Rate in Normally Cycling, Non Lactating Mares" J.A.V.M.A. 165:714-716. 1974.

Byerley, D. J., et al., "Pregnancy Rates of Beef Heifers Bred Either on Puberal or Third Estrus". J Anim. Sci. 65:645. 1987.

Caslick, E. A., "The Vulva and the Vulvo-Vaginal Orifice and its Relation to Genital Health of the Thoroughbred Mare", Cornell Veterinarian, vol. 27, p. 178-187. 1937.

Cave-Penney, Tony, "Sexed Semen Offers Faster Genetic Gain", Farming News, Livestock Supplement, Feb. 1997, p. 28.

*Celestron: Telescope Basics*: www.celestron.com/tb-2ref/htm; 4 pages.

Chandler, J. E., "Videomicroscopic Comparison of Bull Sperm and Leukocyte Chromosome Areas as Related to Gender", J Dairy Sci 73, p. 2129-2135. 1990.

Chandler, J. E., et al, "Bovine Spermatozoal Head Size Variation and Evaluation of a Separation Technique Based on this Size", Therio. 52, p. 1021-1034. 1999.

Chen, S.H. "Effects of Oocyte Activation and Treatment of Spermatozoa on Embryonic Development Following Intracytoplasmic Sperm Injection in Cattle" Theriogenology 48: 1265-1273, 1997.

Chen, Y. et al., Survival of Bull Spermatozoa Seeded and Frozen at Different Rates in Egg Yolk-Tris and Whole Milk Extenders, 1993 J Dairy Sci 76:1028-1034.

Chin, W. W. and Boime, I. 1990. In Glycoprotein Hormones. Serona Symp. Norwell, MA. pp. 19-20.

Choi, Y.H. "Developmental Cappacity of Equine Oocytes Matured and Cultured in Equine Trophoblast-Conditioned Media" Theriogenoogy 56: 320-339, 2001.

Chung, Y. G., et al. "Artificial insemination of Superovulated Heifers With 600,000 Sexed Sperm". J Anim. Sci. Suppl. 1. 836:215. 1998 abstr.

Clement, F., et al., "Which Insemination Fertilizes When Several Successive Inseminations are Performed Before Ovulation" 7th Int. Symp. Eq. Repro. 151. 1998 abstr.

Cran, D. G., et al, "Production of Lambs by Low Dose Intrauterine Insemination With Flow Cytometrically Sorted and Unsorted Semen", Therio. p. 267. 1997.

Cran, D. G., et al., "Sex Preselected in Cattle: A Field Trial", Veterinary Record 136, 1995, p. 495-496.

Cran, D. G., et al., "Production of Bovine Calves Following Separation of X- and Y-Chromosome Bearing Sperm and In Vitro Fertilization". Vet. Rec. 132:40-41. 1993.

Cran, D. G., et al., "The Predetermination of Embryonic Sex Using Flow Cytometrically Separated X and Y Spermatozoa" Human Reproduction Update 1996, vol. 2 (4) p. 355-63.

Crowley, J. P. "The facts of Once-Bred Heifer Production" School of Agric., Univ. of Aberdeen, Scotland. 1973.

Cui, K. et al, "X Larger than Y", Nature 366, p. 177-118, 1993.

Cui, K., "Size Differences Between Human X and Y Spermatozoa and Prefertilization Diagnosis", Molecular Human Reproduction, vol. 3, No. 1, pp. 61-67. 1997.

Curran, S. "Fetal Gender Determination" in *Equine Diagnostic Ultrasonography* 1st ed. Rantanen, N.W. and McKinnon A.O. (eds.) Williams and Williams, 1998, p. 165-69.

da Silva, Coutinho M.A.." Effect of time of oocyte collection and site of insemination of oocyte transfer in mares." Animal Reproduction and Biotechnology Laboratiory, Colorado State University, Fort Collins Journal of Animal Science 2002. 80:1275-1279.

*DakoCytomation, "MoFlo® Sorters"* http://www.dakocytomation.us/prod_productrelatedinformation?url=gprod_moflo_index.htm one page, printed Jun. 26, 2003.

Database up 1 BR9704313 (Alves, De Resende et al) Jun. 4, 1999.

de Leeuw, F.E. et al:" Effects of carious cryoprotective agents and membrane-stabilizing compounds on bull sperm emebrane integrity after cooling and freezing" Cryobiology Us, Academic Press Inc 1993 pp. 32-44.

Dean, P.N., et al. "Hydrodynamic Orientation of Spermatozoa Heads for Flow Cytometry". Biophys. J. 23:7-13. 1978.

Demick, D.S., et al. "Effect of Cooling, Storage, Glycerization and Spermatozoal Numbers on Equine Fertility" J. Anim. Sci. 43:633-637. 1976.

DenDaas, J. H. G., et al. "The relationship between the number of spermatozoa inseminated and the reproductive efficiency of dairy bulls" J Dairy Sci. 81: 1714-1723. 1998.

Denham, A. "In-vitro studies on Sandhill Range Forage as Related to Cattle Preference", M.S. Thesis. Colorado State University. 1965.

Denk, Winfried. "Two-Photon Molecular Excitation in Laser-Scanning Microscopy, " Handbook of Biological Confocal Microscopy. 1995.

Deutscher, G. H. "Extending Interval From Seventeen to Nineteen Days in the Melengestrol Acetate-Prostaglandin Estrous Synchronization Program for Heifers". The Professional Animal Scientist 16:164. 2000.

*Diagnostic Products Corporation, "Coat-A-Count"* http://www.Progesterone.com. 1998.

Dikeman, M. E. "Cattle Production Systems to Meet Future Consumer Demands" J. Anim. Sci. 59:1631, 1984.

Dippert, K.D. "Fertilization Rates in Superovulated and Spontaneously Ovulating Mares" Theriogenology 41: 1411-1423, 1994.

Donaldson, L. E., "Effect of Insemination Regimen on Embryo Production in Superovulated Cows", The Veterinary Record, Jul. 13, p. 35-37, 1985.

Donoghue, A.M., et al. "Timing of Ovulation after Gonadotropin Induction and its Importance to Successful Intrauterine Insemination in the Tiger (Panthera tigris)" J. Reprod. Fertil. 107:53-58. 1996.

Douglas, R. H., "Review of Induction of Superovulation and Embryo Transfer in the Equine" Therio. 11:33-46. 1979.

Douglas, R. H., et al. "Induction of Ovulation and Multiple Ovulation on Seasonally-Anovulatory Mares with Equine Pituitary Fractions." Therio. 2(6): 133-142. 1974.

Doyle, S. P., et al. "Artificial Insemination of Lactating Angus Cows with Sexed Semen". Proc. Western Sect. Am. Soc. Anim. Sci. 50:203. 1999.

Dresser D.W. et at. Analysis of DNA content of Living Spermatozoa Using Flow Cytometry Technique Journal of Reproduction and Fertility, 1993, vol. 98, pp. 357-365.

Duchamp, G., et al. "Alternative Solutions to hCG Induction of Ovulation in the Mare" J. Reprod. Fertil. Suppl. 35:221-228. 1987.

Evans, M. J. and Irvine, C. H. G. "Induction of Follicular Development, Maturation and Ovulation by Gonadotropin Releasing Hormone Administration to Acyclic Mares" Bio. Reprod. 16:452-462. 1977.

Ferrell, C. L. Effects of Post-Weaning Rate of Gain on Onset of Puberty and Productive Performance of Heifers of Different Breeds. J. Anim. Sci. 55:1272. 1982.

Ferrell, C. L. and T. G. Jenkins. "Energy-Utilization by Mature, Nonpregnant, Nonlactating Cows of Different Types" J. Anim. Sci. 58:234. 1984.

Field, R. A., et al., "Bone-Ossification and Carcass Characteristics of Wethers Given Silastic Implants Containing Estradiol", J. Anim. Sci. 68:3663-3668. 1990.

Field, R. et al., "Growth, Carcass, and Tenderness Characteristics of Virgin, Spayed, and Single-Calf Heifers", J. Anim. Sci. 74:2178. 1996.

Fitzgerald, B. P., et al. "Effect of Constant Administration of a Gonadotropin-Releasing Hormone Agonist on Reproductive Activity in Mares: Preliminary Evidence on Suppression of Ovulation During the Breeding Season." Am. J. Vet. Res. 54:1746-1751. 1993.

Fluharty, F. L., et al., "Effects of Age at Weaning and Diet on Growth of Calves",Ohio State University Dept. of Animal Scieneces. 1966 Ohio Agri. Res. And Den. Circular, 156:29 1966.

Foote, et al. Motility and Fertility of Bull Sperm Frozen-Thawed Differently in Egg Yolk and Milk Extenders Containing Detergent, 1987 J Dairy Sci 70:2642-2647.

Foote, R.H., "Buffers and Extenders: What Do They Do? Why Are They Important?" Proc of the NAAB Tech. Comf. On Artificial Insemination and Reproduction, 62-70 (1984).

Foulkes, J. A., et al. "Artificial Insemination of Cattle Using Varying Numbers of Spermatozoa." Vet. Rec. 101:205. 1977.

Francon, M. and Yamamoto, T., "Un Noveau et tres simple dispositif interferentiel applicable as microscope" Optica Acta 9, p. 395-408.1962.

Fugger, E. F. "Clinical Experience with Flow Cytometric Separation of Human X- and Y- Chromosome Bearing Sperm", Therio. vol. 52, pp. 1435-1440.1999.

Fuller, Robert R. "Characterizing Submicron Vesicles With Wavelenth-Resolved Fluorescence in Flow Cytometry," University of Illinois, May 13, 1996.

Fulwyler, M. J. "Electronic Separation of Biological Cells by Volume." Science. 150:910. 1965.

Fulwyler, M. J. "Hydrodynamic Orientation of Cells." J of Histochem. and Cytochem. 25:781-783. 1977.

Garner, D. L., et al. "Quantification of the X and Y Chromosome-Bearing Spermatozoa of Domestic Animals by Flow Cytometry." Biol. Reprod. 28:312-321. 1983.

Ginther, O. J., "Sexual Behavior Following Introduction of a Stallion into a Group of Mares" Therio. vol. 19 (6) Jun. 1983.

Ginther, O. J., "Some Factors Which Alter Estrus Cycle in Mares." J. Anim. Sci. 33:1158. 1971 abstr.

Ginther, O. J., Reproductive Biology of the Mare. (2nd Ed.) Equiservices, Cross Plains, WI. 1992.

Gledhill, B. L. "Gender Preselection: Historical, Technical and Ethical Perspective." Semen Reprod. Endocrinol. 6:385-395. 1988.

Gombe, S. and Hansel, W. "Plasma Luteinizing Hormone (LH) and Progesterone Levels in Heifers on Restricted Energy Intakes." J. Anim. Sci. 37:728. 1973.

Goppert-Mayer,"Uber Elementarakte mit zwei Quantensprungen Von Maria Copper -Mayer".

Gottlinger et al., "Operation of a Flow Cytometer", Flow Cytometry and Cell Sorting, A. Radbruch (Ed.), 1992, pp. 7-23.

Gourley, D. D. and Riese, R. L. "Laparoscopic Artificial Insemination in Sheep." Vet. Clin. N. Amer: Food Anim. Prac. 6(3): 615-633 (1990).

Graham, J. Analysis of Stallion semen and its Relation to Fertility. ABSTRACT.

Graham, J.K. and Hammerstedt, R.H.: "Differential Effects of Butylated Hydroxytoluene Analogs on Bull Sperm Subjected to Cold-Induced Membrane Stress," Cryobiology, 29:106-117 (1992).

Graham, James K., "Effect of Cholesterol-Loaded Cyclodextrins in Semen Extenders", Proceedings of the 19th Technical Conference on Artificial Insemination & Reproduction, 2003, pp. 91-95.

Gravert, H. O., "Genetic Aspects of Early Calving." In: J.C. Taylor (Ed.) *The Early Calving of Heifers and Its Impact on Beef Production*. 59 (1975).

Gregory, K. E., et al., "Characterization of Biological Types of Cattle—Cycle lll: ll Growth Rate and Puberty in Females" J. Anim. Sci. 49:461 (1979).

Grimes, I. F, and T.B. Turner. "Early Weaning of Fall Born Calves ll. Post Weaning Performance of Early and Normal Weaned Calves". 1. Prod. Agric. 4:168 (1991).

Guillou, F. and Combarnous, Y. "Purification of Equine Gonadotropins and Comparative Study of Their Acid-Dissociation and Receptor-Binding Specificity." Biochemica Et Biophysica Acta 755:229-236 (1983).

Gumsey, M. P., and Johnson, L.A., "Recent Improvements in Efficiency of Flow Cytometric Sorting of X and Y-Chromosome Bering Sperm of Domestic Animals: a Review" New Zealand Society of Animal Protection, three pages (1998).

Hall, J. B., et al., "Effect of Age and Pattern of Gain on Induction of Puberty with a Progestin in Beef Heifers." J. Anim. Sci. 75:1606 (1997).

*Hamamatsu, "Technical Information, Optical Detector Selection: A Delicate Balancing Act", web page,* http://www.optics.org/hamamatsu/photodiode.html, *printed on Apr. 15, 2000, 6 pages total.*

Hammerstedt, et al., "Cryopreservation of Mammalian Sperm: What We Ask Them to Survive," Journal of Andrology, 11:1:73-88 (1990).

Harrison, L.A., et al., "Comparison of HCG, Buserelin and Luprostiol for Induction of Ovulation in Cycling Mares." Eq. Vet. Sci. 3:163-166 (1991).

Harte, F. J. "System of Production of Beef From Once Calved Heifers." In: J.C. Taylor (Ed.) *The Early Calving of Heifers and its Impact on Beef Production*. 123 (1975).

Hawk, H. W., et al., "Fertilization Rates in Superovulating Cows After Deposition of Semen on the Infundibulum Near the Uterotubal Junction of After Insemination with High Numbers of Sperm", XP-002103478, Therio. vol. 29, No. 5, p. 1131-1142 (1988).

Hermesmeyer, G. N., et al. "Effects of Prenatal Androgenization and Implantation on the Performance and Carcass Composition of Lactating Heifers in the Single-Calf Heifer System." The Professional Animal Scientist 15:173. 1999.

Herweijer, Hans. "High-Speed Photodamage Cell Selection Uing Bromodeoxyuridine/Hoechst 33342 Photosensitized Cell Killing," Sep. 23, 1987.

Herzenberg, Leonard A. "Flourescence-activated Cell Sorting," pages 108-117.

Hilton, G. G., et al., "An Evaluation of Current and Alternative Systems for Quality Grading Carcasses of Mature Slaughter Cows." J. Anim. Sci. 76:2094. 1998.

Ho, L., et al., "Influence of Gender, Breed and Age on Maturity Characteristics of Sheep." J. Anim. Sci. 67:2460-2470. 1989.

Hofferer, S., et al. "Induction of Ovulation and Superovulation in Mares Using Equine LH and FSH Separated by Hydrophobic Interaction Chromatography." J. Reprod. Fertil. 98:597-602. 1993.

Hohenboken, W. D. "Applications of sexed semen in cattle production." Therio. 52:1421. 1999.

Holtan, D. W., et al., "Estrus, Ovulation and Conception Following Synchronization With Progesterone, Prostaglandin F2a and Human Chorionic Gonadotropin in Pony Mares." J. Anim. Sci. 44:431-437. 1977.

Horan, Paul K. "Quantitative Single Cell Ana,lysis and Sorting, Rapid Analysis and sorting of cells is emerging as an important new technology in research and medicine.".

Householder, D. D., et al. "Effect of Extender, Number of Spermatozoa and hCG on Equine Fertility." J. Equine Vet. Sci. 1:9-13. 1981.

Howard, J. G., et al., "Comparative Semen Cryopreservation in Ferrets (Mustela putorious furo) and Pregnancies After Laparoscopic Intrauterine Insemination With Frozen-Thawed Spermatozoa." J. Reprod. Fertil. 92:109-118. 1991.

Howard, J. G., et al., "Sensitivity to Exogenous Gonadotropins for Ovulation and Laparoscopic Artificial Insemination in the Cheetah and Clouded Leopard." Biol. Reprod. 56:1059-1068. 1997.

Hunter, R. H. F. "Transport and Storage of Spermatozoa in the Female Tract." Proc 4th Int. Congress Anim. Repro. and A. I. 9:227-233. 1980.

Hyland, J. H., et al., "Gonadotropin Releasing Hormone (GnRH) Delivered by Continuous Infusion Induces Fertile Estrus in Mares During Seasonal Acyclity" Proceedings of the Annual Convention of the American Association of Equine Practitioners (34th) 989, p. 181-190.

IMV Technologies, Protocol of Bioxcell with Fresh Semen, 1 page, 2000.

IMV Technologies, Protocol of Bioxcell with Frozen Semen, 2 pages, 2000.

Irvine, C H. G. and Alexander, S. L. "GnRH" Chapter 4 in Equine Reproduction, McKinnon and Voss eds. Lea and Febiger. Philadelphia, London. p. 37. (1993).

Iwazumi, Y., et al., "Superovulation Using CIDR in Holstein Cows" J. of Reprod. Dev. vol. 40 (3) 1994, pp. 259-266.

Jakubiczka, S. et al. "A Bovine Homologue of the Human TSPY Gene." Genomics. 1993, vol. 17, No. 3, pp. 732-735.

Jarriage, R. "Age of Cows at First Calving in France." In: J.C. Taylor (Ed.) *The Early Calving of Heifers and its Impact on Beef Production*. 10. (1975).

Jasko, D. J., et al., "Effect of Insemination Volume and Concentration of Spermatozoa on Embryo Recovery in Mares", Therio. 37:1233-1239, (1992).

Jasko, D. J., et al., "Pregnancy Rates Utilizing Fresh, Cooled and Frozen-Thawed Stallion Semen", American Association of Equine Practitioners 38th Annual Convention Proceedings, 1992, p. 649-60.

Johnson, A. L. "Pulsatile Administration of Gonadotropin Releasing Hormone Advances Ovulation in Cycling Mares", Biol. Reprod. 35:1123-1130, (1986).

Johnson, A. L., et al. "Use of Gonadotropin-Releasing Hormone (GnRH) Treatment to Induce Multiple Ovulations in the Anestrous Mare" Eq. Vet. Sci. 8:130-134, (1988).

Johnson, L.A., "Flow Cytometric Determination of Spermatozoa Sex Ration in Semen Purportedly Enriched for X or Y Bearing Spermatozoa", Therio. 29:265 abstr.

Johnson, L.A., "Gender Preselection in Domestic Animals Using Flow Cytometrically Sorted Sperm" J. Anim. Sci. (Suppl l) 70:8-18. (1992).

Johnson, L.A., "The Safety of Sperm Selection by Flow Cytometry" Ham. Reprod. 9(5): 758. (1994).

Johnson, L.A., "Advances in Gender Preselection in Swine" Journal of Reproduction and Fertility Supplement, vol. 52, p. 255-266 (1997).

Johnson, L.A., "Gender Preselection in Humans? Flow Cytometric Separation of X and Y Spermatozoa for the Prevention of X-Linked Diseases" Human Reproduction vol. 8 No. 10, p. 1733-1739 (1993).

Johnson, L.A., "Gender Preselection in Mammals: An Overview", Deutsch. Tierarztl. Wschr, vol. 103, p. 288-291 (1996).

Johnson, L.A., "Isolation of X- and Y-Bearing Spermatozoa for Sex Preselection." Oxford Reviews of Reproductive Biology. Ed. H. H. Charlton. Oxford University Press. 303-326. (1994).

Johnson, L.A., "Sex Preselection by Flow Cytometric Separation of X and Y Chromosome Bearing Spermatozoa Based on DNA Difference: a Review." Reprod. Fertil. Dev. 7:893-903. (1995).

Johnson, L.A., "Sex Preselection in Rabbits: Live Births from X and Y Sperm Separated by DNA and Cell Sorting", Biology of Reproduction 41, pp. 199-203 (1989).

Johnson, L.A., "Sex Preselection in Swine: Altered Sex Rations in Offspring Following Surgical Insemination of Flow Sorted X- and Y- Bearing Sperm", Reproduction in Domestic Animals, vol. 26, pp. 309-314 (1991).

Johnson, L.A., "Sex Preselection in Swine: Flow Cytometric Sorting of X- and Y- Chromosome Bearing Sperm to Produce Offspring", Boar Semen Preservation IV, p. 107-114. (2000).

Johnson, L.A., "Successful Gender Preselection in Farm Animals", Agricultural Biotechnology, p. 439-452. (1998).

Johnson, L.A., et al. "Sex Preselection: High-speed Flow Cytometric Sorting of X and Y Sperm for Maximum Efficiency", Therio. vol. 52, p. 1323-1341 (1999).

Johnson, L.A., et al., "Enhanced Flow Cytometric Sorting of Mammalian X and Y Sperm: High Speed sorting and Orienting Nozzle for Artificial Insemination", Therio. 49(1): 361 (1988) abstr.

Johnson, L.A., et al., "Flow Sorting of X and Y Chromosome-Bearing Spermatozoa into Two Populations", Gamete Res. 16:203-212. (1987).

Johnson, L.A., et al., "Improved Flow Sorting Resolution of X- and Y-Chromosome Bearing Viable Sperm Separation Using Dual Staining and Dead Cell Gating" Cytometry 17 (suppl 7): 83, (1994).

Johnson, L.A., et al., "Flow Cytometry of X- and Y-Chromosome Bearing Sperm for DNA Using an Improved Preparation Method and Staining with Hoechst 33342." Gamete Research 17: 203-212. (1987).

Johnson, L.A., et al., "Modification of a Laser-Based Flow Cytometer for High-Resolution DNA Analysis of Mammalian Spermatozoa" Cytometry 7, pp. 268-273 (1986).

Joseph, R. L. "Carcass composition and meat quality in once calved heifers." In: J.C. Taylor (Ed.) *The Early Calving of Heifers and its Impact on Beef Production*. 143. (1975).

Joseph, R. L. and J. P. Crowley. "Meat Quality of Once-Calved Heifers." Irish J. Agric. Research 10:281. (1971).

Kachel, V., et al., "Uniform Lateral Orientation, Caused by Flow Forces, of Flat Particles in Flow-Through Systems", The Journal of Histochemistry and Cytochemistry, vol. 25, No. 7, pp. 774-780. (1997).

Kanayama, K., et al., "Pregnancy by Means of Tubal Insemination and Subsequent Spontaneous Pregnancy in Rabbits." J. Int. Med. Res. 20:401-405. (1992).

Karabinus, et al., "Effects of Egg Yolk-Citrate and Milk Extenders on Chromatin Structured Viability of Cryopreserved Bull Sperm", Journal of Dairy Science, vol. 74, No. 11, p. 3836-3848. (1999).

Keeling, P. "A Modeling Study of Once-Bred Heifer Beef Production." Proceedings of the New Zealand Society of Animal Production. 51. (1991).

Kilicarslan, M. R., et al., "Effect of GnRH and hCG on Ovulation and Pregnancy in Mares." Vet. Rec. 139:119-120. (1996).

Kinder, J. E., et al. "Endocrine Basis for Puberty in Heifers and Ewes." J. Repro. and Fertility, p. 393. (1995).

Kinder, J. E., et al., "Endocrine Regulation of Puberty in Cows and Ewes." J. Repro. and Fertility, Suppl. 34:167. (1987).

Kinoshita, Shuichi. "Spectroscopic Properties of Fluorescein in Living Lymphocytes, " Osaka Uinversity Aug. 7, 1986.

Klindt, J. and J. D. Crouse. "Effect of Ovariectomy and Ovariectomy with Ovarian Autotransplantation on Feedlot Performance and Carcass Characteristics of Heifers." J. Anim. Sci. 68:3481. (1990).

Klosterman, E. W. and C. F. Parker. "Effect of Size, Breed and Sex Upon Feed Efficiency in Beef Cattle." North Central Regional Research Publication 235, Ohio Agric. Research and Development Center 1090:3. (1976).

Kniffen, D. M., et al., "Effects of Long-Term Estrogen Implants in Beef Heifers." J. Anim. Sci. 77:2886. (1999).

Kobata, Akira, "Structures and Functions of the Sugar Chains of Human Chorionic Gonadotropin", in *Glycoprotein Hormones* Chin, W.W. and Boime, I., eds. Serono Symposia, Norwell, MA. p. 19-20. 1990.

Koch, R. M., et al., "Characterization of Biological Types of Cattle -Cycle-ll .3." Carcass Composition, Quality and Palatablility. J. Anim. Sci. 49:448. (1919).

Kommisrud E., et al. "Comparison of Two Processing Systems for Bull Semen with Regard to Post-Thaw Motility and Nonreturn Rates." Theriogenology, vol. 45, 1996, pp. 1515-1521.

Lapin, D. R. and Ginther, O. J. "Induction of Ovulation and Multiple Ovulations in Seasonally Anovulatory and Ovulatory Mares with an Equine Pituitary Extract." J. Anim. Sci. 44:834-842. (1977).

Laster, D. B., "Factors Affecting Dystocia and Effects of Dystocia on Subsequent Reproduction in Beef-Cattle." J. Anim. Sci. 36:695. (1973).

Lawrenz, R. "Preliminary Results of Non-Surgical Intrauterine Insemination of Sheep With Thawed Frozen Semen." J S Afr. Vet. Assoc. 56(2): 61-63. (1985).

Levinson, G., et al., "DNA-based X-Enriched Sperm Separation as an Adjunct to Preimplantation Genetic Testing for the Preparation of X-linked Disease." Mol. Human Reprod. 10:979-982. (1995).

Lightwave Electronics, "Xcyte," www.LightwaveElectronics.com.

Lindsey, A. C., et al., "Low Dose Insemination of Mares Using Non-Sorted and Sex-Sorted Sperm" Animal Reproduction Science 68 p. 279-89 (2001).

Lindsey, A., et al., "Hysteroscopic Insemination of Mares with Nonfrozen Low-dose Unsexed or Sex-sorted Spermatozoa", pp. 1-15 currently unpublished.

Linge, F. "Faltforsok med djupfrost sperma (Field Trials With Frozen Sperm)." Farskotsel. 52:12-13. (1972).

Liu, Z, et al. "Survival of Bull Sperm Frozen at Different rates in Media Varying in Osmolarity." Cryobiology, vol. 27, 1998, pp. 219-230.

Loy, R. G. and Hughes, J.P. "The Effects of Human Chorionic Gonadotropin on Ovulation, Length of Estrus, and Fertility in the Mare." Cornell Vet. 56:41-50 (1965).

Lynch, I. M., et al., "Influence of timing of gain on growth and reproductive performance of beef replacement heifers." J. Anim. Sci. 75:1715. (1997).

Macmillan, K. L. and Day, A.M., "Prostaglandin F2a: A Fertility Drug In Dairy Cattle?", Animal Research Station, Private Bag, Hamilton, New Zealand, Therio. vol. 18, No. 3, p. 245-253 (1982).

Manni, Jeff. "To-Photon Excitation Expands the Capabilities of Laser-Scanning Microscopy,".

Manning, S. T., et al., "Development of Hysteroscopic Insemination of the Uterine Tube in the Mare", Proceedings of the Annual Meeting of the Society for Theriogenology, 1998, p. 84-85.

Martin, A. H., et al., "Characteristics of Youthful Beef Carcasses in Relation to Weight, Age and Sex. lll. Meat Quality Attributes." Canadian J. Anim. Sci. 51:305. (1971).

Martin, L. C., et al., "Genetic-effects on Beef Heifer Puberty and Subsequent Reproduction." J. Anim. Sci. 70:4006. (1992).

Martinez, E. A., et al., "Successful Low-Dose Insemination by a Fiberoptic Endoscope Technique in the Sow", Proceedings Annual Conference of the International Embryo Transfer Society, Netherlands, Therio. vol. 53 p. 201, Jan. 2000.

Matsuda, Y. and Tobari, I. "Chromosomal Analysis in Mouse Eggs Fertilized In Vitro With Sperm Exposed to Ultraviolet Light (UV) and Methyl and Ethyl Methanesulfonate (MMS and EMS)." Mutat. Res. 198:131-144. (1988).

Matulis, R. J., "Growth and carcass characteristics of cull cows after different times-on-feed." J. Anim. Sci. 65:669. (1987).

Mauleon, P. "Recent research related to the physiology of puberty. "In: J.C. Taylor (ed.) *The Early Calving of Heifers and its Impact on Beef Production.* (1975).

Maxwell, W. and Johnson, L., "Chlortetracycline Analysis of Boar Spermatozoa After Incubation, Flow Cytometric Sorting, Cooling, or Cryopreservation", Molecular Reproduction and Development 46, p. 408-418. (1997).

Maxwell, W. M. C., et al., "Fertility of Superovulated Ewes After Intrauterine or Oviductal Insemination with Low Numbers of Fresh or Frozen-Thawed Spermatozoa." Reprod. Fertil. Dev. 5:57-63. (1993).

Maxwell, W. M. C., et al., "The Relationship Between Membrane Status and Fertility of Boar Spermatozoa After Flow Cytometric Sorting in the Presence or Absence of Seminal Plasma" Reprod. Fertil. Dev. vol. 10 p. 433-40 (1998).

Maxwell, W. M. C., et al., "Viability and Membrane Integrity of Spermazota after Dilution and Flow Cytometric Sorting in the Presence or Absence of Seminal Plasma." Reprod. Fertil. Dev. 8:1165-78. (1997).

McCormick, R. J. "The Flexibility of the Collagen Compartment of Muscle." Meat Sci. 36:79. (1994).

McCue, P.M. "Superovulation" Vet. Clin. N. Amer. Eq. Prac. 12:1-11. (1996).

McCue, P.M., et al., "Oviductal insemination in the mare." 7th Internat. Symp. Eq. Reprod. 133 (1997) abstr.

McDonald, L. E. "Hormones of the Pituitary Gland." Veterinary Pharmacology and Therapeutics. 6th ed. Edited by N. H. Booth and L. E. McDonald. Ames, Iowa State Univ. Press. p. 590 (1988).

McKenna, T. et al., "Nonreturn Rates of Dairy Cattle Following Uterine Body or Cornual Insemination." J. Dairy Sci. 73:1179-1783 (1990).

McKinnon, A.O. and Voss, J. L. *Equine Reproduction*. Lea and Febiger. Philadelphia, London (1993).

McKinnon, A.O., et al., "Predictable Ovulation in Mares Treated With an Implant of the GnRH Analogue Deslorelin." Eq. Vet. J. 25:321-323. (1993).

McKinnon, A.O., et al., "Repeated Use of a GnRH Analogue Deslorelin (Ovuplant) for Hastening Ovulation in the Transitional Mare." Eq. Vet. J. 29:153-155. (1996).

McLeod, John H., "The Axicon: A New type of Optical Element", Journal of the Optical Society of America, vol. 44 No. 8, Aug. 1954, Eastman Kodak Company, Hawk-Eye Works, Rochester, New York.

Meilgaard, M., et al., "Sensor Evaluation Techniques." CRC Press Inc., Boca Raton, FL. (1991).

Meinert, C., et al., "Advancing the Time of Ovulation in the Mare With a Short-Term Implant Releasing the GnRH Analogue Deslorelin", Equine Veterinary Journal, 25, p. 65-68 (1993).

Mendes Jr., J.O.B. "Effect of heparin on cleavage rates and embryo production with four bovine sperm preparation protocols" Theriogenology 60 (2003) 331-340.

Menke,E. A Volume Activated Cell Sorter Journal of Histo chemistry and Cyto Chemistry, 1977, vol. 25,No. 7, pp. 796-803.

Merton, J., et al., "Effect of Flow Cytometrically Sorted Frozen/Thawed Semen on Success Rate of In Vitro Bovine Embryo Production", Therio. 47, p. 295. (1997)

Metezeau P. et al. Improvement of Flow Cytometry Analysis and Sorting of Bull Spermatozoa by Optical Monitoring of Cell Orientation as Evaluated by DAN Specific Probing Molecular Reproduction and Development, 1991,vol. 30 pp. 250-257.

Meyers, P. J., et al., "Use of the GnRH Analogue, Deslorelin Acetate, in a Slow Release Implant to Accelerate Ovulation in Oestrous Mares." Vet. Rec. 140:249-252. (1997).

Michaels, C., "Beef A. I. Facilities That Work", Proc. Fifth N.A.A.B Tech. Conf. A. I. Reprod. Columbia, MO. pp. 20-22.

Michel, T. H., et al., "Efficacy of Human Chorionic Gonadotropin and Gonadotropin Releasing Hormone for Hastening Ovulation in Thoroughbred Mares." Eq. Vet. J. 6:438-442. (1986).

Miller, S. J. "Artificial Breeding Techniques in Sheep." Morrow, D.A. (ed: Current Therapy in Therio 2. Philadelphia, WB Saunders. (1986).

Mirskaja, L. M. and Petropavloskii, V.V. "The Reduction of Normal Duration of Heat in the Mare by the Administration of Prolan." Probl. Zivotn. Anim. Breed. Abstr. 5:387. (1937).

Moe, P. W., "Energetics of Body Tissue Mobilization." J. of Dairy Sci. 54:548.

Molinia, F. C., et al., "Successful Fertilization After Superovulation and Laparoscopic Intrauterine Insemination of the Brushtail Possum Trichosurus vulpecula, and Tammar Wallaby, Macropus eugenii." J. Reprod. Fertil. 112:9-17. (1998).

Moran, C., et al., "Puberty in Heifers -a Review." Animal Reproduction Sci. 18:167. (1989).

Moran, D. M. et al., "Determination of Temperature and Cooling Rate Which Induce Cold Shock in Stallion Spermatozoa", Therio. vol. 38 p. 999-1012 (1992).

Morcom, C. B. and Dukelow, W.R. "A Research Technique for the Oviductal Insemination of Pigs Using Laparoscopy." Lab. Anim. Sci. p. 1030-1031. (1980).

Morgan, J. B., et al., "National Beef Tenderness Survey." J. Anim. Sci. 69: 3274. (1991).

Morris, L. H., et al., "Hysteroscopic Insemination of Small Numbers of Spermatozoa at the Uterotubal Junction of Preovulatory Mares", Journal of Reproduction and Fertility, vol. 118, pp. 95-100 (2000).

Morris, S. T., et al., "Biological efficiency: How relevant is this concept to beef cows in a mixed livestock seasonal pasture supply context?" Proceedings of the New Zealand Society of Animal Production 54:333. (1994).

Moseley, W. M., et al., "Relationship of Growth and Puberty in Beef Heifers Fed Monensin" J. Anim. Sci. vol. 55 No. 2 p. 357-62 (1982).

Mount, D. E. "Fibrous and Non-fibrous Carbohydrate Supplementation to Ruminants Grazing Forage From Small Grain Crops." M.S. Thesis. Abstr. Colorado State University. (2000).

Muller, W. and Gautier, F. "Interactions of Heteroaromatic Compounds with Nucleic Acids." Euro. J Biochem. 54:358. (1975).

Mullis, K. B. and F. A. Faloona, "Specific Synthesis of DNA in Vitro Via a Polymerase-Catalyzed Chain Reaction" Methods in Enzymology vol. 155 p. 335-350 (1978).

Munne, S. "Flow Cytometry Separation of X and Y Spermatozoa Could be Detrimental to Human Embryos", Hum. Reprod. 9(5): 758 (1994).

Myers, S. E., "Performance and Carcass Traits of Early-Weaned Steers Receiving Either a Pasture Growing Period or a Finishing Diet at Weaning." J. Anim. Sci. 77:311. (1999).

Myers, S. E., et al., "Comparison of Three Weaning Ages on Cow-Calf Performance and Steer Carcass Traits." J. Anim. Sci. 77:323. (1999).

Myers, S. E., et al., "Production Systems Comparing Early Weaning to Normal Weaning With or Without Creep Feeding for Beef Steers." J. Anim. Sci. 77:300. (1999).

Nix, J. P., et al., "Serum Testosterone Concentration, Efficiency of Estrus Detection and Libido Expression in Androgenized Beef Cows." Therio. 49: 1195. (1998).

Nowshari, et al., "Superovulation of Goats with Purified pFSH Supplemented with Defined Amounts of pLH", Therio. vol. 43, p. 797-802 (1995).

NRC. "Nutrient Requirements for Beef Cattle." National Academy of Sci. National Research Council, Washington, DC. (1996).

O'Brien, Justine K. et al., "Preliminary Developments of Sperm Sorting Technology in Non-human Primates", Biology of Reproduction 2001 (Su;;. 1) 64:158.

Olive, M.D., "Detection of Enterotoxigenic Escherichia coli after Polymerase Chain Reaction Amplification with a Tehrmostable DNA Polymerase", J of Clinical Microbiology, Feb. 1989 p. 261-265.

Olson, S.E. and Seidel, G. E. Jr., "Reduced Oxygen Tension and EDTA improve Bovine Zygote Development in a Chemically Defined Medium", J. of Anim. Sci. 78, pp. 152-157. (2000).

Owen, J. B. "The Maiden Female-A Means of Increasing Meat Production." Proc. Symp. On the Use of Once Bred Heifers and Gilts. (1973).

Ozhin F.V. et al. Artificial insemination of farm animals. Moscow, Izdatelstvo Selskokhozyaastvennoi Literatury, 1961, pp. 350-361 and pp. 380-393.

Pace, M. M. and Sullivan, J. J. "Effect of Timing of Insemination, Numbers of Spermatozoa and Extender Components on Pregnancy Rates in Mares Inseminated with Frozen Stallion Semen." J. Reprod. Fertil. Suppl. 23:115-121.

Parrish, J. J., et al., "Capacitation of Bovine Sperm by Heparin", Department of Meat and Animal Science, Biology Of Reproduction 38, p. 1171-1180 (1988).

Patterson, D. J., et al., "Estrus Synchronization with an Oral Progestogen Prior to Superovulation of Postpartum Beef Cows" Therio. 48, 1025-33 (1997).

Peippo, J., et al., "Sex Diagnosis of Equine Preimplantation Embryos Using the Polymerase Chain Reaction", Therio. vol. 44:619-627 (1995).

Penfold, L.M.et at., "Comparative Motility of X and Y Chromosome-Bearing Bovine Sperm Separated on the Basis of DNA Content", Mol. Reprod. And Develop. 1998, vol. 50,pp. 323-327.

Perry, E. J., "Historical Background" The Artificial Insemination of Farm Animals. 4th ed. E. J. Perry (ed.) New Brunswick, Rutgers University Press, pp. 3-12. (1968).

Petersen, G. A., et al, "Cow and Calf Performance and Economic-Considerations of Early Weaning of Fall-Born Beef Claves", J. Anim. Sci., 64:15, pp. 15-22. (1987).

Petit, M. "Early Calving in Suckling Herds." In: J.C. Taylor (ed.) *The Early Calving of Heifers and its Impact on Beef Production*. p. 157-176. (1975).

Picket B.W., et al., "Livestock Production Science," 1998.

Pickett, B. W, et al., "Factors Influencing the Fertility of Stallion Spermatozoa in an A. I. Program." Proc. 8th International Congress Anim. Reprod. A. I. Krakow, Poland. 4:1049-1052. (1976).

Pickett, B. W., et al., "Effect of Seminal Extenders on Equine Fertility." J. Anim. Sci. 40:1136-1143. (1975).

Pickett, B. W., et al., "Influence of Seminal Additives and Packaging Systems on Fertility of Bovine Spermatozoa." J. Anim. Sci. Suppl. ll. 47:12. (1978).

Pickett, B. W., et al., "Management of the Mare for Maximum Reproductive Efficiency." CSU Anim. Repro. Lab. Bull. No. 06. Fort Collins CO. (1989).

Pickett, B. W., et al., "Procedures for Preparation, Collection, Evaluation and Insemination of Stallion Semen." CSU Exp. Sta. Artira. Reprod. Lab. Gen. Series Bull. 935. (1973).

Pickett, B. W., et al., "Recent Developments in Artificial Insemination in Horses", Livestock Production Science, 40, p. 31-36 (1994).

Pickett, B. W., et al., "The Effect of Extenders, Spermatozoal Numbers and Rectal Palpation on Equine Fertility." Proc. Fifth N.A.A.B Tech. Conf. A. I. Reprod. Columbia, MO. pp. 20-22. (1974).

Pinkel et al., "Flow Chambers and Sample Handling", Flow Cytometry: Instrumentation and Data Analysis, Van Dilla et al. (Eds.), 1985, pp. 77-128.

Pinkel, D., et al, "Flow Cytometric Determination of the Proportions of X- and Y- Chromosome-Bearing Sperm in Samples of Purportedly Separated Bull Sperm", J. of Anim. Sci., vol. 60, p. 1303-1307 (1998).

Pinkel, D., et al., "High Resolution DNA Content Measurements of Mammalian Sperm", Cytometry 3:1-9. (1982).

Pinkel, D., et al., "Sex Preselection in Mammals? Separation of Sperm Bearing the Y and "O" Chromosomes in the Vole Microtus Oregoni", Science vol. 218 p. 904 (1982).

Piston, D.W. "Three-dimensionally resolved NAD(P)H cellular metabolic redox imaging of the in situ cornea with two-photon excitation laser scanning microscopy," Journal of Microscopy, vol. 178, Nov. 29, 1994.

Polge, E. J., "Historical Perspective of AI: Commercial Methods of Producing Sex Specific Semen, IVF Procedures", Proceedings of the 16th Technical Conference on Artificial Insemination & Reproduction, Cambridge, England, pp. 7-11. (1996).

Polge, et al, "Revival of Spermatozoa After Vitrification and Dehydration at Low Temperatures", Nature, 164:666 (1994).

Preza, C. et al, "Determination of Direction-Independent Optical Path-Length Distribution of Cells Using Rotational-Diversity Transmitted-Light Differential Interference Contrast (DIC) Images", Presented at the Multidimensional Microscopy: Image Acquisition and Processing V, p. 1-11 (1998).

Prokofiev M.I. Regoulyatsia Razmnozhenia Selskokhozyastvennykh Zhivotnykh, Leningrad, NAOUKA Publishing House, 1983, pp. 181-195.

Province, C.A., et al., Cooling Rates, Storage, Temperatures and Fertility of Extended Equine Spermatozoa Therio. vol. 23 (6) p. 925-934, Jun. 1985.

Pursel, et al, "Effect of Orvus ES Paste on Acrosome Morphology, Motility and Fertilizing Capacity of Frozen-Thawed Boar Sperm," Journal of Animal Science, 47:1:198-202 (1978).

Purvis, H. T. and J. C. Whittier. "Effects of Ionophore Feeding and Anthelmintic Administration on Age and Weight at Puberty in Spring-Born Beef Heifers." J. Anim. Sci. 74:736-744. (1996).

Randel, R. D. "Nutrition and Postpartum Rebreeding in Cattle." J. Anim. Sci. 68:853. (1990).

Rath, D., et al., "Low Dose Insemination Technique in the Pig", Boar Semen Preservation IV, p. 115 118. (2000).

Rath, D., et al., "Production of Piglets Preselected for Sex Following in Vitro Fertilization with X and Y Chromosome-Bearing Spermatozoa Sorted by Flow Cytometry", Therio. 47, p. 795-800 (1997).

Rathi, R. et al., "Evaluation of In Vitro Capacitation of Stallion Spermatoza", Biology of Reproduction 2001,vol. 65, pp. 462-470.

Recktenwald, Diether. "Cell Separation Methods and Applications," New York 1997.

Reiling, B.A., et al., "Effect of Prenatal Androgenization on Performance, Location, and Carcass and Sensory Traits on Heifers in Single Calf Heifer System", J. Anim. Sci., 1995, 73: 986, p. 986-992.

Reiling, B.A., et al., "Effects of Prenatal Androgenization and Lactation on Adipose Tissue Metabolism in Finishing Single-Calf Heifers" J. Anim. Sci. vol. 75 p. 1504-1512 (1997).

Reiling, B.A., et al., "Effects of prenatal Androgenization, Melengestrol Acetate, and Synovex-H on Feedlot Performance, Carcass, and Sensory Traits of Once-Calved Heifers" J. Anim. Sci. vol. 74 p. 2043-51 (199).

Rens, W., et al., "A Novel Nozzle for More Efficient Sperm Orientation to Improve Sorting Efficiency of X and Y Chromosome-Bearing Sperm", Technical Notes, Cytometry 33, p. 476-481 (1998).

Rens, W., et al., "Improved Flow Cytometric Sorting of X- and Y-Chromosome Bearing Sperm: Substantial Increase in Yield of Sexed Semen", Molecular Reproduction and Development, p. 50-56(1999).

Rigby, S. L., et al., "Pregnancy Rates in Mares Following Hysterscopic or Rectally-Guided Utero-Tubal insemination with Low Sperm Numbers" Abstracts/Animal Reproduction Science vol. 68 p. 331-333 (2001).

Riggs, B.A. "Integration of Early Weaning and Use of Sexed Semen in a Single-Calf Heifer System to Increase Value of Non-Replacement Heifers" MS Thesis, Colorado State University, Spring 2000.

Ritar, A. and Ball, A., "Fertility of Young Cashmere Goats After Laparoscopic Insemination." J. Agr. Sci. 117: p. 271-273. (1991).

Roberts, J. R., Veterinary Obstetrics and Genital Diseases. Ithaca, New York. p. 740-749. (1971).

Romero-Arredondo, A. "Effects of Bovine Folicular Fluid on Maturation of Bovine Oocytes" Theriogenology 41: 383-394, 1994.

Romero-Arrendondo, A. "Effects of Follicular Fluid dring In Virto Maturation of Bovine Oocytes on In Vitro Fertilization and Early Embryonic Development" Biology of Reproduction 55, 1012-1016 1996.

Romita, A. "Some Considerations on the Beef Situation in Italy." In: J.C. Taylor (ed.) *The Early Calving of Heifers and its Impact on Beef Production.* 23. (1975).

Roser, J. F., et al., "Reproductive Efficiency in Mares With Anti-hCG Antibodies." Proc 9th Int. Congr. Anim. Repro. and A. I. 4:627 (1980) abstr.

Roth, T. L., et al., "Effects of Equine Chorionic Gonadotropin, Human Chorionic Gonadotropin, and Laparoscopic Artificial Insemination on Embryo, Endocrine, and Luteal Characteristics in the Domestic Cat." Bio. Reprod. 57:165-171 (1997).

Roux, M., et al., "Early Calving Heifers Versus Maiden Heifers for Beef-Production from Dairy herds. I. The Effects of Genotype (Friesian and Carloads x Friesian) and Two Feeding Levels in the Rearing Period on Growth and Carcass Quality." Livestock Prod. Sci. 16:1 (1987).

Rowley, H. S., et al., "Effect of Insemination Volume on Embryo Recovery in Mares." J. Equine Vet. Sci. 10:298-300 (1990).

Roy, J. H., "Rearing Dairy-Herd Replacements." Journal of the Society Of Dairy Technology 31:73-79 (1978).

Rutter, L. M., et al., "Effect of Abomasal Infusion of Propionate on the GnRH-Induced Luteinizing Hormone Release in Prepuberal Heifers." J. Anim. Sci. 56:1167 (1983).

Salamon, S., *Artificial Insemination of Sheep*, Chippendale, New South Whales. Publicity Press. p. 83-84 (1976).

Salisbury, G. W. and VanDemark, N. L. "Physiology of Reproduction and Artificial Insemination of Cattle." San Francisco: Freeman and Company. p. 442-551 (1978) (1961 & 1978 COMBINED) Chapters 16 and 17 are the complete article.

Schenk, J. L. "Applying Semen Sexing Technology to the AI Industry", Proceedings of the 18th Technical Conference on Artificial insemination & Reproduction, 2000.

Schenk, J. L, et al., "Imminent Commercialization of Sexed Bovine Sperm", Proceedings, The Range Beef Cow Symposium XVL, p. 89-96 (1999).

Schenk, J. L., "Cryopreservation of Flow-Sorted Bovine Spermatozoa", Therio. vol. 52, 1375-1391 (1999).

Schiewe, M. C., et al., "Transferable Embryo Recovery Rates Following Different Insemination Schedules in Superovulated Beef Cattle" Therio. 28 (4) Oct. 1997, pp. 395-406.

Schillo, K. K., et al, "Effects of Nutrition and Season on the Onset of Puberty in the Beef Heifer." J. Anim. Sci. 70:3994 (1992).

Schmid, R. L., et al, "Fertilization with Sexed Equine Spermatozoa Using Intracytoplasmic Sperm Injection and Oviductal Insemination ", 7th International Symposium On Equine Reproduction, pp. 139 (1998) abstr.

Schnell, T. D., et al, "Performance, Carcass, and Palatability Traits for Cull Cows Fed High-Energy Concentrate Diets for 0, 14, 28, 42, or 56 days." J. Anim. Sci. 75:1195. (1997).

Schoonmaker, J. P., et al., "Effects of Age at Weaning and Implant Strategy on Growth of Steer Calves." J. Anim. Sci. (Supppl. II) 76:71. (1998) abstr.

Seidel, G. E. Jr. " Cryopreservation of Equine Embryos" Veterinary Cliniics of North America: Equine Practice vol. 12, No. 1, Apr. 1996.

Seidel, G. E. Jr. "Sexing Bovine Sperm" The AABP Proceedings - vol. 34.

Seidel, G. E. Jr. Sexing mammalian spermatozoa and embryos-state of the art Journal of Reproduction and Fertility Supp 54, 477-487 1999.

Seidel, G. E. Jr. "Uterine Horn Insemination of Heifers With Very Low Numbers of Nonfrozen and Sexed Spermatozoa", Atlantic Breeders Cooperative, Therio. 48: pp. 1255-1264, (1997).

Seidel, G. E. Jr et al., "Current Status of Sexing Mammalian Spermatozoa," Society for Reproduction and fertiity, pp. 733-743, 2002.

Seidel, G. E. Jr., "Commercilizing Reproductive Biotechnology—The Approach used by XY, Inc.," Theriogenology, p. 5, 1999.

Seidel, G. E. Jr. et al., "Insemination of Heifers with Sexed Sperm", Therio, vol. 52, pp. 1407-1421 (1999).

Seidel, G. E. Jr., "Artificial Insemination With X-and Y-Bearing Bovine Sperm", Animal Reproduction and Biotechnology Laboratory, Colorado State University, (1996).

Seidel, G. E. Jr., "Status of Sexing Semen for Beef Cattle", Texas A & M University 45th Annual Beef Cattle Short Course and Trade Show Proceedings, Aug. 9-11, p. lll24-lll27, (1999).

Seidel, G. E. Jr., et al, "Insemination Of Heifers With Very Low Numbers Of Frozen Spermatozoa", CSU, Atlantic Breeders Cooperative, Lancaster, PA, DUO Dairy, Loveland, CO, Jul. (1996).

Seidel, G. E. Jr., et al, "Insemination of Holstein Heifers With Very Low Numbers Of Unfrozen Spermatozoa", CSU, Atlantic Breeders Cooperative, (1995).

Seidel, G. E. Jr., et al, "Sexing Mammalian Sperm—Overview", Therio. 52: 1267-1272, (1999).

Seidel, G. E. Jr., et al., "Artificial Insemination of Heifers with Cooled, Unfrozen Sexed Semen", Therio, vol. 49 pp. 365 (1998) abstr.

Seidel, G. E. Jr., et al., "Insemination of Heifers with Sexed Frozen or Sexed Liquid Semen." Therio. 51. (in press) (1999) abstr.

Seidel, G. E. Jr., Economics of Selecting for Sex: The Most Important Genetic Trait, Theriogenology 59, (2003), pp. 585-598.

Sell, R. S., et al., "Single-calf Heifer Profitability Compared to Other North Dakota Beef Production Systems," Department of Ag. Eco., North Dakota State University, Ag. Econ. Rpt. 20.

Senger, P. L., et al., "Influence of Cornual Insemination on Conception in Dairy Cattle." J Anim. Sci. 66:3010-3016. (1988).

Shabpareh, V. "Methods for Collecting and Maturing Equine Oocytes in Virto" Theriogenology 40: 1161-1175, 1993.

Shackelford, S. D., et al, "Effects of Slaughter Age on Meat Tenderness and USDA Carcass Maturity Scores of Beef Females." J. Anim. Sci. 73:3304. (1995).

Shapiro, Howard M. MD., PC. "Practical Flow Cytometry Third Edition," New York 1994.

Sharpe, J.C., et al., "A New Optical Configuration for Flow Cytometric Sorting of Aspherical Cells" Horticulture and Food Research Institute of New Zealand Ltd., Hamilton, New Zealand (PNS) Nov. 2, 1997 Abstract.

Sharpe, Johnathan, Thesis; "An Introduction of Flow Cytometry", Ch. 2-2.2, 1997.

Sharpe, Johnathan, Thesis; "Gender Preselection-Principle Scientific Options," Ch. 3.4-3.4.8, 1997.

Sharpe, Johnathan, Thesis; "Sperm Sexing using Flow Cytometry," Ch. 3.5-3.5.8, 1997.

Sharpe, Johnathan, Thesis; "Sperm Sexing-Method of Johnson et al," Ch. 3.6-4.3.4, 1997.

Shelton, J. N. and Moore, N.W. "The Response of the Ewe to Pregnant Serum Mare Gonadotropin and to Horse Anterior Pituitary Extract." J. Reprod. Fertil. 14:175-177. (1967).

Shilova, A. V., et al., "The Use of Human Chorionic Gonadotropin for Ovulation Date Regulation in Mares." Vlllth Int. Congress On Anim. Repro. and A. I. 204-208. (1976).

Shorthose, W. R. and P. V. Harris. "Effect of Animal Age on the Tenderness of Selected Beef Muscles." J. Food Sci. 55:1-. (1990).

Silbermann, M., "Hormones and Cartilage. Cartilage: Development, Differentiation, and Growth." pp. 327-368. Academic Press, Inc. (1983).

Simon, M., "The Effect of Management Option on the Performance of Pregnant Feedlot Heifers." M.S. Thesis. Kansas State University. (1983).

Skogen-Hagenson, M. J. et al; "A High Efficiency Flow Cytometer," The Journal of Histochemistry and Cytochemistry, vol. 25, No. 7, pp. 784-789, 1977, USA.

Smith, G. C., et al, "USDA Maturity Indexes and Palatability of Beef Rib Steaks." J. of Food Quality 11:1. (1988).

Smith, G. C., et al., "Relationship of USDA Maturity Groups to Palatability of Cooked Beef." J. of Food Sci. 47:1100. (1982).

Smith, R. L., et al, Influence of Percent Egg Yolk during Cooling and Freezing on Survival of Bovine.

Solsberry G.U., Van-Denmark N.L., Theory and practice of artificial cow insemination in USA, Moscow, KOLOS Publishing House, 1966, p. 346.

Spectra Physics, The Solid State Laser Company, "Vangaurd 4 Watts of UV from a Quasi-CW, All Solid State Laser," http://www.splasers.com/products/isl_products/vangaurd.html three pages, printed Nov. 14, 2002.

Spectra-Physics Products, "Fcbar" http://www.splasers.com/products/oem_products/ov_fcbar.html two pages printed Nov. 14, 2002.

Spectra-Physics, The Solid State Laser Company, Vanguard 2000-HMD 532, www.specra-physics.com.

Spectra-Physics, The Solid State Laser Company, Vanguard 350-HMD 355, www.specra-physics.com Squires, E. L, et al., "Effect of Dose of GnRH Analog on Ovulation in Mares." Therio. 41:757-769. (1994).

Squires, E. L, "Simultaneous Analysis of Multiple Sperm Attributes by Flow Cytometry", Diagnostic Techniques and Assisted Reproductive Technology, The Veterinary Clinics of North America, Equine Practice, vol. 12, No. 1, p. 127-130 (1996).

Squires, E. L., "Early Embryonic Loss" *Equine Diagnostic Ultrasonography*, first ed., Rantanen & McKinnon. Williams and Wilkins, Baltimore, Maryland, p. 157-163 (1998).

Squires, E. L., et al, "Cooled and Frozen Stallion Semen", Bulletin No. 9, Colorado State University, Ft. Collins, CO. (1999).

Squires, E.L., "Procedures for Handling Frozen Equine Semen for Maximum Reproductive Efficiency", pp. 1, 39-41, 81-89.

Staigmiller, R.B. "Superovulation of Cattle with Equine Pituitary Extract and Porcine FSH" Theriogenology 37: 1091-1099 1992.

Stap J. Et al Improving the Resolution of Cryopreserved X- and Y-Sperm During DNA Flow Cytometric Analysis with the Addition to Percoll to quench the Fluorescence of Dead Sperm: Academic Medical Center, University of Amsterdam (1998) Journal of Animal Science vol. 76 1998, pp. 1896-1902.

Steel, N. L., "Cost Effectiveness of Utilizing Sexed-Semen in a Commercial Beef Cow Operation", MS Thesis, Colorado State University, Summer 1998.

Steinkamp: "Flow Cytometry" vol. 55, No. 9, Sep. 1984 pp. 1375-1400, New York Review of Scientific Instruments Abstract Only.

Stellflug, J. N., "Plasma Estrogens in Periparturient Cow." Therio 10:269. (1978).

Stevenson, J. S., et al., "Detection of Estrus by Visual Observation and Radiotelemetry in Peripubertal, Estrus-Synchronized Beef Heifers." J. Anim. Sci. 74:729. (1996).

Story, C. E., et al., "Age of Calf at Weaning of Spring-Calving Beef Cows and the Effect on Cow and Calf Performance and Production Economics." J. Anim. Sci. 78:1403. (2000).

Stovel R.T. A Means for Orienting Flat Cells in flow systems Biophysical Journal, 1978, vol. 23, pp. 1-5.

Sullivan, J. J., et al., "Duration of Estrus and Ovulation Time in Nonlactating Mares Given Human Chorionic Gonadotropin During Three Successive Estrous Periods." J.A.V.M.A. 162:895-898. (1973).

Sumner, A. T. and Robinson, J. A., "A Difference in Dry Mass Between the Heads of X and Y- Bearing Human Spermatozoa", J Reprod Fertil. 48, p. 9-15 (1976).

Swanson, E. W. "Future Research on Problems of Increasing Meat Production by Early Calving." In: J.C. Taylor (ed.) *The Early Calving of Heifers and its Impact on Beef Production*. (1975).

Swenson, S. L., et al., "PRRS Virus Infection in Boars: Isolation From Semen and Effect on Semen Quality" from the 1995 Research Investment Report, Iowa State University, Veterinary Clinical Sciences, Iowa State University.

Taljaard, T. L., et al., "The Effect of the Laparoscopic Insemination Technique on the Oestrus Cycle of the Ewe." J. South Afr. Vet. Assoc. 62(2): 60-61. (1991).

Tatum, J. D., et al., "Carcass Characteristics, Time on Feed and Cooked Beef Palatability Attributes." J. Anim. Sci. 50:833. (1980).

Taylor, C. S., "Efficiency of Food Utilization in Traditional and Sex-Controlled Systems of Beef Production", AFRC Animal Breeding Research Organization, West Mains Road, Edinburg EH9 3JQ, pp. 401-440.

Tervit, H.R., et al., "Successful Culture In Vitro of Sheep and Cattle Ova", Agriculutural Research Council, Unit of Reprod. Physio. and Biochem., Univ of Cambridge, p. 493-497 (1972).

Thun, Rico, et al., Comparison of Biociphos-Plus® and TRIS-Egg Yolk Extender for Cryopreservation of Bull Semen; Theriogenology Symposium, Dec. 1999, vol. 52, #8.

*Time-Bandwidth Products "GE—100—XHP"*, www.tbsp.com, 2 pages, Jan. 2002.

Unruh, J. A. "Effects of Endogenous and Exogenous Growth-Promoting Compounds on Carcass Composition, Meat Quality and Meat Nutritional-Value." J. Anim. Sci. 62:1441. (1986).

USDA "Official United States Standards for Grades of Carcass Beef." Agric, Marketing Serv., USDA, Washington, DC. (1997).

Van Dilla, Martin, "Overview of Flow Cytometry: Instrumentation and Data Analysis", Flow Cytometry: Instrumentation and Data Analysis, Van Dilla et al. (Eds.), 1985, pp. 1-8.

Van Munster, E. B., "Geslachtsbepaling met interferometrie", Derde prijs NtvN-prijsvraag voor pas-gepromoveerden 65/4, (Sex Determination with Interferometry) p. 95-98 (1999).

Van Munster, E. B., et al, "Difference in Sperm Head Volume as a Theoretical Basis for Sorting X & Y-Bearing Spermatozoa: Potentials and Limitations", Therio 52, pp. 1281-1293 (1999).

Van Munster, E. B., et al, "Difference in Volume of X- and Y-chromosome Bearing Bovine Sperm Heads Matches Difference in DNA Content" Cytometry vol. 35 p. 125-128 (1999).

Van Munster, E. B., et al, "Measurement-Based Evaluation of Optical Path Length Distributions Reconstructed From Simulated Differential Interference Contrast Images", J of Microscopy 191, Pt. 2, p. 170-176 (1998).

Van Munster, E. B., et al, "Reconstruction of Optical Pathlength Distributions From Images Obtained by a Wide Field Differential Interference Contrast Microscope", J of Microscopy 188, Pt. 2, p. 149-157 (1997).

Vazquez, J. J. et al., "Nonsurgical Uterotubal Insemination in the Mare", Proceedings of the 44th Annual Convention of the American Association of Equine Practitioners, vol. 44, pp. 68-69 (1998).

Vazquez, J. M., et al., "A. I. in Swine; New Strategy for Deep Insemination with Low Number of Spermatozoa Using a Non-surgical Methodology", 14th International Congress on Animal Reproduction, vol. 2, Stockholm, Jul. 2000, p. 289.

Vazquez, J., et al., "Development of a Non-surgical Deep Intra Uterine Insemination Technique", Boar Semen Preservation IV, IVth International Conference on Boar Semen Preservation, Maryland, pp. 262-263.

Vazquez, J., et al., "Hyposmotic Swelling Test as Predictor of the Membrane Integrity in Boar Spermatozoa", Boar Semen Preservation IV, IVth International Conference on Boar Semen Preservation, Maryland, pp. 263.

Vazquez, J., et al., "Successful low dose insemination by a fiber optic Endoscope technique in the Sow", Proceedings Annual Conference of the International Embryo Transfer Society, Netherlands, Theriogenology, vol. 53 Jan. 2000.

Vidament, M., et al., "Equine Frozen Semen Freezability and Fertility Field Results." Therio. 48:907. (1997).

Vincent, B.C., et al, "Carcass Characteristics and Meat Quality of Once-Calved Heifers." Canadian J. Anim. Sci. 71:311. (1991).

Vogel, T., et al, "Organization and Expression of Bovine TSPY", Mammalian Genome, vol. 8, pp. 491-496 (1997).

Voss, J. L. and Pickett, B. W., "Reproductive Management of the Broodmare." CSU Exp. Sta. Anim. Reprod. Lab. Gen. Series. Bull. 961. (1976).

Voss, J. L., et al., "Effect of Number and Frequency of Inseminations on Fertility in Mares." J. Reprod. Fertil. Suppl. 32:53-57. (1982).

Voss, J. L., et al., Effect of Human Chorionic Gonadotropin on Duration of Estrous Cycle and Fertility of Normally Cycling, Nonlactating Mares. J.A.V.M.A. 165:704-706. (1974).

Waggoner, A. W., et al., "Performance, Carcass, Cartilage Calcium, Sensory and Collagen Traits of Longissimus Muscles of Open Versus 30-month-old Heifers That Produced One Calf." J. Anim. Sci. 68:2380. 1990.

Watson, "Recent Developments and Concepts in the Cryopreservation of Spermatozoa and the Assessment of Their Post-Thawing Function," Reprod. Fertil. Dev. 7:871-891 (1995) ABSTRACT.

Welch G., et al., Fluidic and Optical Modifications to a FACS IV for Flow Sorting of X- and Y-Chromosome Bearing Sperm Based on DNA. Cytometry 17 (Suppl. 7): 74. (1994).

Welch, G., et al., "Flow Cytometric Sperm Sorting and PCR to Confirm Separation of X- and Y-Chromosome Bearing Bovine Sperm", Animal Biotechnology, 6, pp. 131-139 (1995).

Wheeler, T. L., et al., "Effect of Marbling Degree on Beef Palatability in Bos-taurus and Bos-indicus cattle." J. Anim. Sci. 72:3145. (1994).

Wickersham, E. W. and L. H. Schultz. "Influence of Age at First Breeding on Growth, Reproduction, and Production of Well-Fed Holstein Heifers." J. Dairy Sci. 46:544. (1963).

Wilhelm, K.M. et al, "Effects of Phosphatidylserine and Cholesterol Liposomes on the Viability, Motility, and Acrosomal Integrity of Stallion Spermatozoa Prior to and after Cryopreservation", Cryobiology 33:320, 1996.

Wilson, C. G., et al., "Effects of Repeated hCG Injections on Reproductice Efficiency in Mares." Eq. Vet. Sci. 4:301-308. (1990).

Wilson, D. E. et al., "Mammal Species of the World", Smithsonian Institution Press, 1993, 1206 pp.

Wilson, M.S. "Non-surgical Intrauterine Artificial Insemination in Bitches Using Frozen Semen." J. Reprod. Fertil. Suppl. 47:307-311. (1993).

Windsor, D. P., et al, "Sex Predetermination by Separation of X and Y Chromosome-bearing Sperm: A Review", Reproduction of Fertilization and Development 5, pp. 155-171, (1993).

Wintzer et al.:"Krankheiten des Pferdes Ein Leitfaden fur Studium und Praxiz," 1982, nParey, Berlin Hamburg XP002281450.

Woods, G. L. and Ginther, O. J. "Recent Studies Related to the Collection of Multiple Embryos in Mares." Therio. 19:101-108. (1983).

Woods, J., et al., "Effects of Time of Insemination Relative to Ovulation on Pregnancy Rate and Embryonic-Loss Rate in Mares." Eq. Vet. J. 22(6): 410-415. (1990).

Zhou, Hongwei, et al. "Research on and Development of Flow Cell Sorting Apparatuses," Gazette of Biopyhsics, vol. 13, ed. 3, 1997.

Hamamatsu, "Photomultiplier Tubes," web page, http://optics.org/hamamatsu/pmt.html. Printed on Apr. 15, 2000 4.

Hermesmeyer, G.N. ,et al. Effects of Lactation and Prenatal Androgenization on the Performance, Carcass Composition, and Longissimus muscle sensory characteristics of heifers in the single-calf heifer system. The Professional Animal Scientist 15: 14-23.

Seidel, G. E. Jr., "Fertility of Bulls on the Edge of the Dose-Response Curve for Numbers of Sperm per Inseminate"; Proceedings of the 17th Technical comference on Artificial Insemination & Reproduction, 1998.

Hollinshead, F.K. et al. "In vitro and in vivo assessment of functional capacity of flow cytometrically sorted ram spermatozoa after freezing and thawing." Reprod. Fertil. And Develop. 2003. vol. 15, pp. 351-359.

Hollinshead F. K. et al. "Production of lambs of predetermined sex after the insemination of ewes with low numbers of frozen-thawed sorted X- or Y- Chromosome-bearing spermatozoa", Reprod. Fertil. And Develop. 2002, vol. 14, pp. 503-508.

Hollinshead F. K. et al. "Sex-Sorting and Re-cryopreservation of Frozen-Thawed Ram Sperm for In Vitro Embryo Production" Theriogenology, vol. 59. (2003) pp. 209.

Cran et al. The predetermination of embryonic sex using flow cytometrically separated X and Y spermatozoa, Human Reproduction Update 1996, vol. 2, No. 4 pp. 355-363.

Hamamatsu Photonics K.K. Electronic Tube Center, Photomultiplier Tubes, Brochure Dec. 1997.

Johnson, L. A., et al. The Beltsville Sperm Sexing Technology: High-speed sperm sorting gives improved sperm output for In Vitro fertiliation and AI, Journal of Animal Science, vol. 77, Suppl 2/J, Dairy Sci. vol. 82, Suppl. 2/1999 pp. 213-220.

Peters D., The LLNL high-speed sorter: Design features,operational characteristics, and bioloical utility, Cyometry, 6:290-301 (1985).

Rens W., et al Slit-scan flow cytometry for consistenT high resdolution DNA analysis of X- and Y- chromosome bearing sperm, Cytometry 25:191-199 (1996).

van Munster, E. B. Interferometry in flor to sort unstained X- and Y-Chromosme-Bearing Bull Spermatozoa, Cytometry 47:192-199 (2002).

Scmid, R. L., et al. Effects of follicular fluid or progesterone on *in vitro* maturation of equine oocytes before intracytoplasmic sperm injection with non-sorted and sex-sorted spermatozoa, Journal of Reproduction and Fertility 56:519-525, 2000.

Brink, Z et al. A reliable procedure for superovulating cattle to obtain zygotes and early emryos for microinjection, Theriogenology vol. 41, p. 168, (1994).

Spectra-Physics, The Solid State Laser Company, Vanguard 350-HMD 355, User's Manual, Dec. 2002.

Photon, Inc. Light MeasuringSolutions, NanoScan for High-powered beam Applications, 2005.

Fluorescense Lifetime Systems, www.picoquant.com, Jan. 28, 2005 pp. 2.

NCI ETI Branch, Flow CytometryCore Laboratory, http://home.ncifcrf.gov/ccr/flowcore/ndyag.htm, pp. 5, May 11, 2004.

NCI ETI Branch, Flow CytometryCore Laboratory, http://home.ncifcrf.gov/ccr/flowcore/lsrll.htm, pp. 14, May 11, 2004.

* cited by examiner

SYSTEM FOR IN-VITRO FERTILIZATION WITH SPERMATOZOA SEPARATED INTO X-CHROMOSOME AND Y-CHROMOSOME BEARING POPULATIONS

This application is the U.S. National Stage of International Application No. PCT/US01/45237, filed Nov. 29, 2001 which claims the benefit of U.S. Provisional Application No. 60/253,785 filed Nov. 29, 2000 and U.S. Provisional Application No. 60/253,787 filed Nov. 29, 2000, each hereby incorporated by reference.

I. TECHNICAL FIELD

Devices, compositions, and methods that improve the quality of embryos generated using in-vitro fertilization (IVF) with spermatozoa separated into X-chromosome bearing and Y-chromosome bearing populations.

II. BACKGROUND

An attractive feature of IVF is that many fewer spermatozoa can be required for insemination than for artificial insemination. However, IVF using spermatozoa separated into X-chromosome bearing and Y-chromosome bearing populations (separated spermatozoa) can necessitate modifications to conventional IVF techniques. This may due in part to the pre-capacitation of such spermatozoa.

In most cases, the percentages of oocytes (oocyte, ootid, or ova, or plurality of same as appropriate to the application) fertilized with separated and unseparated spermatozoa are similar, and events during the first cell cycle are timed similarly for separated and unseparated spermatozoa. However, with conventional procedures, blastocyst production with separated spermatozoa can be 70%–90% of controls with spermatozoa that have not been separated. For example, development to blastocysts has been shown to be 17% with bovine oocytes inseminated with separated spermatozoa, compared with >25% which might be expected with IVF using unseparated spermatozoa as described in the journal article entitled "In Vitro Fertilization With Flow-Cytometerically-Sorted Bovine Sperm" Theriogenology 52: 1393–1405 (1999), hereby incorporated by reference.

Several factors may contribute to these results. One factor may be that staining of sperm with Hoechst 33342 appears to cause a decline in motility of spermatozoa. Another factor, may be the physical forces the spermatozoa are subject to during the separation process. As but one example, in flow cytometric separation of spermatozoa, spermatozoa exit the flow cytometer at nearly 100 km/h before impacting on the surface of the collection medium. During transit through the flow cytometer spermatozoa can be subjected to laser light at an intensity of over 100 mW. While the transit time may only be 1–2 μsec, this may affect the spermatozoal DNA, and thus, also effect subsequent embryonic development. The process of separating sperm with flow cytometry can also result in a highly diluted sample, 600,000 spermatozoa/mL or less, and subsequent centrifugation steps are necessary to provide concentrated spermatozoa suitable for insemination.

Another problem with utilizing separated spermatozoa in IVF techniques may be that the facility in which the spermatozoa are separated may be in a different location than where the male mammal from which the spermatozoa are collected is located, which may be different from where the female mammal from which the oocytes are collected is located, which may be a different location from where the in-vitro fertilization is to occur, and which may be a different location from where the female mammal into which the in-vitro cultured embryos are to be transferred. Conventionally, separated sperm may be cryopreserved and transported frozen to the facility at which the IVF techniques are administered. Maturing oocytes are conventionally transported to the facility at which the IVF techniques are administered in portable incubation systems. The maturing oocytes are then inseminated with previously frozen-thawed sperm cells. To avoid cryopreservation of sperm cells or as a convenience to the various facilities involved it may be beneficial to transport maturing oocytes directly to the facility separating the spermatozoa so that separated sperm cells can be added to the oocytes without cryopreservation. However, conventional IVF and in vitro culture of the resulting zygotes typically comprises a separate set of apparatus and procedures making it inconvenient, difficult, or impossible to inseminate and culture oocytes in the same facility in which spermatozoa are separated.

Even though X-chromosome bearing spermatozoa and Y-chromosome bearing spermatozoa have been differentiated by and separated based upon the difference in emitted fluorescence for many years, and even though separated spermatozoa have been used for some time with IVF techniques, and even though there is large commercial market for embryos produced with IVF techniques and separated spermatozoa, the above-mentioned problems have yet to be resolved.

As to the problems with conventional techniques of IVF using separated spermatozoa, and specifically separated spermatozoa, stained spermatozoa, or spermatozoa that are from previously frozen sperm, and with conventional strategies involving the transportation of separated sperm and maturing oocytes, the invention addresses each in a practical manner.

III. DISCLOSURE OF THE INVENTION

Accordingly, one of the broad objects of particular embodiments of the invention can be to provide devices, compositions and methods that provide transportation of inseminated oocytes, promotes cleavage of fertilized ooctyes and improves the quality of embryos generated with techniques utilizing spermatozoa separated into X-chromosome bearing and Y-chromosome bearing populations.

Another broad object of particular embodiments of the invention can be to provide devices, compositions, and methods that promote cleavage and improve quality of embryos generated using IVF with spermatozoa that are derived from previously frozen sperm.

Another broad object of particular embodiments of the invention can be to provide devices, compositions, and methods that promote cleavage and improve quality of embryos generated using IVF with spermatozoa that have previously been stained with a DNA binding fluorochrome.

Another broad object of particular embodiments of the invention can be to provide medium for embryonic culturing that can contain non-essential amino acids.

Another broad object of the invention can be to provide apparatus and methods for transporting maturing oocytes and fertilized oocytes for the convenience of the end user(s) or to avoid cryopreservation of the spermatozoa used to fertilize oocytes.

Naturally further objects of the invention are disclosed throughout other areas of specification.

IV. BRIEF DESCRIPTION OF THE DRAWINGS

V. MODE(S) FOR CARRYING OUT THE INVENTION

The invention involves devices, methods, and compositions for the in-vitro insemination and fertilization of oocytes (oocyte, ootid, or ova, or plurality of same as appropriate to the application) and the culture of embryos resulting from such techniques.

Embodiments of the invention can include fresh spermatozoa, or spermatozoa from frozen-thawed sperm of numerous species of mammals. The invention should be understood not to be limited to the species of mammals cited by the specific examples within this patent application. Embodiments of the invention, for example, may include fresh spermatozoa or spermatozoa from frozen-thawed sperm of animals having commercial value for meat or dairy production such as swine, bovids, ovids, equids, buffalo, or the like (naturally the mammals used for meat or dairy production may vary from culture to culture). It may also include fresh spermatozoa or spermatozoa from frozen-thawed sperm from individuals having rare or uncommon attribute(s), such as morphological characteristics including weight, size, or conformation, or other desired characteristics such as speed, agility, intellect, or the like. It may include frozen-thawed sperm from deceased donors, or fresh or frozen-thawed spermatozoa from rare or exotic mammals, such as zoological specimens or endangered species. Embodiments of the invention may also include fresh or frozen-thawed spermatozoa collected from primates, including but not limited to, humans, chimpanzees, gorillas, or the like, and may also include fresh or frozen-thawed spermatozoa from marine mammals, such as whales or porpoises.

Figure 1:
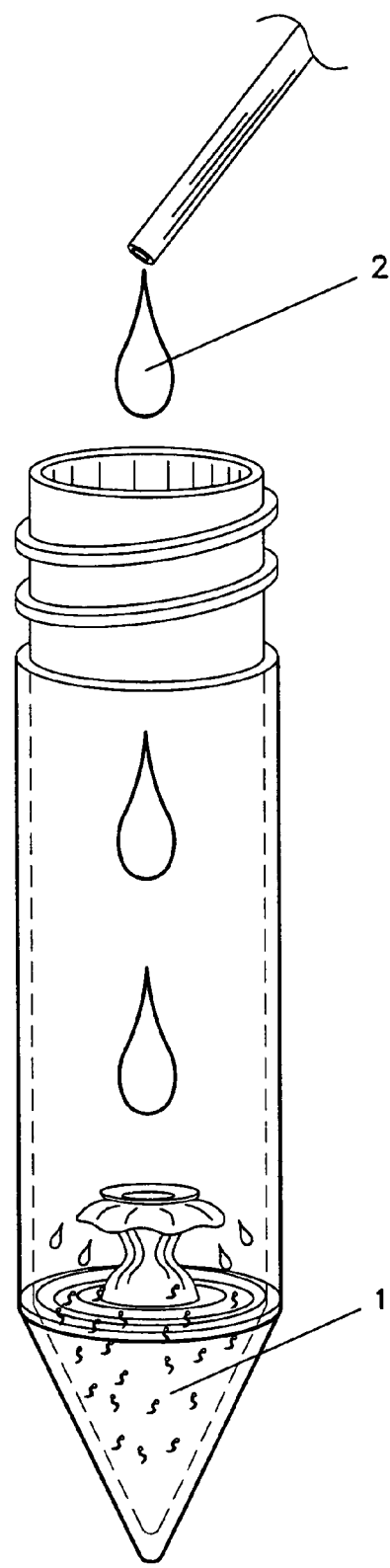
FIG. 1 shows an embodiment of the invention in which spermatozoa from fresh or previously frozen-thawed sperm are stained.

Now referring primarily to FIG. 1, in some embodiments of the invention, Hoechst 33342 stain (1) can be added to bovine spermatozoa contained in frozen-thawed sperm (2) to establish a concentration of 224 µM. The incubation time of the spermatozoa contained in the frozen-thawed sperm (2) with the stain (1) can be about 190 minutes. In anther embodiment of the invention, the stain (1) can be added to the bovine sperm (2) to establish a concentration of 2240 µM and then incubated for about 60 minutes. Frozen-thawed sperm treated in either manner can improve the resolution of X-chromosome bearing from Y-chromosome bearing spermatozoa. Understandably, from application to application (such as frozen-thawed sperm from different species) the amount of incubation time and the specific concentration of stain can adjusted to optimize the resolution of the X-chromosome bearing from Y-chromosome bearing spermatozoa.

With respect to the cleavage rates of inseminated oocyte (s), the increase in stain concentration up to at least 10× does not appear to have a depressive effect on either cleavage or embryonic development. Higher stain concentrations may actually be beneficial with respect to certain applications because the length of incubation time may be decreased improving percent cleavage. From application to application length of incubation time can be adjusted to optimize cleavage results or embryonic development, as desired.

Figure 2:
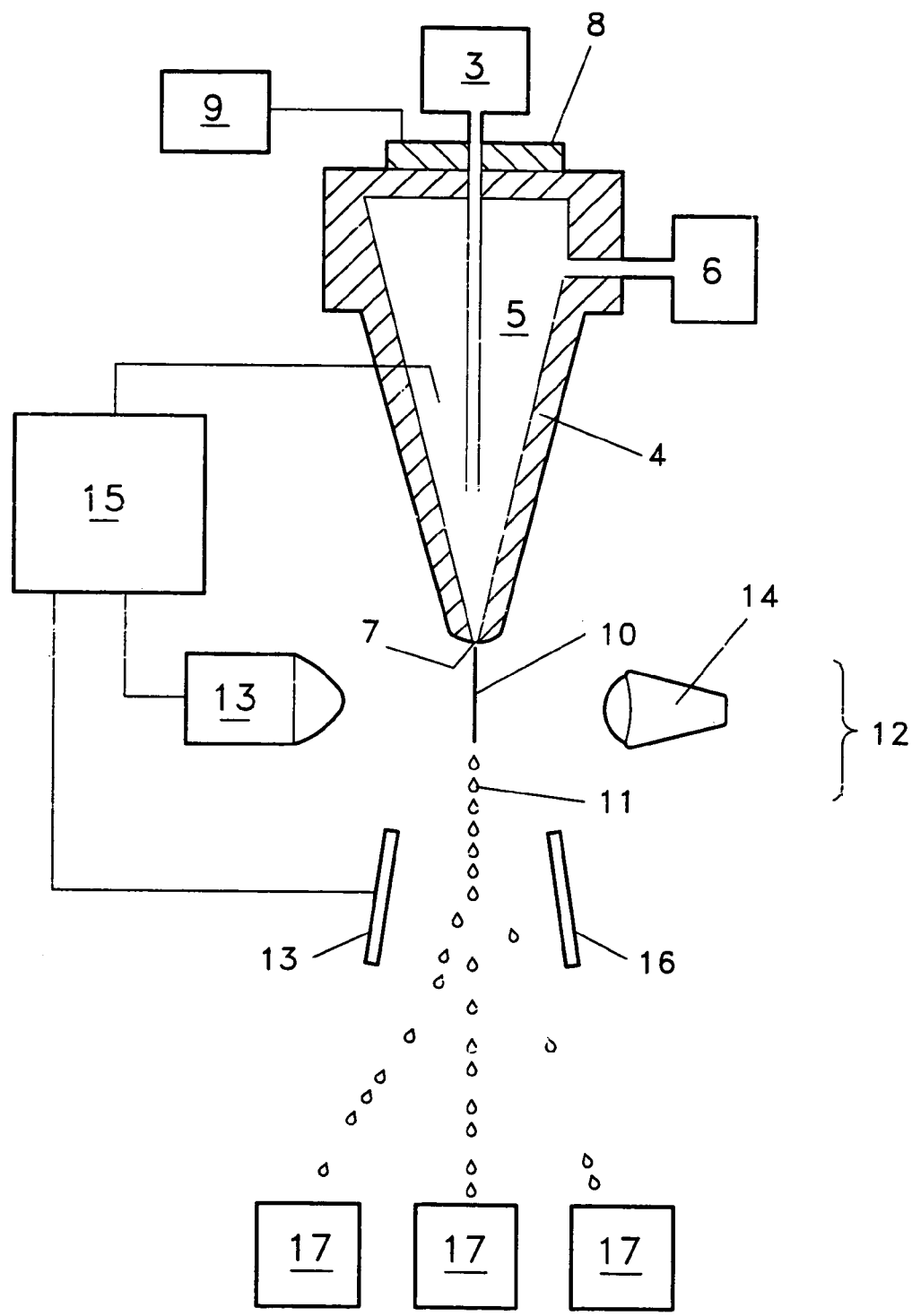
FIG. 2 shows an embodiment of the invention for separating stained spermatozoa in to X-chromosome bearing and Y-chromosome bearing populations.
Figure 3:
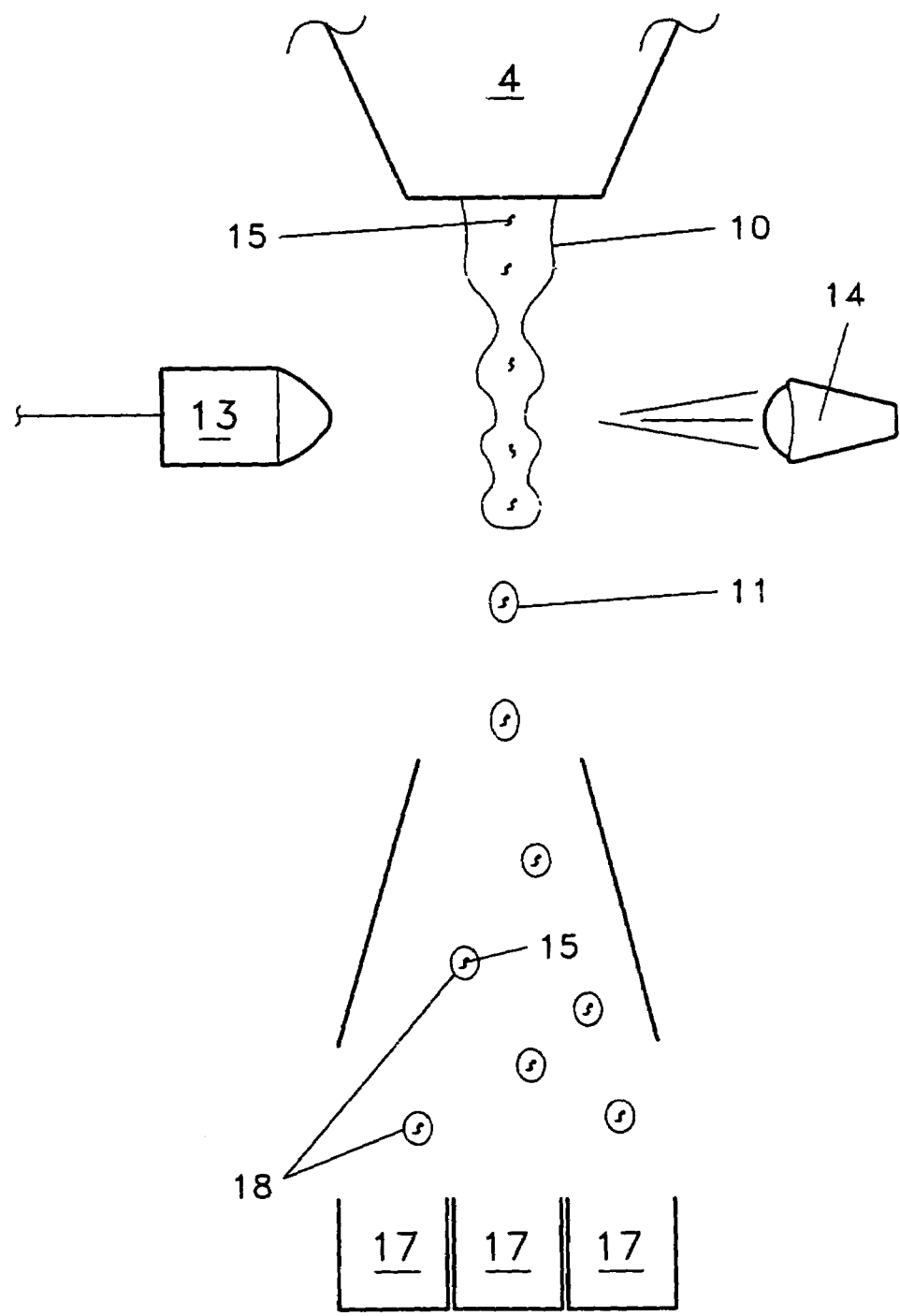
FIG. 3 shows another view of an embodiment of the invention for separating stained spermatozoa in to X-chromosome bearing and Y-chromosome bearing populations.

Now referring primarily to FIGS. 2 and 3, a flow cytometer embodiment of the invention is shown which includes a sperm cell source (3) which acts to establish or supply stained spermatozoa or other type of stained cells to be analyzed by the flow cytometer. The sperm cells are deposited within a nozzle (4) in a manner such that the cells are surrounded by a sheath fluid (5). The sheath fluid (5) is usually supplied by some sheath fluid source (6) so that as the cell source (3) supplies sperm cells, the sheath fluid (5) is concurrently fed through the nozzle (4). In this manner it can be easily understood how the sheath fluid (5) forms a sheath fluid environment for the cells. Since the various fluids are provided to the flow cytometer at some pressure, they flow out of the nozzle (4) and exit at the nozzle orifice (7). By providing some type of oscillator (8) which may be very precisely controlled through an oscillator control (9), pressure waves may be established within the nozzle (4) and transmitted to the fluids exiting the nozzle (4) at nozzle orifice (7). Since the oscillator (9) thus acts upon the sheath fluid (5), the stream (10) exiting the nozzle orifice (7) eventually and regularly forms drops (11). Because the sperm cells are surrounded by a sheath fluid environment, the drops (11) may contain within them individually isolated (generally) cells or other items.

Since the drops (11) generally contain isolated sperm cells, the flow cytometer can distinguish and separate droplets based upon whether or not the appropriate sperm cell is contained within the drop. This is accomplished through a cell sensing system (12). The cell sensing system involves at least some type of sensor (14) which responds to the cells contained within each drop (11) as described by U.S. Pat. No. 5,135,759, hereby incorporated by reference. As the Johnson patent explains for spermatozoa or sperm cells, although the staining and separation inventions can be understood to be used with a variety of frozen-thawed cells, the cell sensing system (12) may cause an action depending upon the relative presence or relative absence of the bound fluorochrome which may be excited by some stimulant such as the laser exciter (13). While each type of sperm cell can be stained by the stain or fluorochrome, as described above, the differing length of the X-chromosome and the Y-chromosome causes different amounts of stain to be bound, Thus, by sensing the degree of fluorescence emitted by the fluorochrome upon excitation it is possible to discriminate between X-bearing spermatozoa and Y-bearing spermatozoa by their differing fluoresence emission levels.

In order to achieve separation and isolation of the appropriate sperm cells, the signals received by sensor (14) are fed to some type of sorter discrimination system (15) which very rapidly makes a differentiation decision and can differentially charge each drop (11) based upon whether it has decided that the desired sperm cell does or does not exist within that drop (11). In this manner the separation or discrimination system (15) acts to permit the electrostatic deflection plates (16) to deflect drops (11) based on whether or not they contain the appropriate sperm cell. As a result, the flow cytometer acts to sort the sperm cells by causing them to land in one or more collectors (17). Thus by sensing some property of the sperm cells the flow cytometer can discriminate between sperm cells based on a particular characteristic and place them in the appropriate collector (17). In the system presently used to sort spermatozoa, the X-bearing spermatozoa droplets are charged positively and thus deflect in one direction, the Y-bearing spermatozoa droplets are charged negatively and thus deflect the other way, and the wasted stream (that is unsortable cells) is uncharged and thus is collected in an undeflected stream into a suction tube or the like.

Now referring primarily to FIG. 3, the process can be even further understood. As shown in that figure, the nozzle (4) emits a stream (10) which because of the oscillator (8) (not shown in FIG. 3) forms drops (11). Since the cell source (3) (not shown in FIG. 3) may supply sperm cells (1) which have been stained according the invention, the magnitude of the fluorescent emission stimulated by the laser exciter (13) is differentially determined by sensor (14) so that the existence or nonexistence of a charge on each drop (11) as it separates from stream (10) can be controlled by the flow cytometer. This control results in positively charged, negatively charged, and uncharged drops based upon the encapsulated sperm cell. As shown in FIG. 3, certain drops are shown as deflected drops (18). These deflected drops (18) are those containing sperm cells (2) differentiated by bearing an X-chromosome or a Y-chromosome. Separated sperm are then deposited in the appropriate collector (17) for later use. See also, International Patent Application PCT/US98/27909, hereby incorporated by reference.

While the above description focuses on the separation of spermatozoa with flow cytometry, separation of X-chromosome bearing spermatozoa and Y-chromosome bearing spermatozoa based upon the difference in measurable fluorescent emission may also include numerous other technologies such as liquid chromatography, gel electrophoresis, and other technologies that similarly excite the amount of bound fluorochrome to differentiate between X chromosome bearing spermatozoa and the Y chromosome bearing spermatozoa.

Embodiments of the invention can also comprise collecting oocytes from a female mammal. With respect to certain embodiments of the invention, oocytes can be aspirated from the ovaries of the desired female mammal or can be obtained from slaughterhouse ovaries. The oocytes can be matured in TCM199 supplemented with about 10% fetal calf serum plus hormones (15 ng FSH, 1 µg LH, 1 µg $E_2$/ml) for 22–24 h at 39° C., in about 5% $CO_2$ in air.

Ten to 15 oocytes can be transferred to a 50 µl drop of fertilization medium containing non-essential amino acids, such as tyrode albumin lactaate pyruvate (TALP) supplemented with non-essential amino acids derived from Eagles Medium, and which can further contain 0.6% bovine serum albumin, 20 µg heparin/mL and 5 mM caffeine. Alternately, oocytes can be fertilized in other medium containing non-essential amino acids such as the chemically defined medium described in the journal article entitled "Lowered Oxygen Tension and EDTA Improve Bovine Zygote Development In Chemically Defined Medium", J. Anim. Sci. (1999), or the SOF medium described in the journal article "Successful Culture In-vitro of Sheep and Cattle Ova", J. Reprod. Fertil. 30:493–497 (1972), each journal article hereby incorporated by reference.

After separating or sorting, sperm cells can be washed by centrifugation for about 10 min at 400 g in collection medium (typically Hepes-tyrode albumin lactate pyruvate medium supplemented with 2.0% bovine serum albumin) followed by suspension in the fertilization medium. Thawed, sorted sperm can be prepared by being centrifuged for 20 minutes at 700 g through a Percoll gradient (90%:45%) for separation of live and dead sperm. The sperm pellet can then be washed with fertilization medium by centrifugation at 400 g for 10 minutes. Sperm can then be added to to the fertilization medium to give a concentration of 1–2 million/mL.

TABLE 1

Cleavage Stage of Oocytes Inseminated with Separated Sperm in Four Different Fertilization Media.

| Media | No. oocytes | % cleavage | % 2-cell at 24 h | % 8-cell at 72 h |
|---|---|---|---|---|
| Fert-TALP | 168 | 76 | 6[a] | 66 |
| Fert-TALP + neaa | 176 | 71 | 26[b] | 67 |
| CDM | 167 | 89 | 75[c] | 70 |
| SOF | 145 | 86 | 49[d] | 69 |

[a,b,c,d]Means with different superscripts differ ($P < .05$).

Now referring primarily to Table 1, as can be understood, oocytes inseminated with separated spermatozoa in fertilization medium containing non-essential amino acids according to the invention exhibit an increased rate of early development through at least the two cell stage.

TABLE 2

Embryonic Development and Blastocyst Quality Resulting From Fertilization in Four Different Fertilization Media (averaged over two culture media)

| Media | No. oocytes | % blastocysts/oocyte Total | D7 | % Grade 1 blastocysts/total blastocysts |
|---|---|---|---|---|
| Fert-TALP | 326 | 20 | 17 | 52[a,c] |
| Fert-TALP-aa | 221 | 20 | 17 | 68[b] |
| CDM | 332 | 22 | 18 | 61[b,c] |
| SOF | 321 | 21 | 17 | 64[b,c] |

[a,b,c]Percentages without common superscripts differ ($P < .05$)
[d]Grade 1 indicates blastocysts with a distinct inner cell mass suitable for embryo transfer.

Now referring primarily to Table 2, some embodiments of the invention in which oocytes are fertilized with sorted spermatozoa in fertilization medium containing supplemented non-essential amino acids can exhibit an enhanced quality of embryos. In embodiments of the invention in which oocytes were fertilized in tyrode albumin lactaate pyruvate (TALP) supplemented with non-essential amino acids derived from Eagles Medium, and further containing 0.6% bovine serum albumin, 20 µg heparin/mL and 5 mM caffeine there was a difference ($P<0.05$) in quality of embryos as compared to TALP without non-essential amino acids.

Presumptive zygotes can be removed from culture and placed in chemically-defined medium (CDM-1) as discussed in the *Journal Animal Science*, 78, 152–157 (2000), hereby incorporated by reference, for 6–7 hours after insemination and cultured for 65–66 hours. Embryos that cleaved were further cultured 96 hours in CDM-2 (further containing MEM essential and non-essential amino acids and 2.0 mM fructose) containing 0.12 IU insulin/mL. Blastocysts were morphologically graded according to the size of inner cell mass and stained with Giemsa to determine cell numbers on day 7 after insemination.

Figure 4:
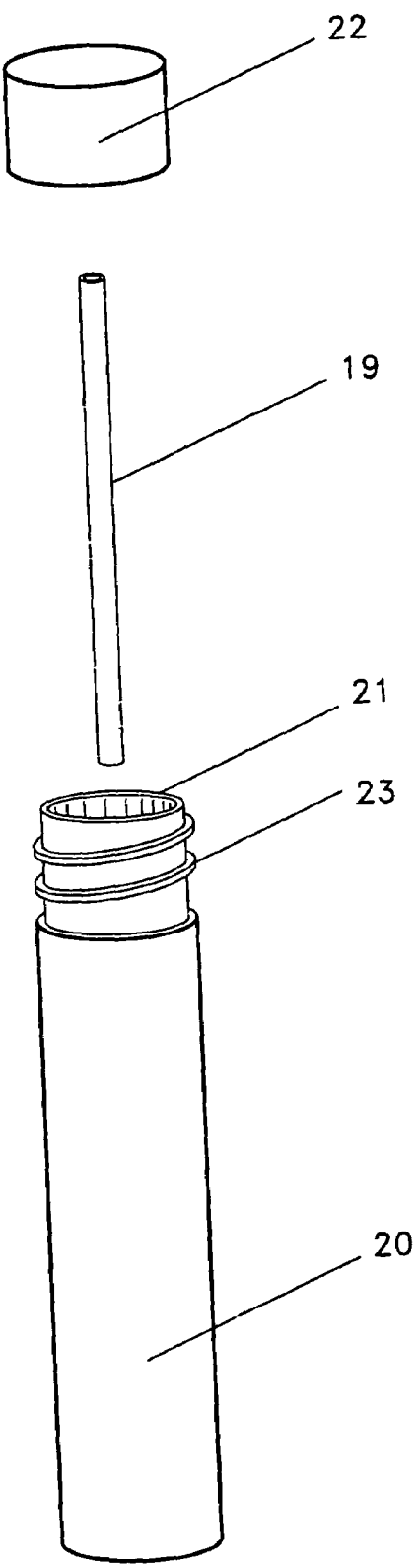
FIG. 4 shows an embodiment of a portable incubation system in which oocytes can be fertilized.

Now referring primarily to FIG. 4, the invention further involves a portable incubation system. Certain embodiments of the invention can comprise a straw (19) having an interior volume between about 0.1 mL and about 0.5 mL into which fertilization medium, and oocytes collected from a female mammal, can be transferred. While the straw (19) could be made of any material compatible with the fertilization medium and the collected oocytes, specific embodiments of the straw (19) can be made of plastic, such as or similar to an artificial insemination straw. The ends of plastic straws can be heat sealed after the fertilization medium and the oocytes are transferred inside.

The invention can further comprise an incubation element (20) configured to encapsulate the straw (19) or a plurality of straws inserted within. In some embodiments of the invention the incubation element (20) can be a glass tube having a single sealable aperture element. The aperture element (21) can be sealed with a cap (22), and in some embodiments the cap (22) and the tube can have spiral threads (23) that can be rotationally mated to close the incubation element (20).

After transfer of a straw (19) or a plurality of straws to the interior volume of the incubation element (20), incubation conditions can be established within. Typical incubation conditions within the interior volume of the incubation element can comprise an atmosphere of five percent carbon dioxide in air and a temperature of about 39° C. (37° C. to 41° C.). Once incubation conditions are established within the incubation element, the incubation element (20) can be sealed and the oocytes can then be transported within the incubation element (20).

In some embodiments of the invention, oocytes can be transported to a sperm cell separation facility where the incubation element (20) is unsealed, the straw (19) is unsealed and a plurality of sperm cells (15) from a population separated on the basis of bearing an X-chromosome or bearing a Y-chromosome can be transferred into the straw (19) containing the oocytes. With respect to some embodiments of the invention a concentration of separated sperm cells (15) can be established of between about 1 million to about 2 million/mL of the fertilization medium. The straw (19) containing the oocytes and spermatozoa in fertilization medium can then be resealed and transferred back into the incubation element (20). The incubation conditions can be re-established and the incubation element sealed. The incubation element (20) containing a straw or plurality of straws (19) can then be transported. During transport the oocytes can become fertilized. Upon arrival zygotes can be transferred from the straw for further culture.

With respect to certain embodiments of the invention, oocytes can first be inseminated with separated or unseparated spermatozoa in conventional 50 µl drops and loaded into a 0.25 mL straw or straws (19) within two hours after insemination. Straws (19) can be heat sealed and put into the incubation element (20). The open incubation element containing straws with inseminated oocytes can be equilabrated with 5% carbon dioxide in air at about 39° C. for at least one hour and then tightly capped and cultured under the same conditions for between about 18–20 hours.

Again referring primarily to Table 2, fewer oocytes (P<0.05) fertilized in Fert-TALP developed to the 2-cell stage by 24 hours than in any other media. Notably, the vast majority of oocytes (75%) fertilized in CDM medium cleaved to 2-cell stabe by this time. By 72 hours post-insemination, there was no difference between any of the media, possibly due to the long 8-cell stage cell cycle.

There was no difference between any of the media on rate of development to blastocysts. However, there was a significant difference in quality of embryos between Fert-TALP and Fert-TALP+non-essential amino acids.

Progression of early bovine embryonic development using separated sperm are similar to studies with in-vivo or in-vitro cleavage of oocytes fertilized with unseparated spermatozoa. In the cow the first in-vivo cleavage occurs at 24–28 hours following ovulation, and the first in-vitro cleavage tages place at 24–48 hours after insemination.

Earlier cleavage occurred with oocytes fertilized in CDM, SOF, and Fert-TALP+ aa medium than in conventional Fert-TALP medium. This can be because CDM, SOF, and Fert-TALP+ non-essential amino acids, all contain non-essential amino acids, which may play a role in how quickly spermatozoa penetrate oocytes, of in the length of the first cell cycle.

As can be easily understood from the foregoing, the basic concepts of the present invention may be embodied in a variety of ways. It involves the staining of spermatozoa, whether fresh spermatozoa or frozen-thawed spermatozoa, separation and isolation techniques which may be used with such stained spermatozoa, as well as devices to accomplish the staining, separation, isolation of such stained spermatozoa into X-chromosome bearing and Y-chromosome bearing populations, and the tramsportion of maturing oocytes and fertilized oocytes. In this patent application, the staining and separating techniques used with spermatozoa are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this international Patent Cooperation Treaty patent application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in functionally-oriented terminology, each aspect of the function is accomplished by a device, subroutine, or program. Apparatus claims may not only be included for the devices described, but also method or process claims may be included to address the functions the invention and each element performs. Neither the description nor the terminology is intended to limit the scope of the claims which now be included.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "sorter" should be understood to encompass disclosure of the act of "sorting"—whether explicitly discussed or not—and, conversely, were there only disclosure of the act of "sorting", such a disclosure should be understood to encompass disclosure of a "sorter" and even a "means for sorting". Such changes and alternative terms are to be understood to be explicitly included in the description.

Additionally, the various combinations and permutations of all elements or applications can be created and presented. All can be done to optimize the design or performance in a specific application.

Any acts of law, statutes, regulations, or rules mentioned in this application for patent: or patents, publications, or other references mentioned in this application for patent are hereby incorporated by reference. Specifically, U.S. Provisional Patent Application No. 60/253,787, filed Nov. 29, 2000 and U.S. Provisional Patent Application No. 60/253,785, filed Nov. 29, 2000, are hereby incorporated by reference including any figures or attachments, and each of references in the following table of references are hereby incorporated by reference.

US Patent Documents

| DOCUMENT NO. | DATE | NAME | CLASS | SUBCLASS | FILING DATE |
| --- | --- | --- | --- | --- | --- |
| 32,350 | Feb. 10, 1987 | Bhattacharya | | | Nov. 22, 1974 |
| 3,687,806 | Aug. 29, 1972 | Van den Bovenkamp | 195 | 1.3 | Nov. 04, 1969 |
| 3,829,216 | Aug. 13, 1974 | Persidsky | 356 | 36 | Oct. 02, 1972 |
| 3,894,529 | Jul. 15, 1975 | Shrimpton | 128 | 1 R | Apr. 10, 1969 |
| 4,009,260 | Feb. 22, 1977 | Ericsson | 424 | 105 | Dec. 11, 1974 |
| 4,067,965 | Jan. 10, 1978 | Bhattacharya | 424 | 105 | Dec. 17, 1975 |
| 4,083,957 | Apr. 11, 1978 | Lang | 424 | 78 | Feb. 04, 1976 |
| 4,085,205 | Apr. 18, 1978 | Hancock | 424 | 105 | Jan. 24, 1977 |
| 4,092,229 | May 30, 1978 | Bhattacharya | 204 | 180 R | Oct. 20, 1976 |
| 4,155,831 | May 22, 1979 | Bhattacharya | 207 | 299 R | Feb. 23, 1978 |
| 4,191,749 | Mar. 04, 1980 | Bryant | 424 | 105 | Oct. 11, 1977 |
| 4,225,405 | Sep. 30, 1980 | Lawson | 204 | 180 R | Aug. 16, 1978 |
| 4,276,139 | Jun. 30, 1981 | Lawson | 204 | 180 R | Oct. 09, 1979 |
| 4,339,434 | Jul. 13, 1982 | Ericsson | 424 | 105 | Aug. 17, 1981 |
| 4,362,246 | Dec. 07, 1982 | Adair | 209 | 3.3 | Jul. 14, 1980 |
| 4,448,767 | May 15, 1984 | Bryant | 424 | 85 | Feb. 15, 1980 |
| 4,474,875 | Oct. 02, 1984 | Shrimpton | 435 | 002 | Aug. 18, 1980 |
| 4,501,366 | Feb. 26, 1985 | Thompson | 209 | 556 | Dec. 14, 1982 |
| 4,511,661 | Apr. 16, 1985 | Goldberg | 436 | 503 | Dec. 30, 1983 |
| 4,605,558 | Aug. 12, 1986 | Shrimpton | 424 | 561 | Apr. 20, 1984 |
| 4,660,971 | Apr. 28, 1987 | Sage et al. | 356 | 39 | May 03, 1984 |
| 4,680,258 | Jul. 14, 1987 | Hammerling et al | 435 | 7 | Aug. 09, 1983 |
| 4,673,288 | Jun. 16, 1987 | Thomas et al. | | | |
| 4,683,195 | Jul. 28, 1997 | Mullis et al | | | |
| 4,683,202 | Jul. 28, 1987 | Mullis | | | |
| 4,698,142 | Oct. 06, 1987 | Muroi et al | 204 | 182.3 | Jul. 31, 1985 |
| 4,749,458 | Jun. 07, 1988 | Muroi et al | 204 | 182.3 | Mar. 02, 1987 |
| 4,790,653 | Dec. 13, 1988 | North, Jr. | | | |
| 4,988,619 | Jan. 29, 1991 | Pinkel | 435 | 30 | Nov. 30, 1987 |
| 4,999,283 | Mar. 12, 1991 | Zavos et al | 435 | 2 | Aug. 18, 1989 |
| 5,021,244 | Jun. 04, 1991 | Spaulding | 424 | 561 | May 12, 1989 |
| 5,055,393 | Oct. 08, 1991 | Kwoh et al | | | |
| 5,135,759 | Aug. 04, 1992 | Johnson | 424 | 561 | Apr. 26, 1991 |
| 5,346,990 | Sep. 13, 1994 | Spaulding | 530 | 350 | Mar. 12, 1991 |
| 5,371,585 | Dec. 06, 1994 | Morgan et al. | 356 | 246 | Nov. 10, 1992 |
| 5,437,987 | Aug. 01, 1995 | Ten et al | | | |
| 5,439,362 | Aug. 08, 1995 | Spaulding | 424 | 185.1 | Jul. 25, 1994 |
| 5,461,145 | Oct. 24, 1995 | Kudo et al | | | |
| 5,466,572 | Nov. 14, 1995 | Sasaki et al. | 435 | 2 | Apr. 25, 1994 |
| 5,480,774 | | | | | |
| 5,483,469 | Jan. 09, 1996 | Van den Engh et al. | 364 | 555 | Aug. 02, 1993 |
| 5,494,795 | Feb. 27, 1996 | Guerry et al. | 435 | 6 | May 5, 1993 |
| 5,503,994 | Apr. 02, 1996 | Shear et al. | 436 | 90 | Oct. 08, 1993 |
| 5,578,449 | Nov. 26, 1996 | Frasch et al. | 435 | 6 | Apr. 20, 1995 |
| 5,514,537 | May 07, 1996 | Chandler | 435 | 002 | Nov. 28, 1994 |
| 5,589,457 | Dec. 31, 1996 | Wiltbank | 514 | 12 | Jul. 03, 1995 |
| 5,602,039 | Feb. 11, 1997 | Van den Engh | 436 | 164 | Oct. 14, 1994 |
| 5,602,349 | Feb. 11, 1997 | Van den Engh | 73 | 864.85 | Oct. 14, 1994 |
| 5,622,820 | Apr. 11, 1997 | Rossi | 435 | 5 | Nov. 3, 1994 |
| 5,641,457 | Mar. 09, 1999 | Tomiyama et al. | 250 | 207 | Jun. 16, 1997 |
| 5,643,796 | Jul. 01, 1997 | Van den Engh et al | 436 | 50 | Oct. 14, 2004 |
| 5,660,997 | Aug. 26, 1997 | Spaulding | 435 | 7.21 | Jun. 07, 1995 |
| 5,690,895 | Nov. 25, 1997 | Matsumoto et al. | 422 | 73 | Dec. 06, 1996 |
| 5,700,692 | Dec. 23, 1997 | Sweet | 436 | 50 | Sep. 27, 1994 |
| 5,726,364 | Mar. 10, 1998 | Van den Engh | 73 | 864.85 | Feb. 10, 1997 |
| 5,819,948 | Oct. 13, 1998 | Van den Engh | 209 | 158 | Aug. 21, 1997 |
| 5,876,942 | Mar. 2, 1999 | Cheng et al | 435 | 6 | Jul. 24, 1997 |
| 5,880,457 | Mar. 09, 1999 | Tomiyama et al. | 250 | 207 | Jun. 16, 1997 |
| 5,985,216 | Nov. 16, 1999 | Rens, et al. | 422 | 073 | Jul. 24, 1997 |
| 6,071,689 | Jun. 06, 2000 | Seidel et al. | 435 | 2 | Jan. 29, 1998 |

| Foreign Documents | | |
|---|---|---|
| DOCUMENT NO | DATE | COUNTRY |
| WO 96/12171 | Oct. 13, 1995 | United States |
| WO 98/34094 | Jun. 08, 1998 | NZ |
| WO 99/05504 | Jul. 24, 1998 | US |
| WO 99/33956 | Aug. 07, 1999 | US |
| WO 99/38883 | May 08, 1999 | US |
| WO 99/42810 | Aug. 26, 1999 | US |
| WO 00/06193 | Oct. 02, 2000 | US |

OTHER REFERENCE DOCUMENTS

Roser, J F., Evans, J. W., Kiefer, D P., Neeley, D. P. and Pacheco, C. A. 1980. Reproductive efficiency in mares with nnnanti-hCG antibodies. Proc 9$^{th}$ Int. Congr. Artira. Repro. and A.I. 4:627. abstr.

"Applying Semen Sexing Technology to the AI Industry", National Association of Animal Breeders, September 2000, pp. 1–16

"Sexed Semen Offers Faster Genetic Gain", Farming News, Livestock Supplement, February 1997, p. 28.

Akhtar, S., et al., "Prevalence of Five Stereotypes of Bluetongue Virus in a Rambouillet Sheep Flock in Pakistan", Veterinary ecord 136, 1995, p. 495.

Akhtar, S., et al., "Sex Preselected in Cattle: a Field Trial", Veterinary Record 136, 1995, p. 495–496.

Aldrich, S. L., Berger, L. L., Reiling, B. A., Kegler, D. I., and Nagh, T. G. 1995. "Parturition and periparturient reproductive and metabolic hormone concentration in prenatally androgenized beefheifer", I. Anim. Sci. 73:3712.

Amann, R. P. "Issues affecting commercialization of sexed sperm". Therio: 52:1441, 1999

Amann, R. P. et al, "Prospects For Sexing Mammalian Sperm," Colorado Associated University Press, Animal Reproduction Laboratory College of Veterinary Medicine and Biomedical Sciences, Colorado State University, Fort Collins, Colo., 80523, 1982

American Meat Science Association in cooperation with National Livestock and Meat Board. "Research guidelines for cookery, sensory evaluation and instrumental tenderness measurements of fresh meatK", 1995

Amoah, E. A. and Gelaye, S. 1996. Biotechnological advances in goat reproduction. J. Anim. Sci. 75(2):578–585.

Andersen, V. K., Aamdal, J. and Fougner, J. A. 1973. Intrauterine und tiefzervikale Insemination mit Gefriersperma bein Schat. Zuchthygiene. 8:113–118.

Bagley, C. P. 1993. Nutritional management of replacement beef heifers-A review. J. Anim. Sci. 71:3155–3163.

Bailey, C. M., Reid, C. R., Ringkob, T. P., Koh, Y. O., and Foote, W. D. "Nulliparous versus primiparous crossbred females for beef." J. Anim. Sci. 69:1403., 1991

Baker, R. D., Dziuk, P. J. and Norton, H. W. 1968. Effect of volume of semen, number of sperm and drugs on transport of sperm in artificially inseminated gilts. J. Anim. Sci. 27:88–93.

Barnes, F. L. and Eyestone, W. H., "Early Cleavage and the Matemal Zygotic Transition in Bovine Embryos", Theriogeneology, Vol. 33, No. 1, January 1990, pp. 141–149

Becker, S. E. and Johnson, A. L. 1992. Effects of gonadotropin releasing hormone infused in a pulsatite or continuous fashion on serum gonadotropin concentrations and ovulation in the mare. J. Anim. Sci. 70:1208–1215.

Bedford, S. J. and Hinrichs, K. 1994. The effect of insemination volume on pregnancy rates of pony mares. Theriogenology 42:571–578.

Bellows, R. A., Short, R. E., Anderson, D. C., Knapp, B. W., and Pahnish, O. F. "Cause and effect relationships associated with calving difficulty and calfbirth weight", J. Anim. Sci. 33:407, 1971

Berardinelli, J. G., R. A. Dailey, R. L. Butcher, and E. K. Inskeep. "Sourceof progesterolle prior to puberty in beef heifers". J. Anim. Sci. 49:1276., 1979

Berger, G. S. 1987. Intratubal insemination. Fert. Steril. 48:328–330.

Bergfeld, E. G., Kojima, F. N., Cupp, A. S., Wehnnan, M. E., Peters, K. T., Garciawinder, M., and Kinder, J. E., "Ovarian follicular development in prepubertal heifers is influenced by level of dietary energy-intake", Bio. of Repro. 51:1051, 1994

Berry, B. W., Smith, G. C., and Carpente. zl, "Beef carcass maturity indicators and palatability attributes", J. Anim. Sci. 38:507, 1974

Beyhan, Z., et al., "Sexual Dimorphism in IVF Bovine Embryos Produced by Sperm Sorted by High Speed Flow Cytometry", Theriogenology 49, 1998, p. 359.

Blanchard, T. and Dickson, V., "Stallion Management", The Veterinary Clinics of North America, Equine Practice, Vol. 8, No. 1, April 1992, pp 207–218.

Bond, J., et al., "Growth and carcass traits of open beef heifers versus beef heifers that have calved", Nutrition Reports International 34:621. 1986

Boucque, C. V., et al., "Beef-production with maiden and once-calved heifers", Livestock Prod. Sci. 7:121. 1980

Bourdon, R. M. and J. S. Brinks. "Simulated efficiency of range beef-production". Culling strategies and nontraditional management-systems. J. Anim. Sci. 65:963. 1987

Bracher, V. and Allen, W. R., "Videoendoscopic Examination of the Mare's Uterus: Findings in Normal Fertile Mares", Equine Veterinary Journal, Vol. 24 (1992), pp. 274–278

Braselton, W. E. and McShan, W. H. 1970. "Purification and properties of follicle stimulating and luteinizing hormones from horse pituitary glands", Arch. Biochem. Biophys. 139:45–48.

Brethour, J. R., "The single-calfheifer system", Kans. Agric. Sta. Rep. Frog. 570. 1989

Bristol, S. P. 1982. Breeding behavior of a stallion at pasture with 20 mares in synchronized oestrus. J. Reprod. Fert. Suppl. 32:71.

Brookes, A. J. and Obyme, M., "Use of cow-heifers in beef production", J. of the Royal Agricultural Society of England 126:30. 1965

Buchanan, B. R., et al, "Insemination of Mares with Low Numbers of Either Unsexed or Sexed Spermatozoa", Theriogenology, Vol. 53, pp 1333–1344, (2000)

Burns, P. D. and Spitzer, J. C., "Influence of biostimulation on reproduction in postpartum beef-cows", J. Anim. Sci. 70:358. 1992

Burwash, L. D., Pickett, B. W., Voss, J. L. and Back, D. G. 1974. "Relationship of duration of estms to pregnancy rate in normally cycling, non-lactating mares" J.A.V.M.A. 165: 714–716.

Byerley, D. J., et al., "Pregnancy rates of beef heifers bred either on puberal or 3rd estrus". J Anim. Sci. 65:645. 1987

Caslick, E. A., "The Vulva and the Vulvo-vaginal Orifice and its Relation to Genital Health of the Thoroughbred Mare", Cornell Veterinarian, Vol. 27, 1937, pp. 178–187

Catt, et al., "Assessment of Ram and Boar Spermatozoa During Cell-Sorting by Flow Cytometry", Reproduction Dom Animal, Vol. 32, 1997, pp 251–258.

Catt, S. L., et al., "Birth of a Male Lamb Derived from an In Vitro Matured Oocyte Fertilized by Intracytoplasmic Injection of a Single Presumptive Male Sperm", Veterinary Record 139, 1996, pp. 494–495.

Chin, W. W. and Boime, I. 1990. In: Glycoprotein Hormones. Serona Symp. Norwell, Mass. pp. 19–20

Chung, Y. G., Schenk, J. L., Herickhoff, L. A. and Seidel, G. E. Jr. 1998. Artificial insemination of superovulated heifers with 600,000 sexed sperm. J Anim. Sci. Suppl. 1. 836:215. abstr.

Clement, F., Vincent, P., Mahla, R., Meriaux, J. C. and Palmer, E. 1998. Which insemination fertilizes when several successive inseminations are performed before ovulation. $7^{th}$ Int. Symp. Eq. Repro. 151. abstr.

Coleou, J., et al., "Essai de velage tres precoce de genisses en vue de la production de viande." Essai Vauz/Aure no. 50, programme USFGC-INAPG-ITFC. 1974

Cran, D. G., et al., "Production of Bovine Calves Following Separation of X- and Y-Chromosome Bearing Sperm and In Vitro Fertilisation", Veterinary Record 132, 1993, pp. 40–41.

Cran, D. G., et al., "Production of Lambs by Low Dose Intrauterine Insemination with Flow Cytometrically Sorted and Unsorted Semen", Theriogenology 47, 1997, p. 267.

Crowley, J. P. The facts of once-bred heifer production. (Ed) J. B. Owens. The maiden female-a means of increasing meat production. School of Agric., Univ. of Aberdeen, Scotland. 1973

Curran, S. 1998. In: Equine Diagnostic Ultrasonography. Fetal gender determination. Rantanen & McKinnon. $1^{st}$ Ed. Williams and Wilkins. pp. 165–169.

Day, B. N., Abeydeera, L. R., Johnson, L. A., Welch, G. R., Wang, W. H., Cantley, T. C. and Rieke, A. 1998. Birth of piglets preselected for gender following in vitro fertilization of in vitro matured pig oocytes by X and Y bearing spermatozoa sorted by high speed flow cytometry. Theriogenology. 49(1):360. abstr.

Dean, P. N., Pinkel, D. and Mendelsob. n, M. L. 1978. Hydrodynamic orientation of spermatozoa heads for flow cytometry. Biophys. J. 23:7–13.

Demick, D. S., Voss, J. L. and Pickett, B. W. 1976. Effect of cooling, storage, glycerization and spermatozoal numbers on equine fertility. J. Anim. Sci. 43:633–637.

DenDaas, J. H. G., De Jong, G., Lansbergen, L. M. T. E. and Van Wagtendonk-De Leeuw, A. M. 1998. The relationship between the number of spermatozoa inseminated and the reproductive efficiency of-dairy bulls. J Dairy Sci. 81: 1714–1723.

Denham, A. "In-vitro studies on sandhill range forage as related to cattle preference", M.S. Thesis. 1965. Colorado State University.

Deutscher, G. H. "Extending interval from seventeen to nineteen days in the melengestrol acetate-prostaglandin estrous synchronization program for heifers". The Professional Animal Scientist 16:164. 2000

"Diagnostic Products Corporation. Coat-A-Count", Progesterone.com. 1998.

Dikeman, M. E. Cattle production systems to meet future consumer demands. J. Anim. Sci. 59:1631, 1984

Dinnyes, A., et al., "Timing of the First Cleavage Post-insemination Affects Cryosurvival of In Vitro-produced Bovine Blastocysts", Molec Reprod Develop 53, 1999, pp 318–324.

Donaldson, L. E., "Effect of Insemination Regimen on Embryo Production in Superovulated Cows", The Veterinary Record, Jul. 13, 1985, pp. 35–37

Donoghue, A. M., Byers, A. P., Johnston, L. A., Armstrong, D. L. and Wildt, D. E. 1996. Timing of ovulation after gonadotropin induction and its importance to successful intrauterine insemination in the tiger (Panthera tigris). J. Reprod. Fert. 107:53–58.

Douglas, R. H. 1979. Review of superovulation and embryo transfer in the equine. Theriogenology. 11:33–46.

Douglas, R. H., Nuti, L. and Ginther, O. J. 1974. Induction of ovulation and multiple ovulation on seasonally-anovulatory mares with equine pituitary fractions. Theriogenology. 2(6): 133–142.

Doyle, S. P., et al. "Artificial insemination of lactating angus cows with sexed semen". Proc. Western Sect. Am.Soc.Anim. Sci. 50:203. 1999

Duchamp, G., Bour, B., Combamous, Y. and Palmer, E. 1987. Alternative solutions to hCG induction of ovulation in the mare. J. Reprod. Fert. Suppl. 35:221–228.

Evans, M. J. and Irvine, C. H. G. 1977. Induction of follicular development, maturation and ovulation by gonadotropin releasing hormone administration to acyclic mares. Bio. Reprod. 16:452–462.

Ferrell, C. L. and T. G. Jenkins. "Energy-Utilization by Mature, nonpregnant, nonlactating cows of different types" J. Anim. Sci. 58:234. 1984

Ferrell, C. L. "Effects of post-weaning rate of gain on onset of puberty and productive performance of heifers of different breeds. J. Anim. Sci. 55:1272. 1982

Field, R. A., et al., "Bone-ossification and carcass characteristics of wethers given silastic implants containing estradiol". I. Anim. Sci. 68:3663–3668. 1990

Field, R., R. et al., "Growth, carcass, and tenderness characteristics of virgin, spayed, and single-calfheifers.", J. Anim. Sci. 74:2178. 1996

Fitzgerald, B. P., Peterson, K. D. and Silvia, P. J. 1993. Effect of constant administration of a gonadotropin-releasing hormone agonist on reproductive activity in mares: Preliminary evidence on suppression of ovulation during the breeding season. Am. J. Vet. Res. 54:1746–1751.

Fluharty, F. L., et al., "Effect of weaning and diet on growth of calves." Research and Reviews. The Ohio State University Department of Animal Sciences. 1996

Fluharty, F. L., et al., "Effects of Age at Weaning and Diet on Growth of Calves", Ohio Agri. Res. and Dev. Circular, 1996, 156:29.

Foulkes, J. A., Stewart, D. L. and Herbert, C. N. 1977. Artificial insemination of cattle using varying numbers of spermatozoa. Vet. Rec. 101:205.

Fugger, E. F., "Clinical Experience with Flow Cytometric Separation of Human X- and Y-Chromosome Bearing Sperm", Theriogenology, Vol. 52, pp. 1435–1440 (1999)

Fulwyler, M. J. 1965. Electronic separation of biological cells by volume. Science. 150:910.

Fulwyler, M. J. 1977. Hydrodynamic orientation of cells. J Histochem. Cytochem. 25:781–783.

Seidel, G. E. Jr., "Artificial Insemination With X-and Y-Bearing Bovine Sperm", Animal Reproduction and Biotechnology Laboratory, Colorado State University, Fort Collins, Colo.; Germplasm and Gamete Physiology Lab, ARS, U7SDA, Beltsville, Md.; Atlantic Breeders Coop, Lancaster, Pa.; DUO Diary, Loveland, Colo., USA January 1996.

Garner, D. L., Gledhill, B. L., Pinkel, D., Lake, S., Stephenson, D., Van Dilla, M. A. and Johnson, L. A. 1983.

"Quantification of the X and Y chromosome-bearing spermatozoa of domestic animals by flow cytometry". Biol. Reprod. 28:312–321.

Ginther, O. J. 1983. Sexual behavior following introduction of a stallion into a group of mares. Theriogenology. 19:877.

Ginther, O. J. 1992. In: Reproductive Biology of the Mare. (2$^{nd}$ Ed.) Equiservices, Cross Plains, Wis.

Gledhill, B. L. 1988. Gender preselection: historical, technical and ethical perspective. Semin Reprod. Endocrinol. 6:385–395.

Gombe, S. and Hansel, W. "Plasma luteinizing-hormone (LH) and progesterone levels in heifers on restricted energy intakes." J. Anim. Sci. 37:728. 1973

Gourley, D. D. and Riese, R. L. 1990. Laparoscopic artificial insemination in sheep. Vet. Clin. N. Amer: Food Anim. Prac. 6(3):615–633.

Gravert, H. 0., "Genetic Aspects of Early Calving." In: J. C. Taylor (Ed.) The early calving of heifers and it's impact on beef production. 59. 1975

Gregory, K. E., et al., "Characterization of biological types of cattle III .2."Growth-rate and puberty in females. J. Anim. Sci. 49:461. 1979

Grimes, I. F, and T. B. Turner. "Early weaning of fall bom calves II." Post weaning performance of early and normal-weaned calves. I. Prod. Agric. 4:168. 1991

Grondahl, C., et al, "In Vitro Production of Equine Embryos", Biology of Reproduction, Monograph Series I, pp. 299–307 (1995)

Guillou, F. and Combamous, Y. 1983. Purification of equine gonadotropins and comparative study of their acid-dissociation and receptor-binding specificity. Biochem. Biophys. Acta. 755:229–236.

Gumsey, M. P., and Johnson, L. A., "Recent improvements in efficiency of flow cytometric sorting of X and Y-chromosome bering sperm of domestic animals: a review", 1998, New Zealand Society of Animal Protection, three pages.

Hall, J. B., et al., "Effect of age and pattern of gain on induction of puberty with a progestin in beef heifers." J. Anim. Sci. 75:1606. 1997

Hamano, K., et al., "Gender Preselection in Cattle with Intracytoplasmically Injected, Flow Cytometrically Sorted Sperm Heads", biology of Reproduction 60, 1999, pp. 1194–1197.

Harrison, L. A., Squires, E. L. and McKinnon, A. O. 1991. Comparison of hCG, buserelin and luprostiol for induction of ovulation in cycling mares. Eq. Vet. Sci. 3:163–166.

Harte, F. J. "System of production of bee from once calved heifers." In: J. C. Taylor (Ed.) The early calving ofheifers and it's impact on beef production. 123. 1975

Hawk, H. W., et al., "Fertilization Rates in Superovulating Cows After Deposition of Semen on the Infundibulum Near the Uterotubal Junction or After Insemination with High Numbers of Sperm", XP-002103478, Theriogenology, May 1988, Vol. 29, No. 5, pp 1131–1142.

Hemlesmeyer, G. N., et al. "Effects of lactation and prenatal androgenization on the perfomlance, carcass coompostion and longissimus muscle sensory characteristics of heifers in the single-calfheifer system." The Professional Animal Scientist 15:14. 1999

Hennegmeyer, G. N., et al. "Effects of prenatal androgenization and implantation on the performance and carcass composition of lactating heifers in the single-calfheifer system." The Professional Animal Scientist 15:173. 1999

Hilton, G. G., et al., "An evaluation of current and alternative systems for quality grading carcasses of mature slaughter cows." I. Anim. Sci. 76:2094. 1998

Ho, L., et al., "Influence of gender, breed and age on maturity characteristics of sheep." J. Anim. Sci. 67:2460–2470. 1989

Hofferer, S., Lecompte, F., Magallon, T., Palmer, E. and Combamous, Y. 1993. Induction of ovulation and superovulation in mares using equine LH and FSH separated by hydrophobic interaction chromatography. J. Reprod. Fert. 98:597–602.

Hohenboken, W. D. "Applications of sexed semen in cattle production." Therio.52:1421. 1999

Holtan, D. W., Douglas, R. H. and Ginther, O. J. 1977. Estrus, ovulation and conception following synchronization with progesterone, prostaglandin F2 ct and human chorionic gonadotropin in pony mares. J. Anim. Sci. 44:431–437.

Householder, D. D., Pickett, B. W., Voss, J. L. and Olar, T. T. 1981. Effect of extender, number of spermatozoa and hCG on equine fertility. J. Equine Vet. Sci. 1:9–13.

Howard, J. G., Bush, M., Morton, C., Morton, F., Wentzel, K. and Wildt, D. E. 1991. Comparative semen cryopreservation in ferrets (Mustela putorious furo) and pregnancies after laparoscopic intrauterine insemination with frozen-thawed spermatozoa. J. Reprod. Fert. 92:109–118.

Howard, J. G., Roth, T. L., Byers, A. P., Swanson, W. F. and Wildt, D. E. 1997. Sensivity to exogenous gonadotropins for ovulation and laparoscopic artificial insemination in the theetab and clouded leopard. Biol. Reprod. 56:1059–1068.

Hunter, R. H. F. 1980. Transport and storage of spermatozoa in the female reproductive tract.

Proc 4$^{th}$ Int. Congr. Artira. Repro. and A. I. 9:227–233.

Hyland, J. H., Ainsworth, C. G. V. and Langsford, D. A. 1988. Gonadotropin-releasing hormone (GnRH) delivered by continuous infusion induces fertile estrus in mares during seasonal acyclicity. Proc. Amer. Assoc. Eq. Prac. 181–190.

Irvine, C. H. G. and Alexander, S. L. 1993. In: Equine Reproduction. Edited by McKirmon and Voss. Lea and Febiger. Philadelphia, London. pp. 37.

Jafar, et al., "Sex Selection in Mammals: A Review", Theriogenology, vol. 46, 1996, pp 191–200.

Jarriage, R. "Age of cows at first calving in France." J. C. Taylor (Ed.) The early calving ofheifers and it's impact on beef production. 10. 1975

Jasko, D. J., Martin, J. M. and Squires, E. L. 1992. Effect of volume and concentration of spermatozoa on embryo recovery in mares. Theriogenology. 37:1233–1239

Johnson L. A., et al., 1987. Flow cytometry of X- and Y-chromosome bearing sperm for DNA using an improved preparation method and staining with Hoechst 333–42. Garnete Research 17: 203–212

Johnson, "Gender preselection in Mammals: An overview", Dtsch. Tierarztl. Wschr, Vol. 103, Aug./Sep. 1996, pp 288–291.

Johnson, A. L. 1986. Pulsatile release of gonadotropin releasing hormone advances ovulation in cycling mares. Biol. Reprod. 35:1123E 1130.

Johnson, A. L. and Becker, S. E. 1988. Use of gonadotropin-releasing hormone (GnRH) treatment to induce multiple ovulations in the anestrous mare. Eq. Vet. Sci. 8:130–134.

Johnson, L., "Sex Preselection by Flow Cytometric Separation of X and Y Chromosome-Bearing Sperm Based on DNA Difference: a Review", Reproduction and Fertilization Development 7, 1995, pp. 893–903.

Johnson, L., "Successful Gender Preselection in Farm Animals", Agricultural Biotechnology, 1998, pp. 439–452.

Johnson, L. A. 1988. Flow cytometric determination of spermatozoa sex ratio in semen purportedly enriched for X or Y bearing spermatozoa. Theriogenology. 29:265. abstr.

Johnson, L. A. 1992. Gender preselection in domestic animals using flow cytometrically sorted sperm. J Anim. Sci. Suppl 1.70:8–18.

Johnson, L. A. 1994. Isolation of X- and Y-bearing spermatozoa for sex preselection. In: Oxford Reviews of Reproductive Biology. Ed. H H Charlton. Oxford University Press. 303–326.

Johnson, L. A. 1995. Sex preselection by flow cytometric separation of X and Y chromosome bearing spermatozoa based on DNA difference: a review. Reprod. Fert. Dev. 7:893–903.

Johnson, L. A. and Schulman, J. D. 1994. The safety of sperm selection by flow cytometry. Ham. Reprod. 9(5):758.

Johnson, L. A., "Sex preselection in swine: altered sex ratios in offspring following surgical insemination of flow-sorted X- and Y-bearing sperm", Reprod. Domest. Anim. 26:309–314, 1991

Johnson, L. A., and Pinkel, D., "Modification of a Laser-Based flow Cytometer for High-Resolution DNA Analysis of Mammalian Spermatozoa", Cytometry 7, 1986, pp 268–273.

Johnson, L. A., et al., "Sex Preselection in Rabbits: Live Births from X and Y Sperm Separated by DNA and Cell Sorting", Exceptional Paper-Rapid Publication, XP-002103476, Biology of Reproduction 41, 199–203, 1989, pp 199–203.

Johnson, L. A., et al., 1994. Improved flow sorting resolution of X- and Y-chromosome bering viable sperm separation using dual staining and dead cell gating. Cytometry 17 (suppl 7):83. Johnson, L. A., Flook, J. P., Look, M. V. and Pinkel, D. 1987b. Flow sorting of X and Y chromosome bearing spermatozoa into two populations. Gam. Res. 16:203–212.

Johnson, L. A., Welch, G. R., Rens, W. and Dobrinsky, J. R. 1998. Enhanced flow cytometric sorting of manunalian X and Ysperm: high speed sorting and orienting no77.le for artificial insemination. Theriogenology. 49(1):361. abstr.

Joseph, R. L. "Carcass composition and meat quality in once calved heifers." In: J. C. Taylor (Ed.) The early calving of heifers and it's impact on beef production. 143. 1975

Joseph, R. L. and J. P. Crowley. "Meat quality of once-calved heifers." Irish J. of Agric. Research 10:281. 1971

Kachel, V., et al., A Uniform Lateral Orientation, Cused by Flow Forces, of Flat Particles in Flow-Through Systems@, The Journal of Histochemistry and Cytochemistry, 1997, Vol. 25, No. 7, pp 774 –780.

Kanayama, K., Sankai, T., Nariaik, K., Endo, T. and Sakuma, Y. 1992b. Pregnancy by means of tubal insemination and subsequent spontaneous pregnancy in rabbits. J. lnt. Med. Res. 20:401–405.

Karabinus, et al., "Effects of Egg Yolk-Citrate and Milk Extenders on Chromatin Structured Viability of Cryopreserved Bull Sperm", Journal of Dairy Science, Vol. 74, No. 11, 1999, pp 3836–3848.

Keeling, P. C. B. M. S. T. G. D. I. a. P. W. J., "A modeling study of once-bred heifer beef production." Proceedings of the New Zealand Society of Animal Production. 51. 1991

Kilicarslan, M. R., Horoz, H., Senunver, S. C., Konuk, S. C., Tek, C. and Carioglu, B. 1996. Effect of GMRH and hCG on ovulation and pregnancy in mares. Vet. Rec. 139:119–120.

Kinder, J. E., et al. "Endocrine basis for puberty in heifers and ewes." J. Repro. and Fertility 393. 1995

Klindt, J. and J. D. Crouse. "Effect of ovariectomy and ovariectomy with ovarian auto transplantation on feedlot performance and carcass characteristics of heifers." J. Anim. Sci. 68:3481. 1990

Klosterman, E. W. and C. F. Parker. "Effect of size, beed and sex upon feed efficiency in beef cattle." North Central Regional Research Publication 235, Ohio Agric. Research and Development Center 1090:3. 1976

Kniffen, D. M., Wagner, W. R., and Lewis. P. E. "Effects oflong-tenn estrogen implants in beef heifers." I. Anim. Sci. 77:2886. 1999

Koch, R. M., et al., "Characterization of biological types of cattle -Cycle-II .3." Carcass composition, quality and palatability. I. Anim. Sci. 49:448. 1919

Lapin, D. R. and Ginther, O. J. 1977. Induction of ovulation and multiple ovulations in seasonally anovulatory and ovulatory mares with an equine pituitary extract. J. Anim. Sci. 44:834–842.

Laster, D. B., "Factors affecting dystocia and effects of dystocia on subsequent reproduction in beef-cattle." J. Anim. Sci. 36:695. 1973

Lawrenz, R. 1985. Preliminary results of non-surgical intrauterine insemination of sheep with thawed frozen semen. J S Afr. Vet. Assoc. 56(2):61–63.

Levinson, G., et al, 1995. DNA-based X-enriched sperm separation as an adjunct to preimplantation genetic testing for the preparation of X-linked disease. Mol. Human Reprod. 10:979–982.

Lindsey, A., et al., A Hysteroscopic Insemination of Mares with Nonfrozen Low-dose Unsexed or Sex-sorted Spermatozoa@, currently unpublished, pp. 1–15.

Linge, F. 1972. Faltforsok med djupfrost sperma (field trials with frozen sperm). Farskotsel. 52:12–13.

Lonergan, P., et al., "Effect of Time Interval from Insemination to First Cleavage on the Development of Bovine Embryos In Vitro and In Vivo", Theriogenology, 1999, p. 326

Long, C. R., Rath, D., Welch, G. R., Schreier, L. L., Dobrinsky, J. R. and Johnson, L. A. 1998. A ln vitro production of porcine embryos from semen sorted for sex with a high speed cell sorter: comparison of two fertilization media.@, Theriogenology. 49(1):363. abstr.

Loy, R. G. and Hughes, J. P. 1965. The effects of human chorionic gonadotropin on ovulation, length of estrus, and fertility in the mare. Cornell Vet. 56:41–50.

Lu, K. H., et al., "In Vitro Fertilization with Flow-Cytometrically-Sorted Bovine Sperm", Theriogenology 52, 1999, pp. 1393–1405.

Lynch, I. M., et al., "Influence of timing of gain on growth and reproductive performance of beef replacement heifers." I. Anim. Sci. 75:1715. 1997

Macmillan, K. L. and A. M. Day, "Prostaglandin F2a—A Fertility Drug In Dairy Cattle?", Ruakura Animal Research Station, Private Bag, Hamilton, New Zealand, Theriogenology, September 1982, Vol. 18 No. 3, pages 245–253

Martin, A. H., et al., "Characteristics of youthful beef carcasses in relation to weight, age and sex .3. meat quality attributes." Canadian I. Anim. Sci. 51:305. 1971

Martin, L. C., J. S. Brinks, R. M. Bourdon, and L. V. Cundiff. "Genetic-effects on beef heifer puberty and subsequent reproduction." J. Anim. Sci. 70:4006. 1992

Matsuda, Y. and Tobari, I. 1988. Chromosomal analysis in mouse eggs fertilized in vitro with sperm exposed to ultra-violet light (UV) and methyl and ethyl methanesulfonate (MMS and EMS). Mutat. Res. 198:131–144.

Matulis, R. J., F. K. Mckeith, D. B. Faulkner, L. L. Berger, and P. George. "Growth and carcass characteristics of cull cows after different times-on-feed." J. Anim. Sci. 65:669. 1987

Mauleon, P. "Recent research related to the physiology of puberty." Commission of the European Communities. The early calving of heifers and it's impact on beef production. 1975

Maxwell, W. and Johnson, L., "Chlortetracycline Analysis of Boar Spermatozoa after Incubation, Flow Cytometric Sorting, Cooling, or Cryopreservation", Molecular Reproduction and Development 46, 1997, pp. 408–418.

Maxwell, W. M. C., Evans, G., Rhodes, S. L., Hillard, M. A. and Bindon, B. M. 1993. Fertility of Superovulated Ewes after Intrauterine or Oviductal Insemination with Low Numbers of Fresh or Frozen-Thawed Spermatozoa. Reprod. Fertil. Dev. 5:57–63.

Mccomlick, R. J. "The flexibility of the collagen compartment of muscle." Meat Sci. 36:79. 1994

McCue, P. M. 1996. Superovulation. Vet. Clin. N. Amer. Eq. Prac. 12:1–11.

McCue, P. M., Fleury, J. J., Denniston, D. J., Graham, J. K. and Squires, E. L. 1997. Oviductal insemination in the mare. $7^{th}$ Int Symp. Eq. Reprod. 133. abstr.

McDonald, L. E. 1988. Hormones of the pituitary gland. In: Veterinary Pharmacology and Therapeutics. $6^{th}$ ed. Edited by N. H. Booth and L. E. McDonald. Ames, Iowa State Univ. Press. pp. 590.

McKenna, T., Lenz, R. W., Fenton, S. E. and Ax, R. L. 1990. Nonreturn rates of dairy cattle following uterine body or comual insemination. J. Dairy Sci. 73:1179–1783.

McKinnin, A. and Voss, J., "Equine Reproduction", Lea & Febiger, Philadelphia, 1993, pp 291, 299–302, 345–348, 73

McKinnon, A. et al, 1993. Predictable ovulation in mares treated with an implant of the GnRH analogue deslorelin. Eq. Vet. J. 25:321–323.

McKinnon, A. O. et al, 1996. Repeated use of a GnRH analogue deslorelin (Ovuplant) for hastening ovulation in the transitional mare. Eq. Vet. J. 29:153–155.

McNutt, et al., "Flow Cytometric Sorting of Sperm: Influence on Fertilization and Embryo/Fetal Development in the Rabbits", Molecular Reproduction and Development, Vol. 43, 1996, pp 261–267.

Meilgaard, M., G. V. Civille, and B. T. Carr. "Sensor Evaluation Techniques." CRC Press Inc., Boca Raton, Fla. 1991

Meinert, C., et al., "Advancing the time of ovulation in the mare with a short-term implant releasing the GnRH analogue deslorelin", Equine Veterinary Journal, 25, 1993, pp 65–68.

Merton, J., et al., "Effect of Flow Cytometrically Sorted Frozen/Thawed Semen on Success Rate of In Vitro Bovine Embryo Production", Theriogenology 47, 1997, pp. 295.

Meyers, P. J., Bowman, T., Blodgett, G., Conboy, H. S., Gimenez, T., Reid, M. P., Taylor, B. C., Thayer, J., Jochle, W. and Trigg, T. E. 1997. Use of the GnRH analogue, deslorelin acetate, in a slow release implant to accelerate ovulation in oestrous mares. Vet. Rec. 140:249–252.

Michaels, Charles, "Beef A.I. Facilities that work", Proc. Fifth N.A.A.B Tech. Conf. A.I. Reprod. Columbia, Mo. pp. 20–22.

Michel, T. H., Rossdale, P. D. and Cash, R. S. G. 1986. Efficacy of human chorionic gonadotrophin and gonadatrophin releasing hormone for hastening ovulation in Thoroughbred mares. Eq. Vet. J. 6:438–442.

Miller, S. J. 1986. Artificial Breeding Techniques in Sheep. In Morrow, D.A. (ed): Current Therapy in Theriogenology 2. Philadelphia, WB Saunders.

Mirskaja, L. M. and Petrapavlovskii, V. V. 1937. The reproduction of normal duration of heat in the mare by the administration of Prolan. Probi. Zivotn. Anim. Breed. Abstr. 5:387.

Moe, P. W., H. F. Tyrrell, and W. P. Flatt. "Energetics ofbodytissue mobilization." J. of Dairy Sci. 54:548.

Molinia, F. C., Gibson, R. J., Brown, A. M., Glazier, A. M. and Rodger, J. C. 1998. Successful fertilization after superovulation and laparoscopic intrauterine insemination of the brushtail possum, Trichosurus vulpecula, and tammar wallaby, Macropus eugenii. J.Reprod. Fert. 112:9–17.

Moms, S. T., et al., "Biological efficiency: How relevent is this concept to beef cows in a mixed livestock seasonal pasture supply context?" Proceedings of the New Zealand Society of Animal Production 54:333. 1994

Monensin." J. Anim. Sci. 55:357–362. 1982

Moran, C., J. F. Quirke, and J. F. Roche. "Puberty in heifers—a review." Animal Reproduction Sci. 18:167. 1989

Morcom, C. B. and Dukelow, W. R. 1980. A research technique for the oviductal insemination of pigs using laparoscopy. Lab. Anim. Sci. 1030–1031.

Morgan, J. B., et al., "National beef tenderness survey." J. Anim. Sci. 69:3274. 1991

Morris, L. H., et al., "Hysteroscopic insemination of small numbers of spermatozoa at the uterotubal junction of preovulatory mares", Journal of Reproduction and Fertility, Vol. 118, pp. 95–100 (2000)

Moseley, W. M., et al., 1982. Relationship of Growth and Puberty in Beef Heifers Fed Mount, D. E. "Fibrous and non-fibrous carbohydrate supplementation to ruminants grazing forage from small grain crops." M. S. Thesis. Colorado State University. 2000

Muller, W. and Gautier, F. 1975. Interactions of heteroaromatic compounds with nucleic acids. Euro. J Biochem. 54:358.

Munne, S. 1994. Flow cytometry separation of X and Y spemnatozoa could be detrimental to human embryos. Hum. Reprod. 9(5):758

Myers, S. E., "Performance and carcass traits of early-weaned steers receiving either a pasture growing period or a finishing diet at weaning." J. Anim. Sci. 77:311. 1999

Myers, S. E., et al., "Comparison of three weaning ages on cow-calfperformance and steer carcass traits." J. Anim. Sci. 77:323. 1999

Myers, S. E., et al., "Production systems comparing early weaning to normal weaning with or without creep feeding for beef steers." J. Anim. Sci. 77:300. 1999

Nix, I. P., I. C. Spitzer, and P. I. Chenoweth. "Serum testosterone concentration, efficiency of estrus detection and libido expression in androgenized beef cows." Therio. 49:1195. 1998

Nowshari, et al., "Superovulation of Goats with Purified pFSH Supplemented with Defined Amounts of pLH", Theriogenology, Vol 43, 1995, pp 797–802.

Nowshari, et al., Theriogenology, Vol 43, 1995, pp 797–802.

NRC. Nutrient requirements for beef cattle. National Academy of Sci. National Research Council, Washington, DC. 1996

Olson, S. E. and Seidel, G. E. Jr., "Reduced Oxygen Tension and EDTA improve Bovine Zygote Development in a Chemically Defined Medium", Journal of Animal Science 78, 2000, pp. 152–157.

Owen, J. B. "The maiden female-a means of increasing meat production." Proc. Symp. on the use of once bred heifers and gilts. 1973

Pace, M. M. and Sullivan, J. J. 1975. Effect of timing of insemination, numbers of spermatozoa and extender components on pregnancy rates in mares inseminated with frozen stallion semen. J Reprod. Fert. Suppl. 23:115–121.

Parent U.S. Application Ser. No. 09/001,394, entitled "Sheath Fluids and Collection Systems for Sex-Specific Cytometer Sorting of Sperm", filed on Dec. 31, 1997, 87 total pages which includes four drawings.

Parrish, J., et al., "Capacitation of Bovine Sperm by Heparin", Technology of Reproduction 38, 1988, pp. 1171–1180.

PCT application, PCT/US99/17165, filed Jul. 28, 1999, entitled "Equine System for Non-Surgical Artificial Insemination".

PCT application, PCT/US98/27909, filed Dec. 31, 1998, entitled "Commercially Practical Sex-Specific Insemination of Mammnals".

Peippo, J., et al., "Sex diagnosis of equine preimplantation embryos using the polymerase chain reaction", Theriogenology, Vol. 44 619–627 (1995)

Perry, E. J. 1968. Historical Background In: The Artificial lnsemination of Farm Animals. $4^{th\ ed.}$ Edited by E. J. Perry. New Brunswick, Rutgers University Press, pp. 3–12.

Petersen, G. A., et al, "Cow and Calf Performance and Economic Considerations of Early Weaning of Fall-Born Beef Calves", J. Anim. Sci., 1987, 64:15, pp 15–22.

Petit, M. "Early Calving in Suckling Herds." In: (Ed.) J. C. Taylor. The early calving of heifers and it's impact on beef production. 157. 1975

Pickett G W, et al., "Management of the mare for maximum reproductive efficiency", Bulletin No. 6 Colorado State University, Ft. Collins Colo. (1989)

Pickett, B. W, et al., 1976. Factors influencing the fertility of stallion spermatozoa in an A.I. program. Proc. $8^{th}$Intemat. Congr. Anim. Reprod. A.I. Krakow, Poland. 4: 1049–1052.

Pickett, B. W. and Back, D. G. 1973. Procedures for preparation, collection, evaluation and insemination of stallion semen. C.S.U. Exp. Sta. Artira. Reprod. Lab. Gen. Series Bull. 935.

Pickett, B. W., and Shiner, K. A., "Recent developments in artificial insemination in horses", Livestock Production Science, 40, 1994, pp 31–36.

Pickett, B. W., Burwash, L. D., Voss, J. L. and Back, D. G. 1975b. Effect of seminal extenders on equine fertility. J. Anim. Sci. 40:1136–1143.

Pinkel, D., et al, "Flow Cytometric Determination of the Proportions of X- and Y-Chromosome-Bearing Sperm in Samples of Purportedly Separated Bull Sperm", Journal of Animal Science, Vol. 60, No. 5, 1985, pp 1303–1307.

Pinkel, D., Gledhill, B. L., Van Dilla, M. A., Stephenson, D. and Watchmaker, G. 1982b. High resolution DNA measurements of mammalian spermatozoa. Cytometry. 3:1–9. (1982b)

Polge, E. J., "Historical Perspective of Al: Commercial Methods of Producing Sex Specific Semen, IVF Procedures", Proceedings of the $16^{th}$ Technical Conference on Artificial Insemination & Reproduction, Cambridge, England, 1996, pp. 7–11.

Purvis, H. T. and J. C. Whittier. "Effects ofionophore feeding and anthelmintic administration on age and weight at puberty in spring-bom beef heifers." J. Anim. Sci. 74:736–744. 1996

Randel, R. D. "Nutrition and postpartum rebreeding in cattle." J. Anim. Sci. 68:853. 1990

Rath, D., et al., "Low Dose Insemination Technique in the Pig", Boar Semen Preservation IV, 2000, pp. 115–118.

Rath, D., et al., "Production of Piglets Preselected for Sex Following in Vitro Fertilization with X and Y Chromosome-Bearing Spermatozoa Sorted by Flow Cytometry", Theriogenology, 47, 1997, pp 795–800.

Reiling, B. A., et al., "Effect of Prenatal Androgenization on Performance, Location, and Carcass and Sensory Traits on Heifers in Single Calf Heifer System", J. Anim. Sci., 1995, 73: 986, pp 986–992.

Rens, W., et al, "A Novel Nozzle for More Efficient Sperm Orientation to Improve Sorting Efficiency of X and Y Chromosome-Bearing Sperm", Cytometry 33, 1998, pp. 476481

Rens, W., et al., "Improved Flow Cytometric Sorting of X- and Y-Chromosome Bearing Sperm: Substantial Increase in Yield of Sexed Semen", Molecular Reproduction and Development, 1999, pp 50–56.

Rieger, D., et al, "The Relationship Between the Time of First Cleavage of Fertilized Cattle Oocytes and Their Development to the Blastocyst Stage", Theriogenology, 1999, pp. 190.

Ritar, A. and Ball, A. 1991. Fertility of young cashmere goats after laparoscopic insemination. J. Agr. Sci. 117: 271–273.

Roberts, J. R. 1971. In: Veterinary Obstetrics and Genital Diseases. Ithaca, N.Y. pp. 740–749.

Romita, A. "Some considerations on the beef situation in Italy." (Ed.) J. C. Taylor. The early calving of heifers and it's impact on beef production. 23. 1975

Roth, T. L., Wolfe, B. A., Long, J. A., Howard, J. and Wildt, D. E. 1997. Effects of equine chorionic gonadotropin, human chorionic gonadotropin, and laparoscopic artificial insemination on embryo, endocrine, and luteal characteristics in the domestic cat. Bio Reprod. 57:165–171. Roux, M., J. H. Teissier, J. Bonnemaire, and R. Dumont. "Early calving heifers versus maiden heifers for beef-production from dairy herds. 1." The effects of genotype (Friesian and Charolais x Friesian) and 2 feeding levels in the rearing period on growth and carcass quality. Livestock Prod. Sci. 16:1. 1987

Rowley, H-S., Squires, E. L. and Pickett, B. W. 1990. Effect of insemination volume on embryo recover in mares. J. Equine Vet. Sci. 10:298–300.

Roy, J. H. B. "Rearing dairy-herd replacements." J. of the Soc. ofdairy Technology 31:73–79. 1978

Rutter, L. M., et al., "Effect of abomasal infusion of propionate on the GnRH-induced luteinizing-hormone release in prepuberal heifers." J. Anim. Sci. 56:1167. 1983

Salamon, S. 1976. Artificial Insemination of Sheep. Chippendale, New South Whales. Publicity Press. p. 83–84.

Salisbury, G. W. and VanDemark, N. L. 1961. Physiology ofReproduction and Artificial Insemination of Cattle. San Francisco: Freeman and Company.

SAS, SAS/STAT, "Useres Guide (Release 6.03)", SAS Inst. Inc., Cary, N.C., 1988. 3 pages SAS. "The SAS System for Windows." Ver 7.0. Rel 6.12. SAS Inst.lnc., Cary, N.C. 2000

Schenk, J. L., T. K. Suh, D. G. Cran, and G. E. Seidel. "Cryopreservation of flow-sorted bovine spennatozoa." Therio. 52:1375. 1999

Schenk, J. L. and Seidel, Jr., G. E., "Imminent Commercialization of Sexed Bovine", Proceedings, The Range Beef Cow Symposium XVL, 1999, pp 89–96.

Schillo, K. K., J. B. Hall, and S. M. Hileman. "Effects of nutrition and season on the onset of puberty in the beef heifer." J. Anim. Sci. 70:3994. 1992

Schmid R. L., et al, "Fertilization with Sexed Equine Spermatozoa Using Intracytoplasmic Sperm Injection and Oviductal Insemination", 7th International Symposium On Equine Reproduction, pp. 139 (Abstract) (1998) Schnell, T. D., K. E. Belk, J. D. Tatum, R. K. Miller, and G. C. Smith. "Performance, carcass, and palatability traits for cull cows fed high-energy concentrate diets for 0, 14, 28, 42, or 56 days." J. Anim. Sci. 75:1195. 1997

Schoonmaker, J. P., et al., "Effects of age at weaning and implant strategy on growth of steer calves." J. Anim. Sci. (Suppl2) 76:71 (Abstr.). 1998

Seidel, G. E. and L. A. Johnson. "Sexing mammalian spenn-overview." Therio. 52: 1267. 1999

Seidel, G. E., "Insemination of heifers with sexed sperm." Therio. 52:1407. 1999

Seidel, G. E. Jr., "Uterine Horn Insemination of Heifers With Very Low Numbers of Nonfrozen and Sexed Spermatozoa", Atlantic Breeders Cooperative, Theriogenology 48: pp. 1255–1264, (1997)

Seidel, G. E. Jr., Cran, D. G., Herickoff, L. A., Schenk, J. L., Doyle, S. P. and Green, R. D. 1999. Insemination of heifers with sexed frozen or sexed liquid semen. Theriogenology. 51. (in press). abstr.(1 999)

Seidel, G. E., Jr., et al, "Artificial Insemination With X-and Y-Bearing Bovine Sperm", Animal Reproduction and Biotechnology Laboratory, Colorado State University, Fort Collins, Colo; Germplasm and Gamete Physiology Lab, ARS, USDA, Beltsville, Md; Atlantic Breeders Coop, Lancaster, Pa; DUO Diary, Loveland, Colo, U.S.A. January 1996.

Seidel, G. E., Jr., et al, "Insemination Of Heifers With Very Low Numbers Of Frozen Spermatozoa.", Colorado State University, Fort Collins, Atlantic Breeders Cooperative, Lancaster, Pa, DUO Dairy, Loveland, Colo, July 1996.

Seidel, Jr., G. E., et al, "Insemination of Holstein Heifers With Very Low Numbers Of Unfrozen Spermatozoa", Colorado State University, Atlantic Breeders Cooperative, (1995)

Seidel, Jr., G. E. et al, "Insemination Of Heifers With Very Low Numbers Of Frozen Spermatozoa", Colorado State University (1996)

Sell, R. S., D. L. Watt, R. D. Little, and T. A. Petry. "Single-callheifer profitability compared to other north dakota beef production systems." Department of Ag. Eco., North Dakota State University, Ag. Econ. Rpt. 20.

Senger, P. L., Becker, W. C., Davidge, S. T., Hillers, J. K. and Reeves, J. J. 1988. Influence of comual insemination on conception rates in dairy cattle. J Anim. Sci. 66:3010–3016.

Shackelford, S. D., M. Koohmaraie, and T. L. Wheeler. "Effects of slaughter age on meat tenderness and usda carcass maturity scores of beef females." I. Anim. Sci. 73:3304. 1995

Shelton, J. N. and Moore, N. W. 1967. The response of the ewe tot pregnant mare gonadotropin and to horse anterior pituitary extract. J. Reprod. Fert. 14:175–177.

Shilova, A. V., Platov, E. M. and Lebedev, S. G. 1976. The use of human chorionic gonadothrophin for ovulation date regulation in mares. VIIIth Int. Congr. On Anim. Repro. and A.I. 204–208.

Shorthose, W. R. and P. V. Harris. "Effect of animal age on the tenderness of selected beef muscles." I. Food Sci. 55:1-. 1990

Silbennann, M., "Honnones and Cartilage. Cartilage: development, differentiation, and growth." pp. 327–368. Academic Press, Inc. 1983

Simon, M., "The effect of management option on the perfonnance of pregnant feedlot heifers." M.S. Thesis. Kansas State University. 1983

Smith, G. C., B. W. Berry, J. W. Savell, and H. R. Cross. "USDA maturity indexes and palatability of beefrib steaks." J. of Food Quality 11:1. 1988

Smith, G. C., et al., "Relationship of usda maturity groups to palatability of cooked beef." J. of Food Sci. 47:1100. 1982

Squires, E., Simultaneous Analysis of Multiple Sperm Attributes by Flow Cytometry☐, Diagnostic Techniques and Assisted Reproductive Technology, The Veterinary Clinics of North America, Equine Practice, Vol. 12, No. 1, April 1996, pp 127–130.

Squires, E. L, Moran, D. M., Farlin, M E., Jasko, D. J., Keefe, T. J., Meyers, S. A., Figueiredo, E., McCue, P. M. and Jochle, W. 1994. Effect of dose of GnRH analogue on ovulation in mares. Theriogenology. 41:757–769.

Squires, E. L., "Early Embryonic Loss in Equine Diagnostic Ultrasonography", $1^{st}$ Ed. pp 157–163 Eds Rantanen & McKinnon. Williams and Wilkins, Baltimore, Md. (1998)

Squires, E. L., et al, "Cooled and frozen stallion semen", Bulletin No. 9, Colorado State University, Ft. Collins, Colo. (1999)

Stellflug, J. N., D. K. Ran, R. D. Randel, and Eo L. Moody. "Plasma estrogens in peri-parturient cow." Therio 10:269. 1978

Stevenson, J. S., M. W. Smith, J. R. Jaeger, L. R. Corah, and D. G. Lefever. "Detection of estrus by visual observation and radiotelemetry in peripubertal, estrus-synchronized beefheifers." J. Anim. Sci. 74:729. 1996

Story, C. E., R. J. Rasby, R. T. Clark, and C. T. Milton. "Age of calf at weaning of spring-calving beef cows and the effect on cow and calf perfomlance and production economics." J. Anim. Sci. 78:1403. 2000

Sullivan, J. J., Parker, W. G. and Larson, L L. 1973. Duration of estrus and ovulation time in nonlactating mares given human chorionic gonadotropin during three successive estrous periods. J.A.V.M.A. 162:895–898.

Swanson, E. W. "Future research on problems of increasing meat production by early calving." Comm. Eur. Commun., Eur. 5545.1975. The Early Calving of Heifers and its Impact on Beef Production.

Taljaard, T. L., Terblanche, S. J., Bertschinger, H. J. and Van Vuuren, L. J. 1991. The effect of the laparoscopic insemination technique on the oestrus cycle of the ewe. J. S Afr. Vet. Assoc. 62(2):60–61.

Tatum, J. D., G. C. Smith, B. W. Berry, C. E. Murphey, F. L. Williams, and Z. L. Carpenter. "Carcass characteristics, time on feed and cooked beef palatability attributes." J. Anim. Sci. 50:833. 1980

Taylor, C. S., Moore, A. J. Thiessen, R. B. and Bailey, C. M., AFRC Animal Breeding Research Organisation, West Mains Road, Edinburg EH9 3JQ, "Efficiency of Food Utilization in Traditional and Sex-Controlled Systems of Beef Production", pp 401–440.

Taylor, S. C. S., A. J. Moore, R. B. Thiessen, and C. M. Bailey. "Efficiency of food utilization in traditional and sex-controlled systems of beef-production." Animal Production 40:401. 1985

Tervit, H. R., et al., "Successful Culture In Vitro of Sheep and Cattle Ova", Agricultural Research Council, Unit of Reproduction Physiology and Biochemistry, University of Cambridge, 1972, p. 493–497.

Unruh, J. A. "Effects of endogenous and exogenous growth-promoting compounds on carcass composition, meat quality and meat nutritional-valu~." J. Anim. Sci. 62:1441. 1986

U.S. application, Ser. No. 09/454,488, entitled "Improved Flow Cytometer Nozzle and Flow Cytometer Sample Handling Methods", filed Dec. 3, 1999.

U.S. application, No. 60/238,294, entitled "Hysteroscopic Insemination of Mares" filed Oct. 5, 2000.

U.S. application, Ser. No. 09/448,643, entiled "Multiple Sexed Embryo Production System for Mammals", filed Nov. 24, 1999.

U.S. application, Ser. No. 09/511,959 entitled "Methods For Improving Sheath Fluids and Collection Systems For Sex-Specific Cytometer Sorting of Sperm", filed Feb. 23, 2001.

U.S. application Ser. No. 09/001,394, entitled "Sheath Fluids and Collection Systems for Sex-Specific Cytometer Sorting of Sperm", filed on Dec. 31, 1997, 87 total pages which includes four drawings.

U.S. application Ser. No. 09/015,454, entitled "System for Improving Yield of Sexed Embryos in Mammals", filed on Jan. 29, 1998, 59 total pages which includes drawings.

U.S. application No. 60/211093, entitled "Integrated System for Herd Management Using Sexed Semen", filed Jun. 12, 2000.

U.S. application entitled "System For Separating Frozen-Thawed Sperm Cells Into X-Chromosome And Y-Chromosome Bearing Populations", filed Nov. 28, 2000.

U.S. application Ser. No. 60/094,720, entitled "System for Low Dose Insemination of Equines", filed Jul. 30, 1998.

U.S. application Ser. No. 60/113,143, entitled "Equine Insemination System", Dec. 18, 1998.

U.S. application Ser. No. 60/203,089, entitled "Detector System for Resolving Small Differences in Photo-generated Signal", filed May 9, 2000.

U.S. application Ser. No. 60/211093, entitled "Integrated System for Herd Management Using Sexed Semen", filed Jun. 12, 2000.

U.S. application Ser. No. 60/224,050., entitled "Integrated System for Herd Management With Terminal-Cross Program Using Sexed Semen", filed Aug. 9, 2000.

USDA "Official United States standards for grades of carcass beef." Agric, Marketing Serv., USDA Washington, DC. 1997

Vazquez, J. et al., "Nonsurgical Uterotubal Insemination in the Mare", Proceedings of the 44th Annual Convention of the American Association of Equine Practitioners, Baltimore, Md., Dec. 6–9, 1998, Vol. 44, pp 68–69

Vazquez, J., et al., "A. I. in Swine; New Strategy for Deep Insemination with Low Number of Spermatozoa Using a Non-surgical Methodology", 14$^{th}$ International Congress on Animal Reproduction, Vol. 2, Stockhlom, July, 2000, p. 289.

Vazquez, J., et al., "Development of a Non-surgical Deep Intra Uterine Insemination Technique", IV International Conference on Boar Semen Preservation, Maryland, August, 1999, p 35 and photo of display board.

Vazquez, J., et al., "Successful Low-Dose Insemination by a Fiberoptic Endoscope Technique in the Sow", Proceedings Annual Conference of the International Embryo Transfer Society, Netherlands, Theriogenology, Vol. 53, January, 2000, pp. 201.

Vazquez, J., et al.,"Hypoosmotic Swelling Test as Predictor of the Membrane Integrity in Boar Spermatozo", Boar Semen Preservation IV, IVth International Conference on Boar Semen Preservation, Maryland, pp. 263.

Vidament, M., Dupere, A. M., Julienne, P., Evain, A., Noue, P. and Palmer, E. 1997. Equine frozen semen freezeability and fertility field results. Theriogenology. 48:907.

Vincent, B. C., S. D. M. Jones, L. E. Jeremiah, M. A. Price, and J. A. Newman. "Carcass characteristics and meat quality of once-calved heifers." Canadian J. Anim. Sci. 71:311 1991

Voss, J. L. and Pickett, B. W. 1976. Reproductive management of the broodmare. C.S.U. Exp. Sta. Anim. Reprod. Lab. Gen. Series. Bull. 1–12.

Voss, J. L., Pickett, B. W., Burwash, L. D. and Daniels, W. H. 1974. Effect of human chorionic gonadotropin on duration of estrous cycle and fertility of normally cycling, nonlactating mares. J.A.V.M.A. 165:704–706.

Voss, J. L., Squires, E. L., Pickett, B. W., Shideler, R. K. and Eikenberry, D. J. 1982. Effect of number and frequency of inseminations on fertility in mares. J. Reprod. Fertil. Suppl. 32:53–57.

Waggoner, A. W., M. E. Dikeman, I. R. Brethour, and K. E. Kemp. "Performance, carcass, cartilage calcium, sensory and collagen traits of longissimus muscles of open versus 30-month-old heifers that produced one calf." I. Anim. Sci. 68:2380. 1990

Welch G. R., et al., 1994. Fluidic and optical modifications to a FACS IV for flow sorting of X- and Y-chromosome bearing sperm based on DNA. Cytometry 17 (suppl. 7):74.

Welch, G., et al., Flow Cytometric Sperm Sorting and PCR to Confirm Separation of X- and Y-Chromosome Bearing Bovine Sperm☐, Animal Biotechnology, 6 (2), 131–139, 1995, pp 131–139.

Wheeler, T. L., L. v. Cundiff, and R. M. Koch. "Effect of marbling degree on beef palatability in Bos- Taurus and Bos-Indicus cattle." J. Anim. Sci. 72:3145. 1994

Wickersham, E. W. and L. H. Schultz. "Infilience of age at first breeding on growth, reproduction, and production of well-fed holstein heifers." J. Dairy Sci. 46:544. 1963

Wilson, C. G., Downie, C. R., Hughes, J. P. and Roser, J. F. 1990. Effects of repeated hCG injections on reproductive efficiency in mares. Eq. Vet. Sci. 4:301–308.

Wilson, M. S. 1993. Non-surgical intrauterine artificial insemination in bitches using frozen semen. J.Reprod. Fert Suppl. 47:307–311.

Woods, J. and Ginther, O. J. 1983. Recent studies related to the collection of multiple embryos in mares. Theriogenology. 19:101–108.

Woods, J., Bergfelt, D. R. and Ginther, O. J. 1990. Effects of time of insemination relative to ovulation on pregnancy rate and embryonic-loss rate in mares. Eq. Vet. J. 22(6): 410–415.

XP-002103478, File Biosis, one page.

In addition, as to each term used it should be understood that unless its utilization in this application is inconsistent with such interpretation, common dictionary definitions should be understood as incorporated for each term and all definitions, alternative terms, and synonyms such as contained in the Random House Webster's Unabridged Dictionary, second edition are hereby incorporated by reference. However, as to each of the above, to the extent that such information or statements incorporated by reference might be considered inconsistent with the patenting of this/these invention(s) such statements are expressly not to be considered as made by the applicant(s).

In addition, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible in countries such as Australia and the like.

Thus, the applicant(s) should be understood to have support to claim at least: i) each of the staining, separation, isolation, insemination, or fertilization procedures as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, and x) the various combinations and permutations of each of the elements disclosed.

The claims set forth in this specification are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the subject matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

We claim:

1. A method of transporting oocytes, comprising the steps of:
   a. collecting oocytes from a female non-human mammal;
   b. entraining the oocytes in a fertilization medium;
   c. transferring the oocytes in said fertilization medium into at least one straw;
   d. sealing said at least one straw containing said oocytes;
   e. placing said at least one straw inside a closable incubation container capable of containing a separate, transportable incubation environment;
   f. transferring said at least one straw inside of said incubation container;
   g. establishing incubation conditions within said incubation container;
   h. sealing said incubation container; and
   i. transporting said oocytes from said female non-human mammal within said straw inside of said incubation container to another location.

2. A method of transporting oocytes as described in claim 1, wherein said female non-human mammal is selected from the group consisting of non-human primates, bovids, ovids, equids, swine, and dolphins.

3. A method of transporting oocytes as described in claim 1, wherein said fertilization medium comprises modified Tyrode's medium supplemented with 0.6 percent bovine serum albumin, 20 µg heparin per milliliter of Tyrode's medium, and a concentration of 5 milli-molar caffeine.

4. A method of transporting oocytes as described in claim 1, wherein between about 10 and about 15 of said oocytes are contained within about 50 micro-liters of said fertilization medium.

5. A method of transporting oocytes as described in claim 1, wherein said at least one straw has heat sealable aperture elements.

6. A method of transporting oocytes as described in claim 5, wherein said at least one straw has a interior volume of about 0.25 milliliters.

7. A method of transporting oocytes as described in claim 1, wherein said incubation container has sealable aperture elements.

8. A method of transporting oocytes as described in claim 7, wherein said incubation container comprises a glass tube.

9. A method of transporting oocytes as described in claim 1, wherein said incubation conditions comprise an atmosphere of 5 percent carbon dioxide in air and a temperature of 39 degrees Centigrade within said incubation container.

10. A method of transporting oocytes as described in claim 1, further comprising the step of transferring sperm cells to said at least one straw containing said oocytes in said fertilization medium.

11. A method of transporting oocytes as described in claim 10, wherein said step of transferring sperm cells to said at least one straw containing said oocytes comprises establishing a concentration of sperm cells in said fertilization medium of about 1 million to about 2 million per milliliter of fertilization medium.

12. A method of transporting oocytes as described in claim 1, further comprising the step of separating spermatozoa into enriched X-chromosome bearing and Y-chromosome populations prior to said step of transferring the oocytes in said fertilization medium into said at least one straw.

13. A method of transporting oocytes as described in claim 12, further comprising the step of transferring separated sperm cells to said at least one straw containing oocytes.

14. A method of transporting oocytes as described in claim 13, wherein said step of transferring separated sperm cells to said at least one straw containing oocytes comprises establishing a concentration of said separated sperm cells in said fertilization medium of about 1 million to about 2 million per milliliter of fertilization medium.

15. A method of transporting oocytes as described in claims 10, 11, 12, 13, or 14 further comprising the step of transferring said at least one straw containing said oocytes to said incubation container.

16. A method of transporting oocytes as described in claim 15, further comprising the step of establishing fertilization conditions within said incubation container.

17. A method of transporting oocytes as described in claim 16, wherein said step of establishing fertilization conditions within said incubation container comprises an atmosphere of 5 percent carbon dioxide in air at a temperature between about 37 degrees Centigrade and about 41 degrees Centigrade for a duration of about 18 hours to about 20 hours.

18. A method of transporting oocytes as described in claim 16, further comprising the step of transporting said oocytes in said fertilization conditions.

19. A method of transporting oocytes as described in claim 18, further comprising the step of fertilizing at least some of said oocytes during transport.

* * * * *